US010676765B2

(12) United States Patent
Marlière et al.

(10) Patent No.: US 10,676,765 B2
(45) Date of Patent: Jun. 9, 2020

(54) METHODS FOR PRODUCING 3-HYDROXY-3-METHYLBUTYRIC ACID

(71) Applicants: Global Bioenergies, Evry (FR); Scientist of Fortune, S.A., Luxembourg (LU)

(72) Inventors: Philippe Marlière, Luxembourg (LU); Maria Anissimova, Nozay (FR); Mathieu Allard, Rigny-la-Nonneuse (FR)

(73) Assignee: Global Bioenergies, Evry (FR)

( * ) Notice: Subject to any disclaimer, the term of this patent is extended or adjusted under 35 U.S.C. 154(b) by 0 days.

(21) Appl. No.: 15/511,684

(22) PCT Filed: Sep. 16, 2015

(86) PCT No.: PCT/EP2015/071185
§ 371 (c)(1),
(2) Date: Mar. 16, 2017

(87) PCT Pub. No.: WO2016/042012
PCT Pub. Date: Mar. 24, 2016

(65) Prior Publication Data
US 2017/0253896 A1 Sep. 7, 2017

(30) Foreign Application Priority Data
Mar. 6, 2015 (EP) ..................................... 15157918

(51) Int. Cl.
*C12P 7/52* (2006.01)
*C12N 9/10* (2006.01)
*C12N 9/12* (2006.01)
*C12N 9/88* (2006.01)
*C12N 15/52* (2006.01)

(52) U.S. Cl.
CPC .............. *C12P 7/52* (2013.01); *C12N 9/1029* (2013.01); *C12N 9/1217* (2013.01); *C12N 9/88* (2013.01); *C12N 15/52* (2013.01); *C12Y 203/01008* (2013.01); *C12Y 203/01019* (2013.01); *C12Y 207/02001* (2013.01); *C12Y 207/02007* (2013.01); *C12Y 207/02014* (2013.01); *C12Y 207/02015* (2013.01); *C12Y 402/01017* (2013.01); *C12Y 402/01018* (2013.01); *C12Y 402/01055* (2013.01); *C12Y 402/01059* (2013.01); *C12Y 402/01074* (2013.01); *C12Y 402/01116* (2013.01)

(58) Field of Classification Search
None
See application file for complete search history.

(56) References Cited

U.S. PATENT DOCUMENTS 9,738,875 B2 * 8/2017 Koepke ................. C12N 9/1029
2011/0165644 A1 * 7/2011 Marliere ................. C12N 9/88
435/167

FOREIGN PATENT DOCUMENTS

EP 2295593 A1 3/2011

OTHER PUBLICATIONS

D.P. Wiesenborn et al. "Phosphotransbutyrylase form Clostridium acetobutylicium ATCC 824 abd Its Role in Acidogenesis", Appl. Environ. Microbiol. 55(2):317-322 (Year: 1989).*
M.G.N. Hartmanis "Butyrate Kinase from Clostridium acetobutylicum", Journal of Biol. Chem. 262(2):617-621. (Year: 1987).*
S.J. Liu et al. "Exploitation of Butyrate Kinase and Phosphotransbutyrylase From Clostridium acetobutylicum for the in vitro Biosynthesis of Poly(hydroxylalkanoic acid)", Appl. Microbiol. Biotechnol. 53: 545-552. (Year: 2000).*
Wikipedia Enzyme Commission Number retrieved from https://en.wikipedia.org/wiki/Enzyme_Commission_number on Apr. 29, 2019 (Year : 2019).*
Baumgartner et al., "The Molecular Basis of Human 3-Methylcrotonyl-CoA Carboxylase Deficiency", The Journal of Clinical Investigation, vol. 107 (4), pp. 495-504, (2001).
Dhar et al., "Purification and Characterization of a Galactomyces Reessii Hydratase That Converts 3-Methylcrotonic Acid to 3-Hydroxy-3-Methylbutyric Acid", Journal of Industrial Microbiology & Biotechnology, vol. 28, No. 2, pp. 81-87, (2002).
European Search Report dated Feb. 11, 2015, received in EP 14 18 5180.8.
Gerbling et al., "Peroxisomal Degradation of 2-Oxoisocaproate. Evidence for Free Acid Intermediates", Botanica Acta. vol. 106 (5), pp. 380-387, (1993).
Luis et al., "Inhibition of 3-Methylcrotonyl-CoA Carboxylase Explains the Increased Excretion of 3-Hydroxyisovaleric Acid in Valproate-Treated Patients", Journal of Inherited Metabolic Disease, vol. 35, No. 3. pp. 443-449, (2012).
Teufel et al., "3-Hydroxypropionyl-Coenzyme A Dehydratase and Acryloyl-Coenzyme A Reductase, Enzymes of the Autotrophic 3-Hydroxypropionate/4-Hydroxybutyrate Cycle in the Sulfolobales", Journal of Bacteriology, vol. 191, No. 14, pp. 4572-4581, (2009).

(Continued)

Primary Examiner — Rebecca E Prouty
(74) Attorney, Agent, or Firm — Michele M. Wales; Inhouse Patent Counsel, LLC

(57) ABSTRACT

Described is a method for the conversion of 3-methylcrotonyl-CoA into 3-hydroxy-3-methylbutyric acid comprising the steps of:
(a) enzymatically converting 3-methylcrotonyl-CoA into 3-hydroxy-3-methylbutyryl-CoA; and
(b) further enzymatically converting the thus produced 3-hydroxy-3-methylbutyryl-CoA into 3-hydroxy-3-methylbutyric acid
wherein the enzymatic conversion of 3-hydroxy-3-methylbutyryl-CoA into 3-hydroxy-3-methylbutyric acid according to step (b) is achieved by first converting 3-hydroxy-3-methylbutyryl-CoA into 3-hydroxy-3-methylbutyryl phosphate and then subsequently converting the thus produced 3-hydroxy-3-methylbutyryl phosphate into 3-hydroxy-3-methylbutyric acid.

16 Claims, 22 Drawing Sheets
Specification includes a Sequence Listing.

(56) References Cited

OTHER PUBLICATIONS

Written Opinion and International Search Report dated Nov. 17, 2015 in PCT/EP2015/071185.
International Preliminary Report on Patentability and Written Opinion dated Mar. 30, 2017 and received in PCT/EP2015/071185.

* cited by examiner

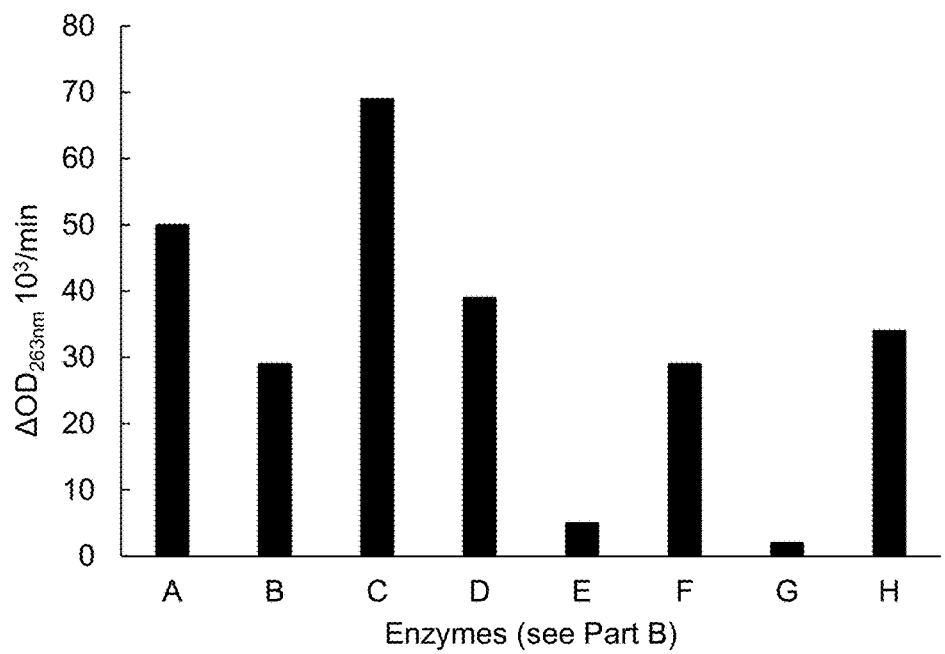

Figure 12A

| | Enzyme | Uniprot accession number |
|---|---|---|
| A | 3-hydroxypropionyl-CoA dehydratase Metallosphaera cuprina (SEQ ID NO : 1) | F4FZ85 |
| B | 3-hydroxypropionyl-CoA dehydratase Sulfolobus tokodaii (SEQ ID NO : 2) | F9VNG3 |
| C | 3-hydroxypropionyl-CoA dehydratase Metallosphaera sedula (SEQ ID NO : 3) | A4YI89 |
| D | 3-Hydroxybutyryl-CoA dehydratase Sulfolobus acidocaldarius (SEQ ID NO : 4) | Q4J8D5 |
| E | 3-hydroxybutyryl-CoA dehydratase Acidianus hospitalis (SEQ ID NO : 5) | F4B9R3 |
| F | 3-hydroxypropionyl-CoA dehydratase Brevibacillus laterosporus (SEQ ID NO : 6) | F7TTZ1 |
| G | 3-hydroxybutyryl-CoA dehydratase Myxococcus xanthus (SEQ ID NO : 7) | Q1D5Y4 |
| H | Enoyl-CoA hydratase Bacillus subtilis (SEQ ID NO : 8) | G4PBC3 |

Figure 12B

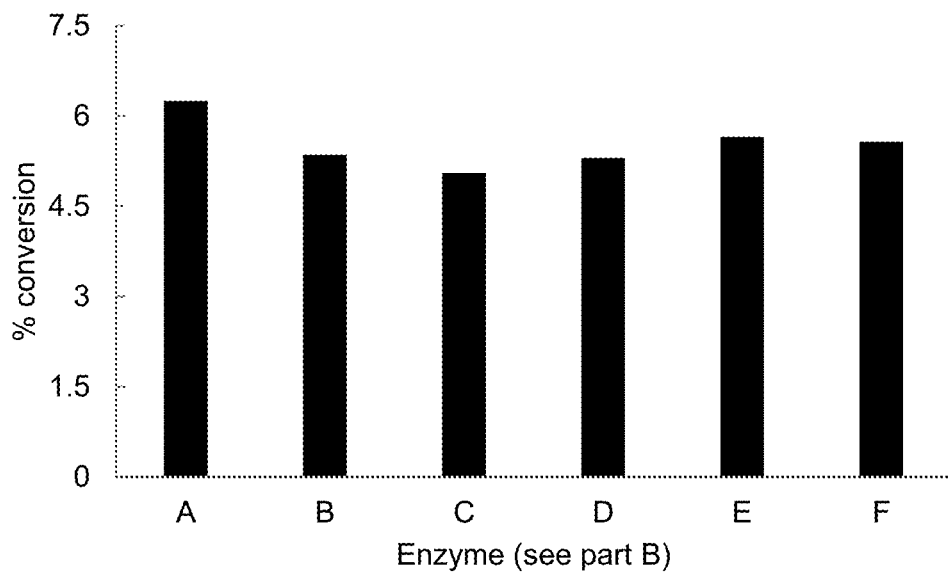

Figure 16A

| | Enzyme | Uniprot Accession number |
|---|---|---|
| A | 3-Hydroxybutyryl-CoA dehydratase Myxococcus xanthus (SEQ ID NO : 7) | Q1D5Y4 |
| B | Methylglutaconyl-CoA hydratase Myxococcus sp (SEQ ID NO : 10) | U2TLJ6 |
| C | 3-Hydroxybutyryl-CoA dehydratase Myxococcus fulvus (SEQ ID NO : 11) | F8CDH2 |
| D | 3-hydroxybutyryl-CoA dehydratase Myxococcus stipitatus (SEQ ID NO : 12) | L7U993 |
| E | 3-Hydroxybutyryl-CoA dehydratase Corallococcus coralloides (SEQ ID NO : 13) | H8N0F4 |
| F | 3-Hydroxybutyryl-CoA dehydratase CoA dehydratase Stigmatella aurantiaca (SEQ ID NO : 14) | Q08YS1 |

Figure 16B

SEQUENCE LISTING

```
<160> NUMBER OF SEQ ID NOS: 31

<210> SEQ ID NO 1
<211> LENGTH: 259
<212> TYPE: PRT
<213> ORGANISM: Metallosphaera cuprina
<220> FEATURE:
<223> OTHER INFORMATION: strain Ar-4

<400> SEQUENCE: 1

Met Glu Tyr Glu Thr Leu Glu Thr Lys Lys Glu Gly Asn Leu Phe Trp
1               5                   10                  15

Ile Thr Leu Asn Arg Pro Asp Lys Leu Asn Ala Leu Asn Ser Lys Leu
            20                  25                  30

Leu Glu Glu Leu Asn Arg Ala Val Ser Glu Gly Glu Ser Asp Pro Glu
        35                  40                  45

Val Arg Val Ile Ile Thr Gly Lys Gly Lys Ala Phe Cys Ala Gly
    50                  55                  60

Ala Asp Ile Thr Gln Phe Asn Gln Leu Ser Pro Thr Asp Ala Trp Arg
65                  70                  75                  80

Phe Ser Lys Arg Gly Arg Glu Val Met Asp Lys Ile Glu Ser Leu Ser
                85                  90                  95

Lys Pro Thr Ile Ala Met Ile Asn Gly Tyr Ala Leu Gly Gly Gly Leu
            100                 105                 110

Glu Leu Ala Leu Ser Cys Asp Ile Arg Ile Ala Ala Glu Glu Ala Gln
        115                 120                 125

Leu Gly Leu Pro Glu Ile Asn Leu Gly Ile Tyr Pro Gly Tyr Gly Gly
    130                 135                 140

Thr Gln Arg Leu Thr Arg Ile Val Gly Lys Gly Arg Ala Leu Glu Ile
145                 150                 155                 160

Met Met Thr Gly Asp Arg Leu Ser Gly Lys Asp Ala Glu Arg Tyr Gly
                165                 170                 175

Leu Val Asn Arg Val Thr Pro Leu Ser Asn Leu Glu Gln Glu Thr Arg
            180                 185                 190

Lys Leu Ala Glu Lys Ile Ala Arg Lys Ser Pro Val Ser Leu Ala Leu
        195                 200                 205

Ile Lys Glu Val Val Asn Lys Gly Leu Asp Ser Pro Leu Ala Ser Gly
    210                 215                 220

Leu Ser Leu Glu Ser Ile Gly Trp Gly Val Ile Phe Ser Thr Glu Asp
225                 230                 235                 240

Lys Lys Glu Gly Val Asn Ala Phe Leu Glu Lys Arg Glu Pro Asn Phe
                245                 250                 255

Lys Gly Lys

<210> SEQ ID NO 2
<211> LENGTH: 257
<212> TYPE: PRT
```

<213> ORGANISM: Sulfolobus tokodaii
<220> FEATURE:
<223> OTHER INFORMATION: strain DSM 16993 / JCM 10545 / NBRC 100140 / 7

<400> SEQUENCE: 2

```
Met Glu Thr Ile Val Ile Lys Lys Glu Thr Pro Ile Gly Trp Ile Tyr
1               5                   10                  15

Leu Asn Arg Pro Asp Arg Leu Asn Ala Ile Asn Gln Gln Met Ile Lys
            20                  25                  30

Glu Leu Arg Gln Gly Ile Asp Glu Met Val Tyr Asp Ser Asp Ile Lys
        35                  40                  45

Val Ile Ile Ile Thr Gly Asn Gly Lys Ala Phe Ser Ala Gly Ala Asp
50                  55                  60

Ile Ser Arg Phe Lys Glu Leu Asn Gly Tyr Thr Ala Trp Gln Phe Ala
65                  70                  75                  80

Lys Ser Gly Arg Glu Leu Met Asp Tyr Ile Glu Asn Ile Ser Lys Pro
                85                  90                  95

Thr Ile Ala Met Val Asn Gly Tyr Ala Leu Gly Gly Gly Leu Glu Leu
            100                 105                 110

Ala Met Ala Cys Asp Ile Arg Ile Ala Ala Glu Glu Ala Gln Leu Gly
        115                 120                 125

Leu Pro Glu Ile Asn Leu Gly Ile Tyr Pro Gly Phe Gly Gly Thr Gln
130                 135                 140

Arg Leu Val Arg Leu Ile Gly Lys Gly Lys Ala Leu Glu Leu Met Leu
145                 150                 155                 160

Thr Gly Asp Arg Ile Ser Ala Lys Glu Ala Lys Ile Gly Leu Val
                165                 170                 175

Asn Lys Val Val Pro Leu Ser Asn Leu Glu Gln Glu Thr Arg Asn Phe
            180                 185                 190

Ala Leu Lys Leu Ala Glu Lys Pro Pro Ile Ser Ile Ala Leu Ile Lys
        195                 200                 205

Leu Leu Val Asn Gln Gly Ile Asp Leu Pro Ile Leu Ala Gly Leu Asn
    210                 215                 220

Met Glu Ser Leu Gly Trp Gly Val Val Phe Ser Thr Glu Asp Glu Lys
225                 230                 235                 240

Glu Gly Val Ser Ala Phe Leu Glu Lys Arg Lys Ala Gln Phe Lys Gly
                245                 250                 255

Lys
```

<210> SEQ ID NO 3
<211> LENGTH: 259
<212> TYPE: PRT
<213> ORGANISM: Metallosphaera sedula
<220> FEATURE:
<223> OTHER INFORMATION: strain ATCC 51363 /DSM 5348

<400> SEQUENCE: 3

```
Met Glu Phe Glu Thr Ile Glu Thr Lys Lys Glu Gly Asn Leu Phe Trp
1               5                   10                  15

Ile Thr Leu Asn Arg Pro Asp Lys Leu Asn Ala Leu Asn Ala Lys Leu
            20                  25                  30

Leu Glu Glu Leu Asp Arg Ala Val Ser Gln Ala Glu Ser Asp Pro Glu
        35                  40                  45

Ile Arg Val Ile Ile Ile Thr Gly Lys Gly Lys Ala Phe Cys Ala Gly
50                  55                  60

Ala Asp Ile Thr Gln Phe Asn Gln Leu Thr Pro Ala Glu Ala Trp Lys
```

-continued

```
                65                  70                  75                  80
        Phe Ser Lys Lys Gly Arg Glu Ile Met Asp Lys Ile Glu Ala Leu Ser
                             85                  90                  95

Lys Pro Thr Ile Ala Met Ile Asn Gly Tyr Ala Leu Gly Gly Gly Leu
                            100                 105                 110

Glu Leu Ala Leu Ala Cys Asp Ile Arg Ile Ala Ala Glu Glu Ala Gln
                            115                 120                 125

Leu Gly Leu Pro Glu Ile Asn Leu Gly Ile Tyr Pro Gly Tyr Gly Gly
                130                 135                 140

Thr Gln Arg Leu Thr Arg Val Ile Gly Lys Gly Arg Ala Leu Glu Met
        145                 150                 155                 160

Met Met Thr Gly Asp Arg Ile Pro Gly Lys Asp Ala Glu Lys Tyr Gly
                            165                 170                 175

Leu Val Asn Arg Val Val Pro Leu Ala Asn Leu Glu Gln Glu Thr Arg
                            180                 185                 190

Lys Leu Ala Glu Lys Ile Ala Lys Lys Ser Pro Ile Ser Leu Ala Leu
                            195                 200                 205

Ile Lys Glu Val Val Asn Arg Gly Leu Asp Ser Pro Leu Leu Ser Gly
                210                 215                 220

Leu Ala Leu Glu Ser Val Gly Trp Gly Val Val Phe Ser Thr Glu Asp
        225                 230                 235                 240

Lys Lys Glu Gly Val Ser Ala Phe Leu Glu Lys Arg Glu Pro Thr Phe
                            245                 250                 255

Lys Gly Lys

<210> SEQ ID NO 4
<211> LENGTH: 257
<212> TYPE: PRT
<213> ORGANISM: Sulfolobus acidocaldarius
<220> FEATURE:
<223> OTHER INFORMATION: strain ATCC 33909 / DSM 639 / JCM 8929 / NBRC
      15157 / NCIMB 11770

<400> SEQUENCE: 4

Met Glu Thr Ile Ile Val Lys Asn Glu Pro Pro Phe Leu Arg Ile Thr
        1               5                   10                  15

Leu Asn Arg Pro Asp Arg Leu Asn Ala Ile Asn Lys Lys Met Ile Glu
                            20                  25                  30

Glu Ile Arg Thr Val Leu Glu Glu Thr Val Lys Asp Glu Lys Val Arg
                        35                  40                  45

Val Ile Ile Phe Thr Gly Asn Gly Arg Ala Phe Ser Ala Gly Ala Asp
                50                  55                  60

Ile Ser Gln Phe Lys Glu Leu Glu Gly Leu Thr Ala Trp Gln Phe Ala
        65                  70                  75                  80

Met Lys Gly Arg Glu Leu Met Asp Tyr Ile Glu Asn Tyr Pro Lys Pro
                            85                  90                  95

Thr Ile Ala Met Ile Asn Gly Tyr Ala Leu Gly Gly Gly Leu Glu Leu
                            100                 105                 110

Ala Leu Ala Cys Asp Ile Arg Ile Ala Ser Asp Glu Ala Gln Leu Gly
                            115                 120                 125

Leu Pro Glu Ile Thr Leu Gly Ile Tyr Pro Gly Phe Gly Gly Thr Gln
                130                 135                 140

Arg Leu Leu Lys Leu Val Gly Lys Ser Arg Thr Leu Glu Met Ile Met
        145                 150                 155                 160

Leu Gly Glu Arg Ile Ser Ala Lys Asp Ala Glu Arg Ile Gly Leu Val
```

```
                         165                 170                 175
Asn Arg Val Val Pro Ser Asn Asp Leu Glu Lys Glu Thr Leu Asn Leu
            180                 185                 190

Ala Ser Lys Leu Ala Glu Arg Pro Leu Ala Ile Gln Leu Ser Lys
        195                 200                 205

Leu Ile Val Asn Gln Gly Met Asn Ser Pro Ile Thr Val Gly Leu Asn
210                 215                 220

Met Glu Ser Leu Gly Trp Gly Val Ile Phe Thr Thr Lys Asp Ser Lys
225                 230                 235                 240

Glu Gly Val Asn Ala Phe Leu Glu Lys Arg Lys Pro Asn Phe Lys Gly
                245                 250                 255

Glu
```

<210> SEQ ID NO 5
<211> LENGTH: 257
<212> TYPE: PRT
<213> ORGANISM: Acidianus hospitalis
<220> FEATURE:
<223> OTHER INFORMATION: strain W1

<400> SEQUENCE: 5

```
Met Glu Thr Val Glu Thr Lys Ile Glu Asn Gly Ile Gly Trp Ile Ile
1               5                   10                  15

Leu Asn Arg Pro Asp Lys Leu Asn Ala Ile Asn Leu Lys Met Leu Glu
            20                  25                  30

Glu Leu Glu Glu Val Thr Lys Asn Phe Glu Glu Asn Asn Asp Val Lys
        35                  40                  45

Ile Ile Ile Phe Thr Gly Asn Gly Lys Ala Phe Ser Ala Gly Ala Asp
50                  55                  60

Ile Ser Gln Phe Lys Glu Leu Asn Ser Ile Ser Ala Trp Asn Phe Ala
65                  70                  75                  80

Lys Lys Gly Arg Arg Val Met Asp Tyr Ile Glu Ser Val Ser Lys Pro
                85                  90                  95

Thr Ile Ala Met Ile Asn Gly Tyr Ala Leu Gly Gly Gly Leu Glu Leu
            100                 105                 110

Ala Leu Ala Cys Asp Phe Arg Ile Ala Ala Glu Glu Ala Ser Leu Gly
        115                 120                 125

Leu Pro Glu Ile Asn Leu Gly Ile Tyr Pro Gly Phe Gly Gly Thr Gln
    130                 135                 140

Arg Leu Val Arg Ala Ile Gly Lys Ala Lys Ala Met Glu Leu Met Met
145                 150                 155                 160

Thr Gly Asp Arg Ile Ser Ala Lys Glu Ala Glu Arg Ile Gly Leu Val
                165                 170                 175

Asn Lys Val Val Ser Leu Ser Ser Leu Lys Glu Glu Thr Ile Lys Phe
            180                 185                 190

Ala Gly Lys Leu Met Glu Lys Ser Pro Ile Ala Leu Ala Ile Leu Lys
        195                 200                 205

His Ile Ile Leu Tyr Gly Asn Asp Ser Pro Leu Leu Asp Gly Leu Asn
    210                 215                 220

Met Glu Ser Leu Gly Trp Gly Val Ala Phe Ser Thr Glu Asp Glu Lys
225                 230                 235                 240

Glu Gly Val Ser Ala Phe Leu Glu Lys Arg Lys Ala Val Phe Lys Gly
                245                 250                 255

Lys
```

<210> SEQ ID NO 6
<211> LENGTH: 258
<212> TYPE: PRT
<213> ORGANISM: Brevibacillus laterosporus
<220> FEATURE:
<223> OTHER INFORMATION: LMG 15441

<400> SEQUENCE: 6

```
Met Ser Tyr Pro Asn Leu Thr Leu Val Thr Glu Gly Thr Ile Ala Ile
1               5                   10                  15

Val Thr Ile Asn His Pro Pro Ala Asn Ala Leu Asn Gln Ala Thr Leu
            20                  25                  30

Thr Ser Leu Ala Gln Ala Leu Asp Asp Leu Gln Asn Asp Gln Ile
        35                  40                  45

Arg Ala Ile Val Ile Thr Gly Glu Gly Arg Phe Phe Ile Ala Gly Ala
    50                  55                  60

Asp Ile Lys Glu Phe Thr Ala Leu Ala Glu Gln Ser Pro Gln Gln Val
65                  70                  75                  80

Ala Glu Arg Gly Gln Gln Leu Phe Leu Arg Met Glu Thr Phe Ser Lys
                85                  90                  95

Pro Ile Ile Ala Ala Ile Asn Gly Ala Cys Leu Gly Gly Gly Leu Glu
            100                 105                 110

Leu Ala Met Ala Cys His Ile Arg Tyr Val Ala Lys Glu Ala Lys Leu
        115                 120                 125

Gly Leu Pro Glu Leu Asn Leu Gly Leu Ile Pro Gly Tyr Gly Gly Thr
    130                 135                 140

Gln Arg Leu Pro Arg Leu Ile Gly Arg Gly Lys Ala Thr Gln Leu Ile
145                 150                 155                 160

Leu Thr Ser Asp Met Ile Asp Gly Glu Glu Ala Leu Ala Ile Gly Leu
                165                 170                 175

Ala Glu Ala Val Tyr Pro Val Glu Gln Leu Leu Glu Glu Ser Lys Lys
            180                 185                 190

Leu Ala Arg Lys Ile Ser Glu Lys Gly Ala Ile Ser Val Lys Tyr Ala
        195                 200                 205

Leu Asp Ala Ile His Ser Gly Val Glu Leu Gly Leu Ser Ala Gly Met
    210                 215                 220

Lys Arg Glu Ala Glu Leu Phe Gly Gln Val Phe Thr Thr Glu Asp Met
225                 230                 235                 240

Lys Glu Gly Val Thr Ala Phe Leu Glu Lys Arg Lys Pro Gln Phe Ser
                245                 250                 255

Asn Arg
```

<210> SEQ ID NO 7
<211> LENGTH: 258
<212> TYPE: PRT
<213> ORGANISM: Myxococcus xanthus
<220> FEATURE:
<223> OTHER INFORMATION: strain DK 1622

<400> SEQUENCE: 7

```
Met Pro Glu Phe Lys Val Asp Ala Arg Gly Pro Ile Glu Ile Trp Thr
1               5                   10                  15

Ile Asp Gly Glu Ser Arg Arg Asn Ala Ile Ser Arg Ala Met Leu Lys
            20                  25                  30

Glu Leu Gly Glu Leu Val Thr Arg Val Ser Ser Arg Asp Val Arg
        35                  40                  45
```

```
Ala Val Val Ile Thr Gly Ala Gly Asp Lys Ala Phe Cys Ala Gly Ala
    50                  55                  60

Asp Leu Lys Glu Arg Ala Thr Met Ala Glu Asp Glu Val Arg Ala Phe
 65                  70                  75                  80

Leu Asp Gly Leu Arg Arg Thr Phe Arg Ala Ile Glu Lys Ser Asp Cys
                 85                  90                  95

Val Phe Ile Ala Ala Ile Asn Gly Ala Ala Leu Gly Gly Gly Thr Glu
            100                 105                 110

Leu Ala Leu Ala Cys Asp Leu Arg Val Ala Ala Pro Ala Ala Glu Leu
        115                 120                 125

Gly Leu Thr Glu Val Lys Leu Gly Ile Ile Pro Gly Gly Gly Gly Thr
    130                 135                 140

Gln Arg Leu Ala Arg Leu Val Gly Pro Gly Arg Ala Lys Asp Leu Ile
145                 150                 155                 160

Leu Thr Ala Arg Arg Ile Asn Ala Ala Glu Ala Phe Ser Val Gly Leu
                165                 170                 175

Ala Asn Arg Leu Ala Pro Glu Gly His Leu Leu Ala Val Ala Tyr Gly
            180                 185                 190

Leu Ala Glu Ser Val Val Glu Asn Ala Pro Ile Ala Val Ala Thr Ala
        195                 200                 205

Lys His Ala Ile Asp Glu Gly Thr Gly Leu Glu Leu Asp Asp Ala Leu
    210                 215                 220

Ala Leu Glu Leu Arg Lys Tyr Glu Glu Ile Leu Lys Thr Glu Asp Arg
225                 230                 235                 240

Leu Glu Gly Leu Arg Ala Phe Ala Glu Lys Arg Ala Pro Val Tyr Lys
                245                 250                 255

Gly Arg

<210> SEQ ID NO 8
<211> LENGTH: 258
<212> TYPE: PRT
<213> ORGANISM: Bacillus subtilis
<220> FEATURE:
<223> OTHER INFORMATION: subsp. subtilis str. RO-NN-1

<400> SEQUENCE: 8

Met Asn Ala Ile Ser Leu Ala Val Asp Gln Phe Val Ala Val Leu Thr
  1               5                  10                  15

Ile His Asn Pro Pro Ala Asn Ala Leu Ser Ser Arg Ile Leu Glu Glu
             20                  25                  30

Leu Ser Ser Cys Leu Asp Gln Cys Glu Thr Asp Ala Gly Val Arg Ser
         35                  40                  45

Ile Ile Ile His Gly Glu Gly Arg Phe Phe Ser Ala Gly Ala Asp Ile
     50                  55                  60

Lys Glu Phe Thr Ser Leu Lys Gly Asn Glu Asp Phe Ser Leu Leu Ala
 65                  70                  75                  80

Glu Arg Gly Gln Gln Leu Met Glu Arg Ile Glu Ser Phe Pro Lys Pro
                 85                  90                  95

Ile Ile Ala Ala Ile His Gly Ala Ala Leu Gly Gly Gly Leu Glu Leu
            100                 105                 110

Ala Met Ala Cys His Ile Arg Ile Ala Ala Asp Asp Ala Lys Leu Gly
        115                 120                 125

Leu Pro Glu Leu Asn Leu Gly Ile Ile Pro Gly Phe Ala Gly Thr Gln
    130                 135                 140

Arg Leu Pro Arg Tyr Val Gly Thr Ala Lys Ala Leu Glu Leu Ile Gly
```

```
145                 150                 155                 160
Ser Gly Glu Pro Ile Ser Gly Lys Glu Ala Leu Asp Leu Gly Leu Val
                165                 170                 175

Ser Ile Gly Ala Lys Asp Glu Ala Glu Val Ile Glu Lys Ala Lys Ala
            180                 185                 190

Leu Ala Ala Lys Phe Ala Glu Lys Ser Pro Gln Thr Leu Ala Ser Leu
        195                 200                 205

Leu Glu Leu Leu Tyr Ser Asn Lys Val Tyr Ser Tyr Glu Gly Ser Leu
    210                 215                 220

Lys Leu Glu Ala Lys Arg Phe Gly Glu Ala Phe Glu Ser Glu Asp Ala
225                 230                 235                 240

Lys Glu Gly Ile Gln Ala Phe Leu Glu Lys Arg Lys Pro Gln Phe Lys
                245                 250                 255

Gly Glu

<210> SEQ ID NO 9
<211> LENGTH: 263
<212> TYPE: PRT
<213> ORGANISM: Bacillus anthracis

<400> SEQUENCE: 9

Met Lys Asn Glu Arg Leu Val Ile Cys Ser Lys Lys Gly Ser Ser Ala
1               5                   10                  15

Val Ile Thr Ile Gln Asn Pro Pro Val Asn Ala Leu Ser Leu Glu Val
            20                  25                  30

Val Gln Gln Leu Ile Asn Val Leu Glu Glu Ile Glu Met Asp Asp Asp
        35                  40                  45

Ile Ala Val Val Ile Thr Gly Ile Gly Gly Lys Ala Phe Val Ala
    50                  55                  60

Gly Gly Asp Ile Lys Glu Phe Pro Gly Trp Ile Gly Lys Gly Glu Lys
65                  70                  75                  80

Tyr Ala Glu Met Lys Ser Ile Glu Leu Gln Arg Pro Leu Asn Gln Leu
                85                  90                  95

Glu Asn Leu Ser Lys Pro Thr Ile Ala Ala Ile Asn Gly Leu Ala Leu
            100                 105                 110

Gly Gly Gly Cys Glu Leu Ala Leu Ala Cys Asp Leu Arg Val Ile Glu
        115                 120                 125

Glu Gln Ala Leu Ile Gly Leu Pro Glu Ile Thr Leu Gly Leu Phe Pro
    130                 135                 140

Gly Ala Gly Gly Thr Gln Arg Leu Pro Arg Leu Ile Gly Glu Gly Lys
145                 150                 155                 160

Ala Lys Glu Met Met Phe Thr Gly Lys Pro Ile Thr Ala Lys Glu Ala
                165                 170                 175

Lys Glu Ile Asn Leu Val Asn Tyr Ile Thr Ser Arg Gly Glu Ala Leu
            180                 185                 190

Asn Lys Ala Lys Glu Ile Ala Lys Asp Ile Ser Glu Phe Ser Leu Pro
        195                 200                 205

Ala Leu Ser Tyr Met Lys Leu Ala Ile Arg Glu Gly Leu Ala Val Pro
    210                 215                 220

Leu Gln Glu Gly Leu Gln Ile Glu Ala Arg Tyr Phe Gly Lys Val Phe
225                 230                 235                 240

Gln Thr Glu Asp Val Lys Glu Gly Val Lys Ala Phe Ile Glu Lys Arg
                245                 250                 255

Val Pro Arg Phe Thr Asn Lys
```

-continued

```
              260

<210> SEQ ID NO 10
<211> LENGTH: 258
<212> TYPE: PRT
<213> ORGANISM: Myxococcus sp.

<400> SEQUENCE: 10

Met Pro Glu Phe Lys Val Asp Ala Arg Gly Pro Ile Glu Ile Trp Thr
1               5                   10                  15

Ile Asp Gly Glu Ser Arg Arg Asn Ala Ile Ser Arg Ala Met Leu Gln
            20                  25                  30

Glu Leu Gly Glu Met Val Thr Arg Val Ser Ser Arg Glu Val Arg
        35                  40                  45

Ala Val Val Ile Thr Gly Ala Gly Asp Lys Ala Phe Cys Ala Gly Ala
    50                  55                  60

Asp Leu Lys Glu Arg Ala Thr Met Ala Glu Asp Val Arg Ala Phe
65                  70                  75                  80

Leu Asp Gly Leu Arg Arg Thr Phe Arg Ala Leu Glu Lys Ser Asp Cys
                85                  90                  95

Val Phe Ile Ala Ala Ile Asn Gly Ala Ala Phe Gly Gly Gly Thr Glu
            100                 105                 110

Leu Ala Leu Ala Cys Asp Leu Arg Val Ala Ala Pro Ala Ala Glu Leu
        115                 120                 125

Gly Leu Thr Glu Val Lys Leu Gly Ile Ile Pro Gly Gly Gly Thr
    130                 135                 140

Gln Arg Leu Thr Arg Leu Val Gly Pro Gly Arg Ala Lys Asp Leu Ile
145                 150                 155                 160

Leu Thr Ala Arg Arg Ile Asn Ala Ala Glu Ala Phe Ser Val Gly Leu
                165                 170                 175

Val Asn Arg Leu Ala Pro Glu Gly His Leu Leu Ala Val Ala Tyr Gly
            180                 185                 190

Leu Ala Glu Ser Val Val Glu Asn Ala Pro Ile Ala Val Ala Thr Ala
        195                 200                 205

Lys His Ala Ile Asp Glu Gly Thr Gly Leu Glu Leu Asp Asp Ala Leu
    210                 215                 220

Ala Leu Glu Leu Arg Lys Tyr Glu Gly Ile Leu Lys Thr Glu Asp Arg
225                 230                 235                 240

Leu Glu Gly Leu Arg Ala Phe Ala Glu Lys Arg Ala Pro Val Tyr Lys
                245                 250                 255

Gly Arg

<210> SEQ ID NO 11
<211> LENGTH: 258
<212> TYPE: PRT
<213> ORGANISM: Myxococcus fulvus
<220> FEATURE:
<223> OTHER INFORMATION: strain ATCC BAA-855 /HW-1

<400> SEQUENCE: 11

Met Pro Glu Phe Lys Val Asp Ala Arg Gly Ala Ile Glu Ile Trp Thr
1               5                   10                  15

Ile Asp Gly Glu Ser Arg Arg Asn Ala Ile Ser Arg Ala Met Leu Lys
            20                  25                  30

Glu Leu Gly Glu Leu Val Thr Arg Val Ser Ser Arg Glu Val Arg
        35                  40                  45
```

-continued

```
Ala Val Val Ile Thr Gly Ala Gly Asp Lys Ala Phe Cys Ala Gly Ala
             50                  55                  60

Asp Leu Lys Glu Arg Ala Thr Met Ser Glu Asp Glu Val Arg Ala Phe
 65                  70                  75                  80

Leu Asp Gly Leu Arg Arg Thr Phe Arg Ala Ile Glu Gln Ser Asp Cys
                 85                  90                  95

Val Phe Ile Ala Ala Ile Asn Gly Ala Ala Phe Gly Gly Gly Thr Glu
            100                 105                 110

Leu Ser Leu Ala Cys Asp Leu Arg Val Ala Ala Pro Ala Ala Glu Leu
            115                 120                 125

Gly Leu Thr Glu Val Lys Leu Gly Ile Ile Pro Gly Gly Gly Gly Thr
130                 135                 140

Gln Arg Leu Ala Arg Leu Val Gly Pro Gly Arg Ala Lys Asp Leu Ile
145                 150                 155                 160

Leu Thr Ala Arg Arg Ile Asn Ala Ala Glu Ala Phe Ser Val Gly Leu
                165                 170                 175

Val Asn Arg Leu Ala Pro Glu Gly His Leu Leu Ala Val Ala Tyr Gly
            180                 185                 190

Leu Ala Glu Ser Val Val Glu Asn Ala Pro Ile Ala Val Ala Thr Ala
            195                 200                 205

Lys His Ala Ile Asp Glu Gly Thr Gly Leu Ala Leu Asp Asp Ala Leu
            210                 215                 220

Ala Leu Glu Leu Arg Lys Tyr Glu Glu Ile Leu Lys Thr Glu Asp Arg
225                 230                 235                 240

Leu Glu Gly Leu Arg Ala Phe Ala Glu Lys Arg Ala Pro Val Tyr Lys
                245                 250                 255

Gly Arg

<210> SEQ ID NO 12
<211> LENGTH: 258
<212> TYPE: PRT
<213> ORGANISM: Myxococcus stipitatus
<220> FEATURE:
<223> OTHER INFORMATION: strain DSM 14675 /JCM 12634/Mx s8

<400> SEQUENCE: 12

Met Pro Glu Phe Lys Val Asp Ala Arg Gly Ala Ile Glu Ile Trp Thr
 1               5                  10                  15

Ile Asp Gly Glu Gly Arg Arg Asn Ala Ile Ser Arg Ala Met Leu Gln
                 20                  25                  30

Glu Leu Gly Ala Leu Val Glu Arg Val Ser Ser Gly His Gln Val Arg
             35                  40                  45

Ala Val Val Ile Thr Gly Ala Gly Asp Lys Ala Phe Cys Ala Gly Ala
             50                  55                  60

Asp Leu Lys Glu Arg Ala Gly Met Ser Glu Ser Glu Val Arg Ala Phe
 65                  70                  75                  80

Leu Asp Gly Leu Arg Arg Thr Phe Arg Ala Ile Glu Lys Ser Asp Cys
                 85                  90                  95

Val Phe Ile Ala Ala Val Asn Gly Ala Ala Phe Gly Gly Gly Thr Glu
            100                 105                 110

Leu Ala Leu Ala Cys Asp Leu Arg Val Ala Ala Pro Ala Ala Glu Leu
            115                 120                 125

Gly Leu Thr Glu Val Lys Leu Gly Ile Ile Pro Gly Gly Gly Gly Thr
130                 135                 140

Gln Arg Leu Thr Arg Leu Val Gly Pro Gly Arg Ala Lys Asp Leu Ile
```

```
            145                 150                 155                 160
    Leu Thr Ala Arg Arg Leu Asn Ala Ala Glu Ala Phe Ala Met Gly Leu
                    165                 170                 175

Val Asn Arg Leu Ala Pro Glu Gly His Leu Leu Glu Val Ala His Thr
                    180                 185                 190

Leu Ala Glu Ser Val Val Glu Asn Ala Pro Ile Ala Val Ala Thr Ala
                    195                 200                 205

Lys His Ala Ile Asp Glu Gly Thr Gly Leu Glu Leu Asp Asp Ala Leu
                    210                 215                 220

Ala Leu Glu Leu Arg Lys Tyr Glu Glu Ile Leu Lys Thr Glu Asp Arg
    225                 230                 235                 240

Leu Glu Gly Leu Arg Ala Phe Ala Glu Lys Arg Pro Pro Val Tyr Lys
                    245                 250                 255

Gly Arg

<210> SEQ ID NO 13
    <211> LENGTH: 258
    <212> TYPE: PRT
    <213> ORGANISM: Corallococcus coralloides
    <220> FEATURE:
    <223> OTHER INFORMATION: strain ATCC 25202 / DSM 2259 / NBRC 100086 / M2

<400> SEQUENCE: 13

Met Pro Glu Phe Lys Val Glu Ala Arg Gly Ala Ile Glu Ile Trp Thr
    1               5                   10                  15

Ile Asp Gly Glu Ser Arg Arg Asn Ala Ile Ser Arg Ala Met His Gln
                    20                  25                  30

Glu Leu Asp Ala Leu Val Ser Arg Val Ser Ser Gly Arg Ala Val Arg
                    35                  40                  45

Ala Val Ile Leu Thr Gly Ala Gly Asp Lys Ala Phe Cys Ala Gly Ala
                    50                  55                  60

Asp Leu Lys Glu Arg Thr Thr Met Ser Glu Asp Glu Val Arg Ala Phe
    65                  70                  75                  80

Leu Asn Gly Leu Arg Val Thr Leu Arg Ser Ile Glu Lys Ser Asp Cys
                    85                  90                  95

Val Phe Ile Ala Ala Ile Asn Gly Ala Ala Phe Gly Gly Gly Thr Glu
                    100                 105                 110

Leu Ala Leu Ala Cys Asp Leu Arg Val Ala Ser Pro Ala Thr Glu Met
                    115                 120                 125

Gly Leu Thr Glu Val Lys Leu Gly Ile Ile Pro Gly Gly Gly Gly Thr
                    130                 135                 140

Gln Arg Leu Ala Arg Leu Ile Gly Pro Gly Arg Ala Lys Asp Leu Ile
    145                 150                 155                 160

Leu Thr Ala Arg Arg Val Asn Ala Ala Glu Ala Phe Ser Ile Gly Leu
                    165                 170                 175

Val Asn Arg Leu Ala Pro Glu Gly His Leu Leu Glu Val Ala Phe Gln
                    180                 185                 190

Leu Ala Glu Ala Val Val Glu Asn Ala Pro Val Ala Val Ala Thr Ala
                    195                 200                 205

Lys His Ala Ile Asp Glu Gly Thr Gly Leu Glu Leu Asp Asp Ala Leu
                    210                 215                 220

Ala Leu Glu Leu Lys Lys Tyr Glu Glu Val Leu Lys Thr Glu Asp Arg
    225                 230                 235                 240

Leu Glu Gly Leu Arg Ala Phe Ala Glu Lys Arg Pro Pro Val Tyr Lys
                    245                 250                 255
```

Gly Arg

<210> SEQ ID NO 14
<211> LENGTH: 258
<212> TYPE: PRT
<213> ORGANISM: Stigmatella aurantiaca
<220> FEATURE:
<223> OTHER INFORMATION: strain DW4/3-1

<400> SEQUENCE: 14

Met Pro Glu Phe Lys Val Asp Ala Arg Gly Ala Ile Glu Ile Trp Thr
1               5                   10                  15

Ile Asp Gly Ala Asp Arg Arg Asn Ala Ile Ser Arg Ala Met Leu Gln
            20                  25                  30

Glu Leu Ser Gly Met Val Thr Arg Val Ser Thr Gly Arg Ala Val Arg
        35                  40                  45

Ala Val Ile Ile Thr Gly Ala Gly Asp Lys Ala Phe Cys Ala Gly Ala
    50                  55                  60

Asp Leu Lys Glu Arg Ala Gly Met Ser Glu Ala Val Arg Ala Phe
65                  70                  75                  80

Leu Asp Gly Leu Arg Gln Thr Leu Arg Ala Ile Glu Lys Ser Asp Cys
                85                  90                  95

Val Phe Ile Ala Ala Ile Asn Gly Ala Ala Leu Gly Gly Gly Thr Glu
            100                 105                 110

Leu Ser Leu Ala Cys Asp Leu Arg Val Ala Val Pro Ala Thr Glu Leu
        115                 120                 125

Gly Leu Thr Glu Val Arg Leu Gly Ile Ile Pro Gly Gly Gly Gly Thr
    130                 135                 140

Gln Arg Leu Ser Arg Leu Val Gly Pro Gly Arg Ala Lys Asp Leu Ile
145                 150                 155                 160

Leu Thr Gly Arg Arg Ile Asn Ala Ala Glu Ala Phe Ser Ile Gly Leu
                165                 170                 175

Val Asn Arg Leu Ala Pro Glu Gly His Leu Val Glu Thr Ser Phe Ser
            180                 185                 190

Leu Ala Glu Ala Ile Val Ala Asn Ala Pro Ile Ala Val Ser Thr Ala
        195                 200                 205

Lys His Ala Ile Asp Glu Gly Thr Gly Leu Glu Leu Asp Asp Ala Leu
    210                 215                 220

Ala Leu Glu Leu Arg Lys Tyr Glu Asp Ile Leu Gln Thr Glu Asp Arg
225                 230                 235                 240

Leu Glu Gly Leu Arg Ser Phe Ala Glu Lys Arg Pro Pro Val Tyr Lys
                245                 250                 255

Gly Arg

<210> SEQ ID NO 15
<211> LENGTH: 392
<212> TYPE: PRT
<213> ORGANISM: Clostridium acetobutylicum
<220> FEATURE:
<223> OTHER INFORMATION: strain ATCC 824 / DSM 792 / JCM 1419 / LMG 5710
      / VKM B-1787

<400> SEQUENCE: 15

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
         35                  40                  45

Asn Glu Val Ile Leu Gly Asn Val Leu Gln Ala Gly Leu Gly Gln Asn
 50                  55                  60

Pro Ala Arg Gln Ala Ser Phe Lys Ala Gly Leu Pro Val Glu Ile Pro
 65                  70                  75                  80

Ala Met Thr Ile Asn Lys Val Cys Gly Ser Gly Leu Arg Thr Val Ser
                 85                  90                  95

Leu Ala Ala Gln Ile Ile Lys Ala Gly Asp Ala Asp Val Ile Ile Ala
                100                 105                 110

Gly Gly Met Glu Asn Met Ser Arg Ala Pro Tyr Leu Ala Asn Asn Ala
            115                 120                 125

Arg Trp Gly Tyr Arg Met Gly Asn Ala Lys Phe Val Asp Glu Met Ile
        130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
                180                 185                 190

Gly Gln Phe Lys Asp Glu Ile Val Pro Val Ile Lys Gly Arg Lys
            195                 200                 205

Gly Glu Thr Val Val Asp Thr Asp Glu His Pro Arg Phe Gly Ser Thr
        210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
                260                 265                 270

Ala Lys Ile Val Ser Tyr Gly Ser Ala Gly Val Asp Pro Ala Ile Met
            275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
                340                 345                 350

Ser Gly Ala Arg Ile Leu Val Thr Leu Val His Ala Met Gln Lys Arg
            355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 16
<211> LENGTH: 447
<212> TYPE: PRT
<213> ORGANISM: Schizosaccharomyces pombe
<220> FEATURE:
<223> OTHER INFORMATION: strain 972 / ATCC 24843

<400> SEQUENCE: 16

```
Met Ser Phe Asp Arg Lys Asp Ile Gly Ile Lys Gly Leu Val Leu Tyr
1               5                   10                  15

Thr Pro Asn Gln Tyr Val Glu Gln Ala Ala Leu Glu Ala His Asp Gly
            20                  25                  30

Val Ser Thr Gly Lys Tyr Thr Ile Gly Leu Gly Leu Thr Lys Met Ala
        35                  40                  45

Phe Val Asp Asp Arg Glu Asp Ile Tyr Ser Phe Gly Leu Thr Ala Leu
    50                  55                  60

Ser Gln Leu Ile Lys Arg Tyr Gln Ile Asp Ile Ser Lys Ile Gly Arg
65              70                  75                  80

Leu Glu Val Gly Thr Glu Thr Ile Ile Asp Lys Ser Lys Ser Val Lys
                85                  90                  95

Ser Val Leu Met Gln Leu Phe Gly Asp Asn His Asn Val Glu Gly Ile
            100                 105                 110

Asp Cys Val Asn Ala Cys Tyr Gly Gly Val Asn Ala Leu Phe Asn Thr
        115                 120                 125

Ile Asp Trp Ile Glu Ser Ser Ala Trp Asp Gly Arg Asp Gly Ile Val
    130                 135                 140

Val Ala Gly Asp Ile Ala Leu Tyr Ala Lys Gly Asn Ala Arg Pro Thr
145                 150                 155                 160

Gly Gly Ala Gly Cys Val Ala Leu Leu Val Gly Pro Asn Ala Pro Ile
                165                 170                 175

Val Phe Glu Pro Gly Leu Arg Gly Thr Tyr Met Gln His Ala Tyr Asp
            180                 185                 190

Phe Tyr Lys Pro Asp Leu Thr Ser Glu Tyr Pro Tyr Val Asp Gly His
        195                 200                 205

Phe Ser Leu Glu Cys Tyr Val Lys Ala Leu Asp Gly Ala Tyr Ala Asn
    210                 215                 220

Tyr Asn Val Arg Asp Val Ala Lys Asn Gly Lys Ser Gln Gly Leu Gly
225                 230                 235                 240

Leu Asp Arg Phe Asp Tyr Cys Ile Phe His Ala Pro Thr Cys Lys Gln
                245                 250                 255

Val Gln Lys Ala Tyr Ala Arg Leu Leu Tyr Thr Asp Ser Ala Ala Glu
            260                 265                 270

Pro Ser Asn Pro Glu Leu Glu Gly Val Arg Glu Leu Leu Ser Thr Leu
        275                 280                 285

Asp Ala Lys Lys Ser Leu Thr Asp Lys Ala Leu Glu Lys Gly Leu Met
    290                 295                 300

Ala Ile Thr Lys Glu Arg Phe Asn Lys Arg Val Ser Pro Ser Val Tyr
305                 310                 315                 320

Ala Pro Thr Asn Cys Gly Asn Met Tyr Thr Ala Ser Ile Phe Ser Cys
                325                 330                 335

Leu Thr Ala Leu Leu Ser Arg Val Pro Ala Asp Glu Leu Lys Gly Lys
            340                 345                 350

Arg Val Gly Ala Tyr Ser Tyr Gly Ser Gly Leu Ala Ala Ser Phe Phe
        355                 360                 365

Ser Phe Val Val Lys Gly Asp Val Ser Glu Ile Ala Lys Lys Thr Asn
    370                 375                 380

Leu Val Asn Asp Leu Asp Asn Arg His Cys Leu Thr Pro Thr Gln Tyr
385                 390                 395                 400

Glu Glu Ala Ile Glu Leu Arg His Gln Ala His Leu Lys Lys Asn Phe
                405                 410                 415
```

Thr Pro Lys Gly Ser Ile Glu Arg Leu Arg Ser Gly Thr Tyr Tyr Leu
            420                 425                 430

Thr Gly Ile Asp Asp Met Phe Arg Arg Ser Tyr Ser Val Lys Pro
            435                 440                 445

<210> SEQ ID NO 17
<211> LENGTH: 265
<212> TYPE: PRT
<213> ORGANISM: Myxococcus xanthus
<220> FEATURE:
<223> OTHER INFORMATION: strain DK 1622

<400> SEQUENCE: 17

Met Lys Thr Ala Arg Trp Cys Ser Leu Glu Glu Ala Val Ala Ser Ile
1               5                   10                  15

Pro Asp Gly Ala Ser Leu Ala Thr Gly Gly Phe Met Leu Gly Arg Ala
            20                  25                  30

Pro Met Ala Leu Val Met Glu Leu Ile Ala Gln Gly Lys Arg Asp Leu
        35                  40                  45

Gly Leu Ile Ser Leu Pro Asn Pro Leu Pro Ala Glu Phe Leu Val Ala
    50                  55                  60

Gly Gly Cys Leu Ala Arg Leu Glu Ile Ala Phe Gly Ala Leu Ser Leu
65                  70                  75                  80

Gln Gly Arg Val Arg Pro Met Pro Cys Leu Lys Arg Ala Met Glu Gln
                85                  90                  95

Gly Thr Leu Ala Trp Arg Glu His Asp Gly Tyr Arg Val Val Gln Arg
            100                 105                 110

Leu Arg Ala Ala Ser Met Gly Leu Pro Phe Ile Pro Ala Pro Asp Ala
        115                 120                 125

Asp Val Ser Gly Leu Ala Arg Thr Glu Pro Pro Thr Val Glu Asp
    130                 135                 140

Pro Phe Thr Gly Leu Arg Val Ala Val Glu Pro Ala Phe Tyr Pro Asp
145                 150                 155                 160

Val Ala Leu Leu His Ala Arg Ala Ala Asp Glu Arg Gly Asn Leu Tyr
                165                 170                 175

Met Glu Asp Pro Thr Thr Asp Leu Leu Val Ala Gly Ala Ala Lys Arg
            180                 185                 190

Val Ile Ala Thr Val Glu Glu Arg Val Ala Lys Leu Pro Arg Ala Thr
        195                 200                 205

Leu Pro Gly Phe Gln Val Asp Arg Ile Val Leu Ala Pro Gly Gly Ala
    210                 215                 220

Leu Pro Thr Gly Cys Ala Gly Leu Tyr Pro His Asp Asp Glu Met Leu
225                 230                 235                 240

Ala Arg Tyr Leu Ser Leu Ala Glu Thr Gly Arg Glu Ala Glu Phe Leu
                245                 250                 255

Glu Thr Leu Leu Thr Arg Arg Ala Ala
            260                 265

<210> SEQ ID NO 18
<211> LENGTH: 246
<212> TYPE: PRT
<213> ORGANISM: Myxococcus xanthus
<220> FEATURE:
<223> OTHER INFORMATION: strain DK 1622

<400> SEQUENCE: 18

Met Ser Ala Thr Leu Asp Ile Thr Pro Ala Glu Thr Val Val Ser Leu
1               5                   10                  15

```
Leu Ala Arg Gln Ile Asp Asp Gly Gly Val Ala Thr Gly Val Ala
            20                  25                  30

Ser Pro Leu Ala Ile Leu Ala Ile Ala Val Ala Arg Ala Thr His Ala
        35                  40                  45

Pro Asp Leu Thr Tyr Leu Ala Cys Val Gly Ser Leu Asp Pro Glu Ile
50                  55                  60

Pro Thr Leu Leu Pro Ser Ser Glu Asp Leu Gly Tyr Leu Asp Gly Arg
65                  70                  75                  80

Ser Ala Glu Ile Thr Ile Pro Asp Leu Phe Asp His Ala Arg Arg Gly
                85                  90                  95

Arg Val Asp Thr Val Phe Phe Gly Ala Ala Glu Val Asp Ala Glu Gly
            100                 105                 110

Arg Thr Asn Met Thr Ala Ser Gly Ser Leu Asp Lys Pro Arg Thr Lys
        115                 120                 125

Phe Pro Gly Val Ala Gly Ala Ala Thr Leu Arg Gln Trp Val Arg Arg
130                 135                 140

Pro Val Leu Leu Val Pro Arg Gln Ser Arg Arg Asn Leu Val Pro Glu
145                 150                 155                 160

Val Gln Val Ala Thr Thr Arg Asp Pro Arg Arg Pro Val Thr Leu Ile
                165                 170                 175

Ser Asp Leu Gly Val Phe Glu Leu Gly Ala Ser Gly Ala Arg Leu Leu
            180                 185                 190

Ala Arg His Pro Trp Ala Ser Glu Glu His Ile Ala Glu Arg Thr Gly
        195                 200                 205

Phe Ala Phe Gln Val Ser Glu Ala Leu Ser Val Thr Ser Leu Pro Asp
210                 215                 220

Ala Arg Thr Val Ala Ala Ile Arg Ala Ile Asp Pro His Gly Tyr Arg
225                 230                 235                 240

Asp Ala Leu Val Gly Ala
                245

<210> SEQ ID NO 19
<211> LENGTH: 132
<212> TYPE: PRT
<213> ORGANISM: Escherichia coli
<220> FEATURE:
<223> OTHER INFORMATION: strain K12

<400> SEQUENCE: 19

Met Ser Thr Thr His Asn Val Pro Gln Gly Asp Leu Val Leu Arg Thr
1               5                   10                  15

Leu Ala Met Pro Ala Asp Thr Asn Ala Asn Gly Asp Ile Phe Gly Gly
            20                  25                  30

Trp Leu Met Ser Gln Met Asp Ile Gly Gly Ala Ile Leu Ala Lys Glu
        35                  40                  45

Ile Ala His Gly Arg Val Val Thr Val Arg Val Glu Gly Met Thr Phe
    50                  55                  60

Leu Arg Pro Val Ala Val Gly Asp Val Val Cys Cys Tyr Ala Arg Cys
65                  70                  75                  80

Val Gln Lys Gly Thr Thr Ser Val Ser Ile Asn Ile Glu Val Trp Val
                85                  90                  95

Lys Lys Val Ala Ser Glu Pro Ile Gly Gln Arg Tyr Lys Ala Thr Glu
            100                 105                 110

Ala Leu Phe Lys Tyr Val Ala Val Asp Pro Glu Gly Lys Pro Arg Ala
        115                 120                 125
```

Leu Pro Val Glu
    130

<210> SEQ ID NO 20
<211> LENGTH: 286
<212> TYPE: PRT
<213> ORGANISM: Escherichia coli
<220> FEATURE:
<223> OTHER INFORMATION: strain K12

<400> SEQUENCE: 20

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 21
<211> LENGTH: 289
<212> TYPE: PRT
<213> ORGANISM: Pseudomonas putida

<400> SEQUENCE: 21

Met Ser His Val Leu Asp Asp Leu Val Asp Leu Leu Ser Leu Glu Ser
1               5                   10                  15

```
Ile Glu Glu Asn Leu Phe Arg Gly Arg Ser Gln Asp Leu Gly Phe Arg
         20                  25                  30

Gln Leu Tyr Gly Gly Gln Val Leu Gly Gln Ser Leu Ser Ala Ala Ser
         35                  40                  45

Gln Thr Val Glu Asp Ala Arg His Val His Ser Leu His Gly Tyr Phe
 50                  55                  60

Leu Arg Pro Gly Asp Ala Ser Leu Pro Val Val Tyr Ser Val Asp Arg
 65                  70                  75                  80

Val Arg Asp Gly Gly Ser Phe Ser Thr Arg Arg Val Thr Ala Ile Gln
                 85                  90                  95

Lys Gly Gln Thr Ile Phe Thr Cys Ser Ala Ser Phe Gln Tyr Asp Glu
             100                 105                 110

Glu Gly Phe Glu His Gln Ala Gln Met Pro Asp Val Val Gly Pro Glu
         115                 120                 125

Asn Leu Pro Thr Glu Val Glu Leu Ala His Ala Met Ala Asp Gln Leu
         130                 135                 140

Pro Glu Arg Ile Arg Asp Lys Val Leu Cys Ala Lys Pro Ile Glu Ile
145                 150                 155                 160

Arg Pro Val Thr Glu Arg Asp Pro Phe Asn Pro Lys Pro Gly Asp Pro
                165                 170                 175

Val Lys Tyr Ala Trp Phe Arg Ala Asp Gly Asn Leu Pro Asp Val Pro
            180                 185                 190

Ala Leu His Lys Tyr Met Leu Ala Tyr Ala Ser Asp Phe Gly Leu Leu
        195                 200                 205

Thr Thr Ala Leu Leu Pro His Gly Lys Ser Val Trp Gln Arg Asp Met
210                 215                 220

Gln Ile Ala Ser Leu Asp His Ser Leu Trp Phe His Gly Asn Leu Arg
225                 230                 235                 240

Ala Asp Gln Trp Leu Leu Tyr Ala Thr Asp Ser Pro Trp Ala Gly Asn
                245                 250                 255

Ser Arg Gly Phe Cys Arg Gly Ser Ile Phe Asn Gln Ala Gly Gln Leu
            260                 265                 270

Val Ala Ser Ser Ser Gln Glu Gly Leu Ile Arg His Arg Lys Asp Trp
        275                 280                 285

Ala

<210> SEQ ID NO 22
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer"
      /organism="Artificial Sequence"

<400> SEQUENCE: 22
cccgcggccg ccctatcgat ttattagc                                          28

<210> SEQ ID NO 23
<211> LENGTH: 27
<212> TYPE: DNA
<213> ORGANISM: Artificial Sequence
<220> FEATURE:
<221> NAME/KEY: source
<222> LOCATION: 1..27
<223> OTHER INFORMATION: /mol_type="unassigned DNA"
      /note="Primer"
```

/organism="Artificial Sequence"

<400> SEQUENCE: 23
ttaattaatg aaagaagtgg tgattgc                                              27

<210> SEQ ID NO 24
<211> LENGTH: 49
<212> TYPE: DNA
<213> ORGANISM: Artificial Sequence
<220> FEATURE:
<221> NAME/KEY: source
<222> LOCATION: 1..49
<223> OTHER INFORMATION: /mol_type="unassigned DNA"
      /note="Primer"
      /organism="Artificial Sequence"

<400> SEQUENCE: 24
ggggaattca ggaggtgtac tagatgcatc atcatcatca ccacatgcc                      49

<210> SEQ ID NO 25
<211> LENGTH: 33
<212> TYPE: DNA
<213> ORGANISM: Artificial Sequence
<220> FEATURE:
<221> NAME/KEY: source
<222> LOCATION: 1..33
<223> OTHER INFORMATION: /mol_type="unassigned DNA"
      /note="Primer"
      /organism="Artificial Sequence"

<400> SEQUENCE: 25
cccggtacct tattagcgac ctttataaac cgg                                       33

<210> SEQ ID NO 26
<211> LENGTH: 49
<212> TYPE: DNA
<213> ORGANISM: Artificial Sequence
<220> FEATURE:
<221> NAME/KEY: source
<222> LOCATION: 1..49
<223> OTHER INFORMATION: /mol_type="unassigned DNA"
      /note="Primer"
      /organism="Artificial Sequence"

<400> SEQUENCE: 26
ggggcggccg caggaggtgt actagatgca ccatcatcat catcacagc                      49

<210> SEQ ID NO 27
<211> LENGTH: 32
<212> TYPE: DNA
<213> ORGANISM: Artificial Sequence
<220> FEATURE:
<221> NAME/KEY: source
<222> LOCATION: 1..32
<223> OTHER INFORMATION: /mol_type="unassigned DNA"
      /note="Primer"
      /organism="Artificial Sequence"

<400> SEQUENCE: 27
cccaagcttt tattacggtt taacgctata gc                                        32

<210> SEQ ID NO 28
<211> LENGTH: 299
<212> TYPE: PRT
<213> ORGANISM: Bacillus subtilis
<220> FEATURE:
<223> OTHER INFORMATION: strain 168

<400> SEQUENCE: 28

```
Met Lys Leu Lys Asp Leu Ile Gly Lys Ala Ser Ile His Lys Asn Lys
1               5                   10                  15

Thr Ile Ala Val Ala His Ala Glu Asp Glu Val Ile Arg Ala Val
            20                  25                  30

Lys Leu Ala Ala Glu His Leu Ser Ala Arg Phe Leu Leu Thr Gly Asp
                35                  40                  45

Ser Lys Lys Leu Asn Glu Leu Thr Ser Ser Met Gln Gly His Gln Val
50                  55                  60

Glu Ile Val His Ala Asn Thr Pro Glu Glu Ser Ala Lys Leu Ala Val
65                  70                  75                  80

Arg Ala Val His His Lys Thr Ala Asp Val Leu Met Lys Gly Asn Val
                85                  90                  95

Pro Thr Ser Val Leu Leu Lys Ala Val Leu Asn Arg Gln Glu Gly Leu
                100                 105                 110

Arg Ser Ala Ser Val Leu Ser His Val Ala Val Phe Asp Ile Pro Asp
            115                 120                 125

Phe Asp Arg Leu Met Phe Val Thr Asp Ser Ala Met Asn Ile Ala Pro
130                 135                 140

Ser Leu Glu Glu Leu Arg Gln Ile Leu Gln Asn Ala Val His Val Ala
145                 150                 155                 160

His Ala Val Gly Asn Asn Met Pro Lys Ala Ala Leu Ala Ala Val
                165                 170                 175

Glu Thr Val Asn Pro Lys Met Glu Ala Thr Val Asn Ala Ala Leu
                180                 185                 190

Ala Gln Met Tyr Lys Arg Gly Gln Ile Lys Gly Cys Ile Val Asp Gly
                195                 200                 205

Pro Leu Ala Leu Asp Asn Ala Val Ser Gln Ile Ala Ala Ala Gln Lys
        210                 215                 220

Lys Ile Ser Gly Asp Val Ala Gly Asn Ala Asp Ile Leu Leu Val Pro
225                 230                 235                 240

Thr Ile Glu Ala Gly Asn Ile Leu Tyr Lys Ser Leu Ile Tyr Phe Ala
                245                 250                 255

Lys Ala Ser Val Ala Ala Val Ile Thr Gly Ala Lys Ala Pro Ile Ala
                260                 265                 270

Leu Thr Ser Arg Ala Asp Ser Ala Glu Asn Lys Leu Tyr Ser Ile Ala
                275                 280                 285

Leu Ala Ile Cys Ala Ser Glu Glu Tyr Thr His
        290                 295

<210> SEQ ID NO 29
<211> LENGTH: 273
<212> TYPE: PRT
<213> ORGANISM: Enterococcus faecalis
<220> FEATURE:
<223> OTHER INFORMATION: MTUP9

<400> SEQUENCE: 29

Met Ile Thr Val Ser Ile Ala Gly Gly Ser Gln Pro Glu Ile Leu Gln
1               5                   10                  15

Leu Val Lys Lys Ala Leu Lys Glu Ala Glu Gln Pro Leu Gln Phe Ile
                20                  25                  30

Val Phe Asp Thr Asn Glu Asn Leu Asp Thr Glu Asn Leu Trp Lys Tyr
                35                  40                  45

Val His Cys Ser Asp Glu Ala Thr Val Ala Gln Glu Ala Val Ser Leu
50                  55                  60
```

```
Val Ala Thr Gly Gln Ala Gln Ile Leu Leu Lys Gly Ile Ile Gln Thr
 65                  70                  75                  80

His Thr Leu Leu Lys Glu Met Leu Lys Ser Glu His Gln Leu Lys Asn
                 85                  90                  95

Lys Pro Ile Leu Ser His Val Ala Met Val Glu Leu Pro Ala Gly Lys
            100                 105                 110

Thr Phe Leu Leu Thr Asp Cys Ala Met Asn Ile Ala Pro Thr Gln Ala
        115                 120                 125

Thr Leu Ile Glu Ile Val Glu Asn Ala Lys Glu Val Ala Gln Lys Leu
    130                 135                 140

Gly Leu His His Pro Lys Ile Ala Leu Leu Ser Ala Ala Glu Asn Phe
145                 150                 155                 160

Asn Pro Lys Met Pro Ser Ser Val Leu Ala Lys Glu Val Thr Ala His
                165                 170                 175

Phe Asn Gly Gln Gln Glu Ala Thr Val Phe Gly Pro Leu Ser Leu Asp
            180                 185                 190

Leu Ala Thr Ser Glu Glu Ala Val Ala His Lys Arg Tyr Ser Gly Pro
        195                 200                 205

Ile Met Gly Asp Ala Asp Ile Leu Val Val Pro Thr Ile Asp Val Gly
    210                 215                 220

Asn Cys Leu Tyr Lys Ser Leu Thr Leu Phe Gly His Ala Lys Val Gly
225                 230                 235                 240

Gly Thr Ile Val Gly Thr Lys Val Pro Val Val Leu Thr Ser Arg Ser
                245                 250                 255

Asp Ser Thr Glu Ser Lys Phe His Ser Leu Arg Phe Ala Met Arg Gln
            260                 265                 270

Val

<210> SEQ ID NO 30
<211> LENGTH: 384
<212> TYPE: PRT
<213> ORGANISM: Lactobacillus casei
<220> FEATURE:
<223> OTHER INFORMATION: strain W56

<400> SEQUENCE: 30

Met Arg Asp Cys Thr Thr Glu Arg Arg Cys Leu Met Thr Met His Pro
1               5                   10                  15

Lys Arg Asp Val Val Ile Val Ile Asn Pro Gly Ser Thr Ser Ser Lys
                20                  25                  30

Ile Ala Leu Phe Lys Ala Gly Lys Met Val Ala Glu Arg Thr Leu Asn
            35                  40                  45

His Ser Leu Ala Glu Leu Ser Gln Phe Asp Ser Val Ile Ala Gln Lys
        50                  55                  60

Asp Phe Arg Met Gln Ala Ile Gln Glu Phe Leu Ala Asp Gln Asp Phe
 65                 70                  75                  80

Ser Ala Ser Glu Val Leu Ala Val Ala Gly Arg Gly Leu Leu Lys
                 85                  90                  95

Pro Ile Pro Gly Gly Thr Tyr Ala Val Asn Glu Ala Met Leu Asp Asp
            100                 105                 110

Leu Thr Ala Ala Lys Arg Asn Glu His Ala Ser Asn Leu Gly Ala Gly
        115                 120                 125

Leu Ala Gln Gln Val Ala Asp Gln Tyr Gly Val Lys Ala Tyr Val Val
    130                 135                 140
```

```
Asp Pro Pro Val Val Asp Glu Leu Gln Pro Leu Ala Arg Ile Ser Gly
145                 150                 155                 160

Leu Lys Gly Ile Glu Arg His Ser Ala Ala His Val Leu Asn Gln Lys
            165                 170                 175

Ala Met Ala Arg Gln Val Leu Ala Thr Met Gly Lys Thr Tyr Ala Thr
        180                 185                 190

Ser Arg Val Ile Val Ala His Ile Gly Gly Leu Ser Ile His Ala
    195                 200                 205

His Glu Asn Gly Arg Met Ile Asp Gly Asn Asn Gly Ile Asp Gly Glu
        210                 215                 220

Gly Pro Tyr Ser Pro Glu Arg Ala Gly Ser Leu Pro Leu Val Asp Phe
225                 230                 235                 240

Val Ala Lys Val Leu Ala Glu Arg Leu Thr Leu Asp Gln Val Lys Lys
            245                 250                 255

Leu Leu Ala Ser Gln Ser Gly Leu Arg Ser Tyr Leu Asn Asp Ile Ser
        260                 265                 270

Ile Lys Asn Ile Val Thr Arg Ile Ala Glu Gly Asp Glu Thr Ala Lys
        275                 280                 285

Phe Tyr Leu Asp Gly Met Ile Tyr Gln Ile Lys Lys Gln Ile Ala Glu
290                 295                 300

Met Ala Gly Val Leu Asn Gly Gln Val Asp Val Ile Ile Leu Thr Gly
305                 310                 315                 320

Gly Ala Ala Tyr Ala Thr Ala Val Thr Val Pro Leu Gln His Asp Leu
            325                 330                 335

Ala Trp Ile Ala Pro Val Val Arg Pro Gly Glu Met Glu Met Gln
        340                 345                 350

Ala Leu Tyr Glu Gly Val Met Arg Val Leu Asn His Glu Glu Pro Val
        355                 360                 365

Arg Val Tyr Gln Ser Asp Ala Ser Thr Ile Lys Gly Thr Gly Arg
        370                 375                 380

<210> SEQ ID NO 31
<211> LENGTH: 370
<212> TYPE: PRT
<213> ORGANISM: Geobacillus sp.
<220> FEATURE:
<223> OTHER INFORMATION: GHH01

<400> SEQUENCE: 31

Met Glu Glu Gln Lys Phe Arg Ile Leu Thr Ile Asn Pro Gly Ser Thr
1               5                   10                  15

Ser Thr Lys Ile Gly Val Phe Glu Asn Glu Arg Pro Leu Leu Glu Lys
            20                  25                  30

Thr Ile Arg His Glu Ala Asp Val Leu Arg Gln Tyr Lys Thr Ile Ala
        35                  40                  45

Asp Gln Tyr Glu Phe Arg Lys Gln Thr Ile Leu Gln Ala Leu Asp Glu
    50                  55                  60

Glu Gly Ile Asn Leu Ser Lys Leu Ser Ala Val Cys Gly Arg Gly Gly
65              70                  75                  80

Leu Leu Arg Pro Ile Glu Gly Gly Thr Tyr Arg Val Asn Glu Ala Met
            85                  90                  95

Leu Glu Asp Leu Arg Arg Gly Tyr Ser Gly Gln His Ala Ser Asn Leu
        100                 105                 110

Gly Gly Ile Leu Ala His Glu Ile Ala Ser Ala Leu Asn Ile Pro Ala
        115                 120                 125
```

-continued

```
Phe Ile Val Asp Pro Val Val Val Asp Glu Leu Asp Pro Ile Ala Arg
    130                 135                 140
Ile Ser Gly Phe Pro Leu Ile Glu Arg Arg Ser Ile Phe His Ala Leu
145                 150                 155                 160
Asn Gln Lys Ala Val Ala Arg Arg Val Ala Lys Gln Leu Gly Lys Arg
                165                 170                 175
Tyr Asp Glu Leu Asn Leu Ile Val Ala His Met Gly Gly Gly Ile Thr
                180                 185                 190
Val Gly Ala His Lys Gln Gly Arg Val Val Asp Val Asn Asn Gly Leu
            195                 200                 205
Asp Gly Glu Gly Pro Phe Ser Pro Glu Arg Ala Gly Thr Val Pro Ala
    210                 215                 220
Gly Asp Leu Val Ala Leu Cys Phe Ser Gly Glu Tyr Tyr Arg Glu Glu
225                 230                 235                 240
Ile Met Asn Met Leu Val Gly Gly Gly Leu Val Gly Tyr Leu Gly
                245                 250                 255
Thr Asn Asp Ala Val Lys Val Glu Asn Met Ile Glu Ala Gly Asp Glu
                260                 265                 270
Lys Ala Lys Leu Val Tyr Glu Ala Met Ala Tyr Gln Val Ala Lys Glu
            275                 280                 285
Ile Gly Ala Ala Ser Ala Val Leu Ser Gly Lys Val Asp Ala Ile Ile
    290                 295                 300
Leu Thr Gly Gly Leu Ala Tyr Gly Lys Ser Phe Val Glu Gln Ile Thr
305                 310                 315                 320
Arg Arg Val Gln Trp Ile Ala Asp Val Ile Val His Pro Gly Glu Asn
                325                 330                 335
Glu Leu Gln Ala Leu Ala Glu Gly Ala Leu Arg Val Leu Arg Gly Glu
                340                 345                 350
Glu Glu Glu Lys Val Tyr Pro Gly Glu Ala Val Ser Pro Ile Pro Ala
            355                 360                 365
Arg Arg
370
```

METHODS FOR PRODUCING 3-HYDROXY-3-METHYLBUTYRIC ACID

CROSS-REFERENCE TO RELATED APPLICATIONS

This application is a § 371 National Stage Application of PCT/EP2015/071185 filed Sep. 16, 2015, which claims priority to EP 14185180.8 filed Sep. 17, 2014 and EP 15157918.2 filed Mar. 6, 2015. All of these documents are hereby incorporated by reference in their entirety.

The present invention relates to methods for producing 3-hydroxy-3-methylbutyric acid.

In one aspect the present invention relates to a method for producing 3-hydroxy-3-methylbutyric acid comprising the step of enzymatically converting 3-methylcrotonyl-CoA into 3-methylcrotonic acid and the step of enzymatically further converting the thus produced 3-methylcrotonic acid into 3-hydroxy-3-methylbutyric acid. The conversion of 3-methylcrotonyl-CoA into 3-methylcrotonic acid can be achieved by a direct conversion which preferably makes use of an enzyme which belongs to the family of thioester hydrolases (also referred to as thioesterases; EC 3.1.2)) or to the family of CoA-transferases (EC 2.8.3). In the alternative, the conversion of 3-methylcrotonyl-CoA into 3-methylcrotonic acid can be achieved by a conversion which first encompasses the conversion of 3-methylcrotonyl-CoA into 3-methylcrotonyl-phosphate and the subsequent conversion of 3-methylcrotonyl-phosphate into 3-methylcrotonic acid. The conversion of 3-methylcrotonic acid into 3-hydroxy-3-methylbutyric acid preferably makes use of an enzyme which belongs to the family of hydro-lyases (EC 4.2.1), in particular of an aconitate hydratase (EC 4.2.1.3) or of a maleate hydratase (EC 4.2.1.31) or of a 2-methylcitrate dehydratase (EC 4.2.1.79).

The present invention also relates to a method for producing 3-hydroxy-3-methylbutyric acid from 3-methylcrotonyl-CoA comprising the steps of:
(a) enzymatically converting 3-methylcrotonyl-CoA into 3-hydroxy-3-methylbutyryl-CoA; and
(b) further enzymatically converting the thus produced 3-hydroxy-3-methylbutyryl-CoA into 3-hydroxy-3-methylbutyric acid wherein the enzymatic conversion of 3-hydroxy-3-methylbutyryl-CoA into 3-hydroxy-3-methylbutyric acid according to step (b) is achieved by first converting 3-hydroxy-3-methylbutyryl-CoA into 3-hydroxy-3-methylbutyryl phosphate and then subsequently converting the thus produced 3-hydroxy-3-methylbutyryl phosphate into 3-hydroxy-3-methylbutyric acid.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Butylene exists in four forms, one of which, isobutene (also referred to as isobutylene), enters into the composition of methyl-tert-butyl-ether (MTBE), an anti-knock additive for automobile fuel. Isobutene can also be used to produce isooctene, which in turn can be reduced to isooctane (2,2,4-trimethylpentane); the very high octane rating of isooctane makes it the best fuel for so-called "gasoline" engines. Alkenes such as isobutene are currently produced by catalytic cracking of petroleum products (or by a derivative of the Fischer-Tropsch process in the case of hexene, from coal or gas). The production costs are therefore tightly linked to the price of oil. Moreover, catalytic cracking is sometimes associated with considerable technical difficulties which increase process complexity and production costs.

The production by a biological pathway of alkenes such as isobutene is called for in the context of a sustainable industrial operation in harmony with geochemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Ladygina et al. (Process Biochemistry 41 (2006), 1001) and Wackett (Current Opinions in Chemical Biology 21 (2008), 187). The conversion of isovalerate to isobutene by the yeast *Rhodotorula minuta* has been described (Fujii et al. (Appl. Environ. Microbiol. 54 (1988), 583)), but the efficiency of this reaction, less than 1 millionth per minute, or about 1 for 1000 per day, is far from permitting an industrial application. The reaction mechanism was elucidated by Fukuda et al. (BBRC 201 (1994), 516) and involves a cytochrome P450 enzyme which decarboxylates isovalerate by reduction of an oxoferryl group $Fe^V=O$. Large-scale biosynthesis of isobutene by this pathway seems highly unfavorable, since it would require the synthesis and degradation of one molecule of leucine to form one molecule of isobutylene. Also, the enzyme catalyzing the reaction uses heme as cofactor, poorly lending itself to recombinant expression in bacteria and to improvement of enzyme parameters. For all these reasons, it appears very unlikely that this pathway can serve as a basis for industrial exploitation. Other microorganisms have been described as being marginally capable of naturally producing isobutene from isovalerate; the yields obtained are even lower than those obtained with *Rhodotorula minuta* (Fukuda et al. (Agric. Biol. Chem. 48 (1984), 1679)).

Gogerty et al. (Appl. Environm. Microbiol. 76 (2010), 8004-8010) and van Leeuwen et al. (Appl. Microbiol. Biotechnol. 93 (2012), 1377-1387) describe the production of isobutene from acetoacetyl-CoA by enzymatic conversions wherein the last step of the proposed pathway is the conversion of 3-hydroxy-3-methylbutyric acid (also referred to as 3-hydroxyisovalerate (HIV)) by making use of a mevalonate diphosphate decarboxylase. This reaction for the production of isobutene from 3-hydroxy-3-methylbutyric acid is also described in WO2010/001078. In Gogerty et al. (loc. cit.) and in van Leeuwen et al. (loc. cit.) the production of 3-hydroxy-3-methylbutyric acid is proposed to be achieved by the conversion of 3-methylcrotonyl-CoA via 3-hydroxy-3-methylbutyryl-CoA. In order to further improve the efficiency and variability of methods for producing isobutene from renewable resources, there is a need for alternative routes for the provision of 3-hydroxy-3-methylbutyric acid which can be used as a substrate for the enzymatic conversion into isobutene.

The present invention meets this demand by providing the methods as disclosed herein and as specified in the claims. Thus, in one aspect, the present invention relates to a method for the conversion of 3-methylcrotonyl-CoA into 3-hydroxy-3-methylbutyric acid comprising the steps of:
(a) enzymatically converting 3-methylcrotonyl-CoA into 3-methylcrotonic acid; and
(b) further enzymatically converting the thus produced 3-methylcrotonic acid into 3-hydroxy-3-methylbutyric acid.

This conversion of 3-methylcrotonyl-CoA into 3-hydroxy-3-methylbutyric acid provides an alternative route to that proposed in the prior art which converts 3-methylcrotonyl-CoA via 3-hydroxy-3-methylbutyryl-CoA into 3-hydroxy-3-methylbutyric acid.

According to the present invention the conversion of 3-methylcrotonyl-CoA into 3-methylcrotonic acid can be achieved by a direct conversion which preferably makes use of an enzyme which belongs to the family of thioester hydrolases (in the following referred to as thioesterases (EC 3.1.2)) or to the family of CoA-transferases (EC 2.8.3). In the alternative, the conversion of 3-methylcrotonyl-CoA into 3-methylcrotonic acid can be achieved by a conversion which first encompasses the conversion of 3-methylcrotonyl-CoA into 3-methylcrotonyl-phosphate and the subsequent conversion of 3-methylcrotonyl-phosphate into 3-methylcrotonic acid.

Thus, in a first embodiment the conversion of 3-methylcrotonyl-CoA into 3-methylcrotonic acid can be achieved by a direct conversion. According to the present invention such a direct enzymatic conversion of 3-methylcrotonyl-CoA into 3-methylcrotonic acid according to step (a) of the above described method can, for example, be achieved by the use of (i) a thioesterase (EC 3.1.2); or
(ii) a CoA-transferase (EC 2.8.3).

Thioesterases (TEs; also referred to as thioester hydrolases) are enzymes which are classified as EC 3.1.2. Presently thioesterases are classified as EC 3.1.2.1 through EC 3.1.2.27 and EC 3.1.2.- for unclassified TEs. Cantu et al. (Protein Science 19 (2010), 1281-1295) describe that there are 23 families of thioesterases which are unrelated to each other as regards the primary structure. However, it is assumed that all members of the same family have essentially the same tertiary structure. Thioesterases hydrolyze the thioester bond between a carbonyl group and a sulfur atom.

The conversion of 3-methylcrotonyl-CoA into 3-methylcrotonic acid catalyzed by a thioesterase is schematically shown in FIG. 1.

In a preferred embodiment, a thioesterase employed in a method according to the present invention for converting 3-methylcrotonyl-CoA into 3-methylcrotonic acid is selected from the group consisting of:
acetyl-CoA hydrolase (EC 3.1.2.1);
palmitoyl-CoA hydrolase (EC 3.1.2.2);
3-hydroxyisobutyryl-CoA hydrolase (EC 3.1.2.4);
oleoyl-[acyl-carrier-protein] hydrolase (EC 3.1.2.14);
ADP-dependent short-chain-acyl-CoA hydrolase (EC 3.1.2.18);
ADP-dependent medium-chain-acyl-CoA hydrolase (EC 3.1.2.19); and
acyl-CoA hydrolase (EC 3.1.2.20).

Thus, in one preferred embodiment the direct conversion of 3-methylcrotonyl-CoA into 3-methylcrotonic acid is achieved by making use of an acetyl-CoA hydrolase (EC 3.1.2.1). Acetyl-CoA hydrolases are enzymes which catalyze the following reaction:

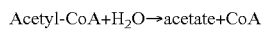
Acetyl-CoA+H$_2$O→acetate+CoA

This enzyme occurs in a variety of organisms, including eukaryotic and prokaryotic organisms, such as plants, animals, fungi and bacteria. The enzyme has, e.g., been described in *Rattus norvegicus* (Uniprot Accession number: Q99NB7), *Mus musculus*, *Sus scrofa*, *Bos taurus*, *Gallus gallus*, Platyrrhini, *Ovis aries*, *Mesocricetus auratus*, *Ascaris suum*, *Homo sapiens* (Uniprot Accession number: Q8WYK0), *Pisum sativum*, *Cucumis sativus*, Panicus sp., *Ricinus communis*, *Solanum tuberosum*, *Spinacia oleracea*, *Zea mays*, *Glycine max*, *Saccharomyces cerevisiae*, *Neurospora crassa*, *Candida albicans*, *Trypanosoma brucei brucei*, *Trypanosoma cruzi*, *Trypanosoma dionisii*, *Trypanosoma vespertilionis*, *Crithidia fasciculate*, *Clostridium aminovalericum*, *Acidaminococcus fermaentans*, *Bradyrhizobium japonicum* and *Methanosarcina barkeri*.

In another preferred embodiment the direct conversion of 3-methylcrotonyl-CoA into 3-methylcrotonic acid is achieved by making use of a palmitoyl-CoA hydrolase (EC 3.1.2.2). Palmitoyl-CoA hydrolases are enzymes which catalyze the following reaction:

Palmitoyl-CoA+H$_2$O→palmitate+CoA

This enzyme occurs in a variety of organisms, including eukaryotic and prokaryotic organisms, such as plants, animals, fungi and bacteria. The enzyme has, e.g., been described in *Arabidopsis thaliana* (Uniprot Accession number: Q8GYW7), *Pisum sativum*, *Spinacia oleracea*, *Bumilleriopsis filiformis*, *Eremosphaera viridis*, *Mougeotia scalaris*, *Euglena gracilis*, *Rhodotorula aurantiaca*, *Saccharaomyces cerevisiae*, *Candida rugosa*, *Caenorhabditis elegans*, *Mus musculus* (Uniprot Accession number: P58137), *Homo sapiens*, Platyrrhini, *Bos taurus*, *Canis lupus familiaris*, *Sus scrofa*, *Cavia procellus*, *Columba* sp., *Cricetulus griseus*, *Mesocricetus auratus*, *Drosophila melanogaster*, *Rattus norvegicus*, *Oryctolagus cuniculus*, *Gallus gallus*, *Anas platyrhynchos*, *Mycobacterium tuberculosis*, *Mycobacterium phlei*, *Mycobacterium smegmatis*, *Acinetobacter colcaceticus*, *Haemophilus influenza*, *Helicobacter pylori*, *Bacillus subtilis*, *Pseudomonas aeruginosa*, *Rhodobacter sphaeroides*, *Streptomyces coelicolor*, *Streptomyces venezuelae* and *E. coli*.

In a further preferred embodiment the direct conversion of 3-methylcrotonyl-CoA into 3-methylcrotonic acid is achieved by making use of a 3-hydroxyisobutyryl-CoA hydrolase (EC 3.1.2.4). 3-hydroxyisobutyryl-CoA hydrolases are enzymes which catalyze the following reaction:

3-hydroxyisobutyryl-CoA+H$_2$O→3-hydroxyisobutyrate+CoA

This enzyme occurs in a variety of organisms, including eukaryotic and prokaryotic organisms, such as plants, animals, fungi and bacteria. The enzyme has, e.g., been described in *Arabidopsis thaliana*, *Homo sapiens*, *Canus lupus familiaris*, *Rattus norvegicus*, *Bacillus cereus*, *Pseudomonas fluorescens* and *Pseudomonas aeruginosa*.

In yet another preferred embodiment the direct conversion of 3-methylcrotonyl-CoA into 3-methylcrotonic acid is achieved by making use of an oleoyl-[acyl-carrier-protein] hydrolase (EC 3.1.2.14). Oleoyl-[acyl-carrier-protein] hydrolases are enzymes which catalyze the following reaction:

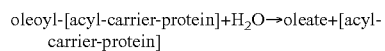
oleoyl-[acyl-carrier-protein]+H$_2$O→oleate+[acyl-carrier-protein]

This enzyme occurs in a variety of plants and bacteria. The enzyme has, e.g., been described in *Arabidopsis thaliana*, *Allium ampeloprasum*, *Curcurbita moschata*, *Cuphea calophylla*, *Cuphea hookeriana*, *Cuphea lanceolata*, *Cuphea wrightii*, *Umbellularia californica*, *Coriandrum sativum*, *Spinacia oleracea*, *Elaeis* sp., *Elaeis guineensis*, *Glycine max*, *Persea americana*, *Pisum sativum*, *Sinapis alba*, *Ulmus americana*, *Zea mays*, *Brassica juncea*, *Brassica napus*, *Brassica rapa* subsp. *campestris*, *Jatropha curcas*, *Ricinus communis*, *Cinnamomum camphorum*, *Macadamia tetraphylla*, *Magnifera indica*, *Madhuca longifolia*,

*Populus tomentosa, Chimonanthus praecox, Gossypium hirsutum, Diploknema butyracea, Helianthus annuus* and *Streptococcus pyogenes*.

In yet another preferred embodiment the direct conversion of 3-methylcrotonyl-CoA into 3-methylcrotonic acid is achieved by making use of an ADP-dependent short-chain-acyl-CoA hydrolase (EC 3.1.2.18). ADP-dependent short-chain-acyl-CoA hydrolases are enzymes which catalyze the following reaction:

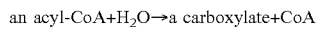

an acyl-CoA+H$_2$O→a carboxylate+CoA

This enzyme occurs in a variety of animals and has, e.g., been described in *Mus musculus, Rattus norvegicus* and *Mesocricetus auratus*.

In yet another preferred embodiment the direct conversion of 3-methylcrotonyl-CoA into 3-methylcrotonic acid is achieved by making use of an ADP-dependent medium-chain-acyl-CoA hydrolase (EC 3.1.2.19). ADP-dependent medium-chain-acyl-CoA hydrolases are enzymes which catalyze the following reaction:

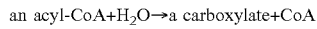

an acyl-CoA+H$_2$O→a carboxylate+CoA

This enzyme occurs in a variety of animals and has, e.g., been described in *Rattus norvegicus* and *Mesocricetus auratus*.

In a further preferred embodiment the direct conversion of 3-methylcrotonyl-CoA into 3-methylcrotonic acid is achieved by making use of an acyl-CoA hydrolase (EC 3.1.2.20). Acyl-CoA hydrolases are enzymes which catalyze the following reaction:

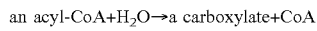

an acyl-CoA+H$_2$O→a carboxylate+CoA

This enzyme occurs in a variety of organisms, including eukaryotic and prokaryotic organisms, such as plants, animals, fungi and bacteria. The enzyme has, e.g., been described in *Arabidopsis thaliana, Rhodotorula aurantiaca, Bumilleriopsis filiformis, Eremosphaera viridis, Euglena gracilis, Mus musculus, Rattus norvegicus, Homo sapiens, Sus, scrofa, Bos taurus, Cais lupus familiaris, Cavia porcellus, Cricetus griseus, Drosophila melanogaster, Anas platyrhynchos, Gallus gallus, Caenorhabditis elegans, Saccharomyces cerevisiae, Candida rugosa, Escherichia coli, Haemophilus influenzae, Xanthomonas campestris, Streptomyces* sp., *Streptomyces coelicolor, Alcaligenes faecalis, Pseudomonas aeruginosa, Pseudomonas putida, Amycolatopsis mediterranei, Acinetobacter calcoaceticus, Helicobacter pylori, Rhodobacter sphaeroides* and *Mycobacterium phlei*. In a preferred embodiment the acyl-CoA hydrolase is an enzyme from *Escherichia coli*, from *Pseudomonas putida* or from *Haemophilus influenza*, more preferably the YciA enzyme from *E. coli* or its closely related homolog HI0827 from *Haemophilus* influenza (Zhuang et al., Biochemistry 47 (2008), 2789-2796). In another preferred embodiment the acetyl-CoA hydrolase is an enzyme from *Homo sapiens* (Cao et al., Biochemistry 48 (2009), 1293-1304). The enzymes from *E. coli, Haemophilus* influenza and *Homo sapiens* have been reported to be able to accept beta-methylcrotonyl-CoA (synonym for 3-methylcrotonyl-CoA) as a substrate.

Particularly preferred are the enzymes acyl-CoA thioester hydrolase from *E. coli* (Uniprot P0A8Z0; SEQ ID NO: 19), acyl-CoA thioesterase 2 from *E. coli* (Uniprot P0AGG2; SEQ ID NO: 20) and acyl-CoA thioesterase II from *Pseudomonas putida* (Uniprot Q88DR1, SEQ ID NO: 21).

In a particularly preferred embodiment, the acyl-CoA hydrolase employed in the method of the invention has an amino acid sequence as shown in any one of SEQ ID NOs: 19 to 21 or shows an amino acid sequence which is at least x % homologous to any one of SEQ ID NOs: 19 to 21 and has the activity of an acyl-CoA hydrolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the conversion of 3-methylcrotonyl-CoA into 3-methylcrotonic acid.

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

As described above, the direct conversion of 3-methylcrotonyl-CoA into 3-methylcrotonic acid can also be achieved by making use of an enzyme which is classified as a CoA-transferase (EC 2.8.3). The conversion of 3-methylcrotonyl-CoA into 3-methylcrotonic acid catalyzed by a CoA-transferase is schematically shown in FIG. 2.

CoA-transferases are found in organisms from all lines of descent. Most of the CoA-transferase belong to two well-known enzyme families (referred to in the following as families I and II) and there exists a third family which had been identified in anaerobic metabolic pathways of bacteria. A review describing the different families can be found in Heider (FEBS Letters 509 (2001), 345-349).

Family I contains, e.g., the following CoA-transferases:

For 3-oxo acids: enzymes classified in EC 2.8.3.5 or EC 2.8.3.6;

for short chain fatty acids: enzymes classified in EC 2.8.3.8 or EC 2.8.3.9;

for glutaconate: enzymes classified in EC 2.8.3.12;

for succinate: succinyl-CoA:acetate CoA-transferases, i.e. enzymes classified in EC 2.8.3.18 (see also Mullins et al., Biochemistry 51(2012), 8422-34; Mullins et al., J. Bacteriol. 190 (2006), 4933-4940).

Most enzymes of family I naturally use succinyl-CoA or acetyl-CoA as CoA donors. These enzymes contain two dissimilar subunits in different aggregation states. Two conserved amino acid sequence motives have been identified:

Prosites entry PS01273 (http://prosite.expasy.org/cgi-bin/prosite/prosite-search-ac?PDOC00980)

COA_TRANSF_1, PS01273; Coenzyme A transferases signature 1 (PATTERN) Consensus pattern:
[DN]-[GN]-x(2)-[LIVMFA](3)-G-G-F-x(3)-G-x-P
and
Prosites entries PS01273 (http://prosite.expasy.org/cgi-bin/prosite/prosite-search-ac?PDOC00980)
COA_TRANSF_2, PS01274; Coenzyme A transferases signature 2 (PATTERN) Consensus pattern:
[LF]-[HQ]-S-E-N-G-[LIVF](2)-[GA]
E (glutamic acid) is an active site residue.

In one particularly preferred embodiment the enzyme used for converting 3-methylcrotonyl-CoA into 3-methylcrotonic acid is a glutaconate-CoA transferase (EC 2.8.3.12). Preferred glutaconate-CoA transferases are glutaconate-CoA transferase subunit A or B from *Myxococcus xanthus* (Uniprot Q1D4I4 and Q1D4I3, respectively). In a particularly preferred embodiment, the glutaconate-CoA transferase employed in the method of the invention has an amino acid sequence as shown in SEQ ID NO: 17 or 18 or shows an amino acid sequence which is at least x % homologous to SEQ ID NO: 17 or 18 and has the activity of a glutaconate-CoA transferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the conversion of 3-methylcrotonyl-CoA into 3-methylcrotonic acid. As regards the determination of the degree of identity, the same applies as has been set forth herein above.

The family II of CoA-transferases consists of the homodimeric α-subunits of citrate lyase (EC 2.8.3.10) and citramalate lyase (EC 2.8.3.11). These enzymes catalyse the transfer of acyl carrier protein (ACP) which contains a covalently bound CoA-derivative. It was shown that such enzymes also accept free CoA-thioester in vitro, such as acetyl-CoA, propionyl-CoA, butyryl-CoA in the case of citrate lyase (Dimroth et al., Eur. J. Biochem. 80 (1977), 479-488) and acetyl-CoA and succinyl-CoA in the case of citramalate lyase (Dimroth et al., Eur. J. Biochem. 80 (1977), 469-477).

According to Heider (loc. cit.) family III of CoA-transferases consists of formyl-CoA:oxalate CoA-transferase, succinyl-CoA:(R)-benzylsuccinate CoA-transferase, (E)-cinnamoyl-CoA:(R)-phenyllactate CoA-transferase and butyrobetainyl-CoA:(R)-carnitine CoA-transferase. A further member of family III is succinyl-CoA:L-malate CoA-transferase whose function in autrophic CO$_2$ fixation of *Chloroflexus aurantiacus* is to activate L-malate to its CoA thioester with succinyl-CoA as the CoA donor (Friedman S. et al. J. Bacteriol. 188 (2006), 2646-2655). The amino acid sequences of the CoA-tranferase of this family show only a low degree of sequence identity to those of families I and II. These CoA-transferases occur in prokaryotes and eukaryotes, In a preferred embodiment the CoA-transferase employed in a method according to the present invention is a CoA-transferase which belongs to family I or II as described herein-above.

Preferably, the CoA-transferase employed in a method according to the present invention for the direct conversion of 3-methylcrotonyl-CoA into 3-methylcrotonic acid is selected from the group consisting of:
acetate CoA transferase (EC 2.8.3.8); and
butyrate-acetoacetate CoA-transferase (EC 2.8.3.9).

Thus, in one preferred embodiment the direct conversion of 3-methylcrotonyl-CoA into 3-methylcrotonic acid is achieved by making use of an acetate CoA-transferase (EC 2.8.3.8). Acetate CoA-transferases are enzymes which catalyze the following reaction:

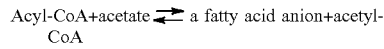
Acyl-CoA+acetate ⇌ a fatty acid anion+acetyl-CoA

This enzyme occurs in a variety of bacteria and has, e.g., been described in *Anaerostipes caccae, Eubacterium hallii, Faecalibacterium prausnitzii, Roseburia hominis, Roseburia intestinalis, Coprococcus* sp. and *Escherichia coli,*

In another preferred embodiment the direct conversion of 3-methylcrotonyl-CoA into 3-methylcrotonic acid is achieved by making use of a butyrate-acetoacetate CoA-transferase (EC 2.8.3.9). Butyrate-acetoacetate CoA-transferase are enzymes which catalyze the following reaction:

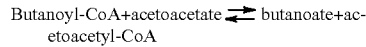
Butanoyl-CoA+acetoacetate ⇌ butanoate+acetoacetyl-CoA

This enzyme occurs in a variety of organisms, including eukaryotic and prokaryotic organisms, such as animals and bacteria. The enzyme has, e.g., been described in *Bos taurus, Clostridium* sp. and *Escherichia coli.*

As mentioned above, the conversion of 3-methylcrotonyl-CoA into 3-methylcrotonic acid can in the alternative also be achieved by a conversion which first encompasses the conversion of 3-methylcrotonyl-CoA into 3-methylcrotonyl-phosphate and the subsequent conversion of 3-methylcrotonyl-phosphate into 3-methylcrotonic acid. The corresponding reaction is schematically shown in FIG. 11. This conversion has the advantage of generating one molecule of ATP.

The conversion of 3-methylcrotonyl-CoA into 3-methylcrotonyl-phosphate can, e.g., be achieved by the use of a phosphate butyryltransferase (EC 2.3.1.19) or a phosphate acetyltransferase (EC 2.3.1.8).

Phosphate butyryltransferase (EC 2.3.1.19) naturally catalyzes the following reaction

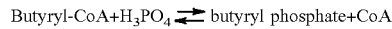
Butyryl-CoA+H$_3$PO$_4$ ⇌ butyryl phosphate+CoA

It has been described by Wiesenborn et al. (Appl. Environ. Microbiol. 55 (1989), 317-322) and by Ward et al. (J. Bacteriol. 181 (1999), 5433-5442) that phosphate butyryltransferases (EC 2.3.1.19) can use a number of substrates in addition to butyryl coenzyme A (butyryl-CoA), in particular acetyl-CoA, propionyl-CoA, isobutyryl-CoA, valeryl-CoA and isovaleryl-CoA.

The enzyme has been described to occur in a number of organisms, in particular in bacteria and in protozoae. In one embodiment the enzyme is from the protozoae *Dasytricha ruminantium*. In a preferred embodiment the phosphate butyryltransferase is a phosphate butyryltransferase from a bacterium, preferably from a bacterium of the genus *Bacillus, Butyrivibrio, Enterococcus* or *Clostridium*, more preferably *Enterococcus* or *Clostridium*, and even more preferably from *Bacillus megaterium, Bacillus subtilis, Butyrivibrio fibrisolvens, Clostridium acetobutylicum, Clostridium beijerinckii, Clostridium butyricum, Clostridium kluyveri, Clostridium saccharoacetobutylicum, Clostridium sprorogenes* or *Enterococcus faecalis*. Most preferably, the enzyme is from *Bacillus subtilis* (strain 168) (Uniprot Accession number P54530), *Clostridium acetobutylicum* (Uniprot Accession number F0K6W0) or from *Enterococcus faecalis* MTUP9 (Uniprot Accession number K4YRE8 or Uniprot Accession number A0A038BNC2). The sequences available for the phosphate butyryltransferase from *Enterococcus faecalis* under Uniprot Accession number K4YRE8 and Uniprot Accession number A0A038BNC2 have a sequence homology of 99.3%. The sequences available for the phosphate butyryltransferase from *Enterococcus faecalis* under Uniprot Accession number A0A038BNC2 is the more preferred one.

As mentioned, in a preferred embodiment, the enzyme is a phosphate butyryltransferase (EC 2.3.1.19) from *Bacillus subtilis* (strain 168) (Uniprot Accession number P54530). In a particularly preferred embodiment, the phosphate butyryltransferase (EC 2.3.1.19) employed in the method of the invention has an amino acid sequence as shown in SEQ ID NO: 28 or shows an amino acid sequence which is at least x % homologous to SEQ ID NO: 28 and has the activity of a phosphate butyryltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-CoA into 3-methylcrotonyl-phosphate as set forth herein above.

In another preferred embodiment, as mentioned, the enzyme is a phosphate butyryltransferase (EC 2.3.1.19) from *Enterococcus faecalis* MTUP9 (Uniprot Accession number K4YRE8 or Uniprot Accession number A0A038BNC2). In a particularly preferred embodiment, the phosphate butyryltransferase (EC 2.3.1.19) employed in the method of the invention has an amino acid sequence as shown in SEQ ID NO: 29 or shows an amino acid sequence which is at least x % homologous to SEQ ID NO: 29 and has the activity of a phosphate butyryltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-CoA into 3-methylcrotonyl-phosphate as set forth herein above.

As regards the determination of the degree of identity, the same applies as has been set forth herein above.

Phosphate acetyltransferase (EC 2.3.1.8) naturally catalyzes the following reaction

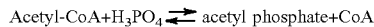

Acetyl-CoA+H$_3$PO$_4$ ⇌ acetyl phosphate+CoA

It has been described by Veit et al. (J. Biotechnol. 140 (2009), 75-83) that phosphate acetyltransferase can also use as a substrate butyryl-CoA or propionyl-CoA.

The accession numbers for this enzyme family in InterPro database are IPR012147 and IPR002505, "http://www.ebi-.ac.uk/interpro/entry/IPR002505"
(http://www.ebi.ac.uk/interpro/entry/IPR012147
http://www.ebi.ac.uk/interpro/entry/IPR002505)
See also http://pfam.sander.ac.uk/family/PF01515

The enzyme has been described in a variety of organisms, in particular bacteria and fungi. Thus, in one preferred embodiment the enzyme is an enzyme from a bacterium, preferably of the genus *Escherichia, Chlorogonium, Clostridium, Veillonella, Methanosarcina, Corynebacterium, Ruegeria, Salmonella, Azotobacter, Bradorhizobium, Lactobacillus, Moorella, Rhodopseudomonas, Sinorhizobium, Streptococcus, Thermotoga* or *Bacillus*, more preferably of the species *Escherichia coli, Chlorogonium elongatum, Clostridium kluyveri, Clostridium acetobutylicum, Clostridium acidurici, Veillonella parvula, Methanosarcina thermophila, Corynebacterium glutamicum, Ruegeria pomeroyi, Salmonella enterica, Azotobacter vinelandii, Bradyrhizobium japonicum, Lactobacillus fermentum, Lactobacillus sanfranciscensis, Moorella thermoacetica, Rhodopseudomonas palustris, Sinorhizobium meliloti, Streptococcus pyogenes, Thermotoga maritima* or *Bacillus subtilis*. In another preferred embodiment the enzyme is an enzyme from a fungus, preferably from the genus *Saccharomyces*, more preferably of the species *Saccharomyces cerevisiae*.

The conversion of 3-methylcrotonyl-phosphate into 3-methylcrotonic acid can, e.g., be achieved by the use of an enzyme which is classified as EC 2.7.2, i.e. a phosphotransferase. Such enzymes use a carboxy group as acceptor. In a preferred embodiment the conversion of 3-methylcrotonyl-phosphate into 3-methylcrotonic acid is achieved by the use of a butyrate kinase (EC 2.7.2.7), a branched-chain-fatty-acid kinase (EC 2.7.2.14), a propionate kinase (EC 2.7.2.15) or an acetate kinase (EC 2.7.2.1).

Butyrate kinases (EC 2.7.2.7) naturally catalyze the following reaction

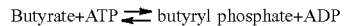

Butyrate+ATP ⇌ butyryl phosphate+ADP

It has been described, e.g. by Hartmanis (J. Biol. Chem. 262 (1987), 617-621) that butyrate kinase can use a number of substrates in addition to butyrate, e.g. valerate, isobutyrate, isovalerate and vinyl acetate. The enzyme has been described in a variety of organisms, in particular bacteria. In one preferred embodiment the enzyme is from a bacterium, preferably from a bacterium of the genus *Clostridium, Butyrivibrio, Thermotoga, Enterococcus, Lactobacillus* or *Geobacillus*. Preferred is *Clostridium, Lactobacillus* or *Geobacillus*. More preferably the enzyme is from a bacterium of the species *Clostridium acetobutylicum, Clostridium proteoclasticum, Clostridium tyrobutyricum, Clostridium butyricum, Clostridium pasteurianum, Clostridium tetanomorphum, Butyrivibrio firbrosolvens, Butyrivibrio hungatei, Thermotoga maritime, Enterococcus durans, Lactobacillus casei* (Uniprot Accession number K0N529) or *Geobacillus* sp. (Uniprot Accession number L8A0E1). Preferred is *Clostridium acetobutylicum, Lactobacillus casei* W56 or *Geobacillus* sp. GHH01. For *Clostridium acetobutylicum*, two butyrate kinases have been described: butyrate kinase 1 (Uniprot Accession number: Q45829) and butyrate kinase II (Uniprot Accession number: Q97II19).

As mentioned, in a preferred embodiment, the enzyme is a butyrate kinase (EC 2.7.2.7) from *Lactobacillus casei* W56 (Uniprot Accession number K0N529). In a particularly preferred embodiment, the butyrate kinase (EC 2.7.2.7) employed in the method of the invention has an amino acid sequence as shown in SEQ ID NO: 30 or shows an amino acid sequence which is at least x % homologous to SEQ ID NO: 30 and has the activity of a butyrate kinase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-phosphate into 3-methylcrotonic acid as set forth herein above.

In another preferred embodiment, the enzyme is a butyrate kinase (EC 2.7.2.7) from *Geobacillus* sp. GHH01 (Uniprot Accession number L8A0E1). In a particularly preferred embodiment, the butyrate kinase (EC 2.7.2.7) employed in the method of the invention has an amino acid sequence as shown in SEQ ID NO: 31 or shows an amino acid sequence which is at least x % homologous to SEQ ID NO: 31 and has the activity of a butyrate kinase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-phosphate into 3-methylcrotonic acid as set forth herein above.

Branched-chain-fatty-acid kinases (EC 2.7.2.14) naturally catalyze the following reaction 2-methylpropanoate+ATP ⇌ 2-methylpropanoyl phosphate+ADP This enzyme has been described to occur in a number of bacteria. Thus, in one preferred embodiment the enzyme is an enzyme from a bacterium, preferably of the genus *Spirochaeta* or *Thermotoga*, more preferably *Thermotoga* maritime.

Propionate kinases (EC 2.7.2.15) naturally catalyze the following reactions

Propanoate+ATP ⇌ propanoyl phosphate+ADP

Acetate+ATP ⇌ acetyl phosphate+ADP

This enzyme has been described to occur in a number of bacteria, in particular Enterobacteriacea. Thus, in one preferred embodiment the enzyme is an enzyme from a bacterium, preferably of the genus *Salmonella* or *Escherichia*, more preferably of the species *Salmonella enterica* or *Escherichia coli*.

Acetate kinases (EC 2.7.2.1) naturally catalyze the following reaction

Acetate+ATP ⇌ acetyl phosphate+ADP

This enzyme has been described to occur in a number of organisms, in particular bacteria and eukaryotes. In one preferred embodiment the enzyme is from a bacterium, preferably from a bacterium of the genus *Methanosarcina, Cryptococcus, Ethanoligenens, Propionibacterium, Roseovarius, Streptococcus, Salmonella, Acholeplasma, Acinetobacter, Ajellomyces, Bacillus, Borrelia, Chaetomium, Clostridium, Coccidioides, Coprinopsis, Cryptococcus, Cupriavidus, Desulfovibrio, Enterococcus, Escherichia, Ethanoligenes, Geobacillus, Helicobacter, Lactobacillus, Lactococcus, Listeria, Mesoplasma, Moorella, Mycoplasma, Oceanobacillus, Propionibacterium, Rhodospeudomonas, Roseovarius, Salmonella, Staphylococcus, Thermotoga* or *Veillonella*, more preferably from a bacterium of the species *Methanosarcina thermophila, Cryptococcus neoformans, Ethanoligenens harbinense, Propionibacterium acidipropionici, Streptococcus pneumoniae, Streptococcus enterica, Streptococcus pyogenes, Acholeplasma laidlawii, Acinetobacter calcoaceticus, Ajellomyces capsulatus, Bacillus subtilis, Borrelia burgdorferi, Chaetomium globosum, Clostridium acetobutylicum, Clostridium thermocellum, Coccidioides immitis, Coprinopsis cinerea, Cryptococcus neoformans, Cupriavidus necator, Desulfovibrio vulgaris, Enterococcus faecalis, Escherichia coli, Ethanoligenes harbinense, Geobacillus stearothermophilus, Helicobacter pylori, Lactobacillus delbrueckii, Lactobacillus acidophilus, Lactobacillus sanfranciscensis, Lactococcus lactis, Listeria monocytogenes, Mesoplasma florum, Methanosarcina acetivorans, Methanosarcina mazei, Moorella thermoacetica, Mycoplasma pneumoniae, Oceanobacillus iheyensis, Propionibacterium freudenreichii, Propionibacterium acidipropionici, Rhodospeudomonas palustris, Salmonella enteric, Staphylococcus aureus, Thermotoga* maritime or *Veillonella parvula*.

In another preferred embodiment the enzyme is an enzyme from a fungus, preferably from a fungus of the genus *Aspergillus, Gibberella, Hypocrea, Magnaporthe, Phaeosphaeria, Phanerochaete, Phytophthora, Sclerotinia, Uncinocarpus, Ustilago* or *Neurospora* even more preferably from a fungus of the species *Aspergillus fumigates, Aspergillus nidulans, Gibberella zeae, Hypocrea jecorina, Magnaporthe grisea, Phaeosphaeria nodorum, Phanerochaete chrysosporium, Phytophthora ramorum, Phytophthora sojae, Sclerotinia sclerotiorum, Uncinocarpus reesii, Ustilago maydis* or *Neurospora crassa*.

In a further preferred embodiment the enzyme is an enzyme from a plant or an algae, preferably from the genus *Chlamydomonas*, even more preferably from the species *Chlamydomonas reinhardtii*.

In another embodiment the enzyme is from an organism of the genus *Entamoeba*, more preferably of the species *Entamoeba histolytica*.

The above mentioned enzyme families suitable for the conversion of 3-methylcrotonyl-phosphate into 3-methylcrotonic acid have been shown to be evolutionary related and contain common sequence signatures. Theses signatures are referenced and described in Prosite database:
http://prosite.expasy.org/cgi-bin/prosite/nicedoc-.pl?PS01075

Gao et al. (FEMS Microbiol. Lett. 213 (2002), 59-65) already described genetically modified *E. coli* cells which have been transformed, inter alia, with the ptb gene and the buk gene from *Clostridium acetobutylicum* encoding a phosphate butyryltransferase (EC 2.3.1.19) and a butyrate kinase (EC 2.7.2.7), respectively. These *E. coli* cells have been shown to be able to produce D-(−)-3-hydroxybutyric acid (3HB).

The 3-methylcrotonic acid which is obtained in step (a) of the above described method is enzymatically further converted into 3-hydroxy-3-methylbutyric acid. This conversion can, e.g., be achieved by making use of an enzyme which belongs to the family of hydro-lyases (EC 4.2.1), in particular an aconitate hydratase (EC 4.2.1.3) or a maleate hydratase (EC 4.2.1.31) or a 2-methylcitrate dehydratase (EC 4.2.1.79). The reaction is schematically shown in FIG. 3.

Thus, in one preferred embodiment, the further enzymatic conversion of 3-methylcrotonic acid into 3-hydroxy-3-methylbutyric acid is achieved, according to the present invention, by making use of an aconitate hydratase (EC 4.2.1.3). Aconitate hydratases are enzymes which catalyze the following reaction:

Citrate ⇌ cis-aconitate+$H_2O$

This enzyme occurs in a variety of organisms, including eukaryotic and prokaryotic organisms, such as plants, animals, fungi and bacteria. The enzyme has, e.g., been described in *Citrus clementina, Citrus limon, Zea mays, Acer pseudoplatanus, Arabidopsis thaliana, Glycine max, Nicotiana benthamiana, Rheum* sp., *Sinapis alba, Solanum tuberosum, Zea mays, Homo sapiens, Bos taurus, Sus scrofa, Canis lupus familiaris, Oryctolagus cuniculus, Rattus norvegicus, Mus musculus, Crassostrea virginica, Drosophila melanogaster, Caenorhabditis elegans, Plasmodium falciparum, Trypanosoma brucei, Saccharomyces cerevisiae, Saccharomycopsis lipolytica, Aspergillus niger, Trametes saguinea, Sinorhizobium meliloti, Escherichia coli, Yarrowia lipolytica, Paracoccidioides brasiliensis, Corynebacterium glutamicum, Bacillus subtilis, Advenella kashmirensis, Azotobacter vinelandii, Bacillus cereus, Bacteroides fragilis, Mycobacterium tuberculosis, Pseudomonas aeruginosa, Salmonella enterica, Streptomyces aureus, Streptomyces viridochromogenes, Sulfolobus acidocaldarius, Sulfolobus solfataricus* and *Xanthomonas campestris*.

In another preferred embodiment, the further enzymatic conversion of 3-methylcrotonic acid into 3-hydroxy-3-methylbutyric acid is achieved, according to the present invention, by making use of a maleate hydratase (EC 4.2.1.31). Maleate hydratases are enzymes which catalyze the following reaction:

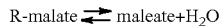

R-malate ⇌ maleate+H$_2$O

This enzyme occurs in a variety of organisms, including eukaryotic and prokaryotic organisms, such as animals, fungi and bacteria. The enzyme has, e.g., been described in *Oryctolagus cuniculus, Candida* sp., *Exophialia* sp., *Hansenula* sp., *Phanerochaete* sp., *Pichia* sp., *Pleurotus* sp., *Rhodotorula* sp., *Saccharomyces* sp., *Schizosaccharomyces* sp., *Sporobolomyces* sp., *Trichosporon* sp., *Yarrowia* sp., *Acinetobacter* sp., *Actinoplanes* sp. *Aspergillus* sp., *Brevibacterium* sp., *Corynebacterium* sp., *Klebsiella* sp., *Micrococcus* sp., *Mycobacterium* sp., *Nocardia* sp., *Penicillium* sp., *Proteus* sp., *Pseudomonas* sp., *Pseudomonas alcaligenes, Streptomyces* sp., *Arthrobacter* sp. and *Xanthobacter* sp.

In a further preferred embodiment, the further enzymatic conversion of 3-methylcrotonic acid into 3-hydroxy-3-methylbutyric acid is achieved, according to the present invention, by making use of a 2-methylcitrate dehydratase (EC 4.2.1.79). 2-methylcitrate dehydratases are enzymes which catalyze the following reaction:

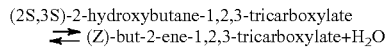

(2S,3S)-2-hydroxybutane-1,2,3-tricarboxylate
⇌ (Z)-but-2-ene-1,2,3-tricarboxylate+H$_2$O This enzyme occurs in a variety of bacteria and has, e.g., been described in *Salmonella enterica, Corynebacterium glutamicum, Escherichia coli, Mycobacterium smegmatis, Mycobacterium tuberculosis, Shewanella oneidensis, Vibrio cholerae, Pseudomonas* sp., *Pseudomonas pseudoalcaligenes* (van der Werf et al., Appl. Environ. Microbiol. 59 (1993), 2823-2829), *Rhodobacter capsulatus* and *Yarrowia lipolytica*.

The 3-hydroxy-3-methylbutyric acid produced according to a method of the present invention can, e.g., be further converted into isobutene. This conversion can be achieved, for example, by making use of a decarboxylase, in particular a mevalonate diphosphate (MDP) decarboxylase. This conversion has been described in the prior art, e.g., in WO 2010/001078, WO 2012/052427 and in Gogerty et al. (Appl. Environm. Microbiol. 76 (2010), 8004-8010). Thus, the present invention also relates to a method for the production of isobutene which comprises the conversion of 3-methylcrotonyl-CoA into 3-hydroxy-3-methylbutyric acid comprising the steps of:
(a) enzymatically converting 3-methylcrotonyl-CoA into 3-methylcrotonic acid; and
(b) further enzymatically converting the thus produced 3-methylcrotonic acid into 3-hydroxy-3-methylbutyric acid;
and which furthermore comprises the step of converting the thus produced 3-hydroxy-3-methylbutyric acid into isobutene via a decarboxylation reaction, preferably a decarboxylation reaction catalyzed by an MDP decarboxylase.

The 3-methylcrotonyl-CoA which is converted according to the method of the present invention into 3-methylcrotonic acid may itself be provided by an enzymatic reaction, e.g. by the conversion of 3-methylglutaconyl-CoA via decarboxylation into 3-methylcrotonyl-CoA. This reaction is schematically shown in FIG. 4. It may be catalyzed by different enzymes. In one preferred embodiment, the conversion of 3-methylglutaconyl-CoA via decarboxylation into 3-methylcrotonyl-CoA is catalyzed by a methylcrotonyl-CoA carboxylase (EC 6.4.1.4). Methylcrotonyl-CoA carboxylases have been described to catalyze the following reaction:

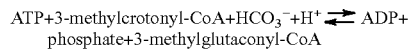

ATP+3-methylcrotonyl-CoA+HCO$_3^-$+H$^+$ ⇌ ADP+ phosphate+3-methylglutaconyl-CoA , i.e. the carboxylation, but they can be used to catalyze the reaction of decarboxylation. Methylcrotonyl-CoA carboxylases occur in a variety of organisms, including eukaryotic and prokaryotic organisms, such as plants, animals, fungi and bacteria. The enzyme has, e.g., been described in *Daucus carota, Glycine max, Hordeum vulgare, Pisum sativum, Solanum lycopersicum, Solanum tuberosum, Zea mays, Arabidopsis* sp., *Lens culinaris, Homo sapiens, Bos taurus, Rattus norvegicus, Mus musculus, Pagrus major, Emericella nidulans, Pseudomonas aeruginosa, Pseudomonas citronellolis, Acidaminococcus fermentans, Escherichia coli, Mycobacterium* sp. and *Achromobacter* sp.

In another preferred embodiment the conversion of 3-methylglutaconyl-CoA via decarboxylation into 3-methylcrotonyl-CoA is catalyzed by a geranoyl-CoA carboxylase (EC 6.4.1.5). Geranoyl-CoA carboxylases naturally catalyze the following reaction:

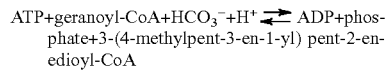

ATP+geranoyl-CoA+HCO$_3^-$+H$^+$ ⇌ ADP+phosphate+3-(4-methylpent-3-en-1-yl) pent-2-enedioyl-CoA The enzymes occurs in eukaryotes and prokaryotes, such as plants and bacteria. The enzyme has, e.g., been described in *Daucus carota, Glycine max, Zea mays, Pseudomonas* sp., *Pseudomonas aeruginosa, Pseudomonas citronellolis* and *Pseudomonas mendocina*.

In another preferred embodiment the conversion of 3-methylglutaconyl-CoA via decarboxylation into 3-methylcrotonyl-CoA is catalyzed by a 3-methylglutaconyl-CoA decarboxylase, e.g. a 3-methylglutaconyl-CoA decarboxylase of *Myxococcus xanthus* encoded by the liuB gene. This gene codes for an enzyme having the two subunits AibA and AibB (Li et al., Angew. Chem. Int. Ed. 52 (2013), 1304-1308).

Thus, the present invention also relates to a method for producing 3-hydroxy-3-methylbutyric acid from 3-methylglutaconyl-CoA in which 3-methylglutaconyl-CoA is first converted by a decarboxylation reaction into 3-methylcrotonyl-CoA which is then further enzymatically converted into 3-hydroxy-3-methylbutyric acid as described herein above.

The 3-methylglutaconyl-CoA to be converted into 3-methylcrotonyl-CoA can itself be provided by an enzymatic reaction which occurs naturally, which involves the conversion of 3-hydroxy-3-methylglutaryl-CoA into 3-methylglutaconyl-CoA and which is catalyzed, e.g., by enzymes classified as 3-methylglutaconyl-coenzyme A hydratase (EC 4.2.1.18). This reaction is schematically shown in FIG. 5. 3-methylglutaconyl-coenzyme A hydratase are enzymes which catalyze the following reaction:

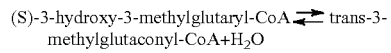

(S)-3-hydroxy-3-methylglutaryl-CoA ⇌ trans-3-methylglutaconyl-CoA+H$_2$O

This enzyme occurs in a variety of organisms, including eukaryotic and prokaryotic organisms, such as plants, animals and bacteria. The enzyme has, e.g., been described in *Catharantus roseus, Homo sapiens, Bos taurus, Ovis aries, Acinetobacter* sp., *Myxococcus* sp. and *Pseudomonas putida*. In a preferred embodiment the 3-methylglutaconyl-coenzyme A hydratase is an enzyme from *Myxococcus* sp., and even more preferably an enzyme which has an amino acid sequence as shown in SEQ ID NO: 10 or shows an amino acid sequence which is at least x % homologous to SEQ ID NO: 10 and has the activity of a 3-methylglutaconyl-coenzyme A hydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylglutaryl-CoA into 3-methylglutaconyl-CoA as set forth herein above. As regards the determination of the degree of identity, the same applies as has been set forth herein above.

The conversion of 3-hydroxy-3-methylglutaryl-CoA into 3-methylglutaconyl-CoA can also be achieved by making use of a 3-hydroxy-3-methylglutaryl-coenzyme A dehydratase activity which has been identified, e.g., in *Myxococcus xanthus* and which is encoded by the liuC gene (Li et al., Angew. Chem. Int. Ed. 52 (2013), 1304-1308).

Thus, the present invention also relates to a method for producing 3-hydroxy-3-methylbutyric acid from 3-hydroxy-3-methylglutaryl-CoA in which 3-hydroxy-3-methylglutaryl-CoA is first converted into 3-methylglutaconyl-CoA which is then converted by a decarboxylation reaction into 3-methylcrotonyl-CoA, which is then further enzymatically converted into 3-hydroxy-3-methylbutyric acid as described herein above.

The 3-hydroxy-3-methylglutaryl-CoA which is converted into 3-methylglutaconyl-CoA can itself be provided enzymatically, e.g. by the condensation of acetyl-CoA and acetoacetyl-CoA, a reaction which is naturally catalyzed by the enzyme 3-hydroxy-3-methylglutaryl-CoA synthase (also referred to as HMG-CoA synthase). HMG-CoA synthases are classified in EC 2.3.3.10 (formerly, HMG-CoA synthase has been classified as EC 4.1.3.5 but has been transferred to EC 2.3.3.10). The term "HMG-CoA synthase" refers to any enzyme which is able to catalyze the reaction where acetyl-CoA condenses with acetoacetyl-CoA to form 3-hydroxy-3-methylglutaryl-CoA (HMG-CoA) (see FIG. 6). HMG-CoA synthase is part of the mevalonate pathway. Two pathways have been identified for the synthesis of isopentenyl pyrophosphate (IPP), i.e. the mevalonate pathway and the glyceraldehyde 3-phosphate-pyruvate pathway. HMG-CoA synthase catalyzes the biological Claisen condensation of acetyl-CoA with acetoacetyl-CoA and is a member of a superfamily of acyl-condensing enzymes that includes beta-ketothiolases, fatty acid synthases (beta-ketoacyl carrier protein synthase) and polyketide synthases.

HMG-CoA synthase has been described for various organisms. Also amino acid and nucleic acid sequences encoding HMG-CoA synthases from numerous sources are available. Generally, the sequences only share a low degree of overall sequence identity. For example, the enzymes from *Staphylococcus* or *Streptococcus* show only about 20% identity to those of human and avian HMG-CoA synthase. In some sources it is reported that the bacterial HMG-CoA synthases and their animal counterparts exhibit only about 10% overall sequence identity (Sutherlin et al., J. Bacteriol. 184 (2002), 4065-4070). However, the amino acid residues involved in the acetylation and condensation reactions are conserved among bacterial and eukaryotic HMG-CoA synthases (Campobasso et al., J. Biol. Chem. 279 (2004), 44883-44888). The three-dimensional structure of three HMG-CoA synthase enzymes has been determined and the amino acids crucial for the enzymatic reaction are in principle well characterized (Campobasso et al., loc. cit.; Chun et al., J. Biol. Chem. 275 (2000), 17946-17953; Nagegowda et al., Biochem. J. 383 (2004), 517-527; Hegardt, Biochem. J. 338 (1999), 569-582). In eukaryotes there exist two forms of the HMG-CoA synthase, i.e. a cytosolic and a mitochondrial form. The cytosolic form plays a key role in the production of cholesterol and other isoprenoids and the mitochondrial form is involved in the production of ketone bodies.

In principle any HMG-CoA synthase enzyme can be used in the context of the present invention, in particular from prokaryotic or eukaryotic organisms.

Prokaryotic HMG-CoA synthases are described, e.g., from *Staphylococcus aureus* (Campobasso et al., loc. cit.; Uniprot accession number Q9FD87), *Staphylococcus epidermidis* (Uniprot accession number Q9FD76), *Staphylococcus haemolyticus* (Uniprot accession number Q9FD82), *Enterococcus faecalis* (Sutherlin et al., loc. cit.; Unirprot accession number Q9FD7), *Enterococcus faecium* (Uniprot accession number Q9FD66), *Streptococcus pneumonia* (Uniprot accession number Q9FD56), *Streptococcus pyogenes* (Uniprot accession number Q9FD61) and *Methanobacterium thermoautotrophicum* (accession number AE000857), *Borrelia burgdorferi* (NCBI accession number BB0683). Further HMG-CoA synthases are, e.g., described in WO 2011/032934. A preferred HMG-CoA synthase is the enzyme from *Schizosaccharomyces pombe* (Uniprot P54874). In a particularly preferred embodiment, the HMG-CoA synthase employed in the method of the invention has an amino acid sequence as shown in SEQ ID NO: 16 or shows an amino acid sequence which is at least x % homologous to SEQ ID NO: 16 and has the activity of a HMG-CoA synthase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the condensation of acetyl-CoA and acetoacetyl-CoA into 3-hydroxy-3-methylglutaryl-CoA. As regards the determination of the degree of identity, the same applies as has been set forth herein above.

Thus, the present invention also relates to a method for producing 3-hydroxy-3-methylbutyric acid from acetyl-CoA and acetoacetyl-CoA in which acetyl-CoA and acetoacetyl-CoA are first condensed so as to form 3-hydroxy-3-methylglutaryl-CoA, in which 3-hydroxy-3-methylglutaryl-CoA is then converted into 3-methylglutaconyl-CoA, which is then converted by a decarboxylation reaction into 3-methylcrotonyl-CoA, which is then further enzymatically converted into 3-hydroxy-3-methylbutyric acid as described herein above.

The acetoacetyl-CoA which is used in the production of 3-hydroxy-3-methylglutaryl-CoA can itself be provided by enzymatic reactions. For example, acetoacetyl-CoA can be produced from acetyl-CoA as, e.g., described in WO 2013/057194. Thus, according to the present invention, acetyl-CoA can, for example, be converted into acetoacetyl-CoA by the following reaction:

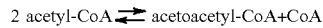

This reaction is catalyzed by enzymes called acetyl-CoA C-acetyltransferases which are classified as EC 2.3.1.9. Enzymes belonging to this class and catalyzing the above shown conversion of two molecules of acetyl-CoA into acetoacetyl-CoA and CoA occur in organisms of all kingdoms, i.e. plants, animals, fungi, bacteria etc. and have extensively been described in the literature. Nucleotide and/or amino acid sequences for such enzymes have been determined for a variety of organisms, like *Homo sapiens, Arabidopsis thaliana, E. coli, Bacillus subtilis, Clostridium acetobutylicum* and *Candida*, to name just some examples. In principle, any acetyl-CoA C-acetyltransferase (EC 2.3.1.9) can be used in the context of the present invention. In one preferred embodiment the enzyme is an acetyl-CoA acetyltransferase from *Clostridium acetobutylicum* (Uniprot P45359). In a particularly preferred embodiment, the acetyl-CoA acetyltransferase employed in the method of the invention has an amino acid sequence as shown in SEQ ID NO:

15 or shows an amino acid sequence which is at least x % homologous to SEQ ID NO: 15 and has the activity of an acetyl-CoA acetyltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting acetyl-CoA into acetoacetyl-CoA as set forth herein above.

As regards the determination of the degree of identity, the same applies as has been set forth herein above.

Alternatively, the provision of acetoacetyl-CoA may also be achieved by the enzymatic conversion of acetyl-CoA and malonyl-CoA into acetoacetyl-CoA according to the following reaction.

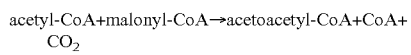

This reaction is catalyzed by an enzyme called acetoacetyl-CoA synthase (EC 2.3.1.194). The gene encoding this enzyme was identified in the mevalonate pathway gene cluster for terpenoid production in a soil-isolated Gram-positive *Streptomyces* sp. Strain CL190 (Okamura et al., PNAS USA 107 (2010), 11265-11270, 2010). Moreover a biosynthetic pathway using this enzyme for acetoacetyl-CoA production was recently developed in *E. coli* (Matsumoto K et al., Biosci. Biotechnol. Biochem, 75 (2011), 364-366). Accordingly, in a preferred embodiment, the enzymatic conversion of acetyl-CoA into said acetoacetyl-CoA consists of a single enzymatic reaction in which acetyl-CoA is directly converted into acetoacetyl-CoA. Preferably, the enzymatic conversion of acetyl-CoA into acetoacetyl-CoA is achieved by making use of an acetyl-CoA acetyltransferase (EC 2.3.1.9) as described above.

Alternatively, the acetoacetyl-CoA can also be provided by an enzymatic conversion which comprises two steps, i.e.;
(i) the enzymatic conversion of acetyl-CoA into malonyl-CoA; and
(ii) the enzymatic conversion of malonyl-CoA and acetyl-CoA into acetoacetyl-CoA.

Preferably, the enzymatic conversion of acetyl-CoA into malonyl-CoA is achieved by the use of an acetyl-CoA carboxylase (EC 6.4.1.2). This enzyme catalyzes the following reaction:

Acetyl-CoA+ATP+CO$_2$→Malonyl-CoA+ADP

Preferably, the enzymatic conversion of malonyl-CoA and acetyl-CoA into acetoacetyl-CoA is achieved by the use of an acetoacetyl-CoA synthase (EC 2.3.1.194). In principle, any acetyl-CoA acetyltransferase (EC 2.3.1.9), acetyl-CoA carboxylase (EC 6.4.1.2) and/or acetoacetyl-CoA synthase (EC 2.3.1.194) can be applied in the method according to the invention.

FIG. 7 shows schematically possible ways of producing acetoacetyl-CoA from acetyl-CoA.

Thus, the present invention also relates to a method for producing 3-hydroxy-3-methylbutyric acid from acetyl-CoA, in which acetoacetyl-CoA is produced from acetyl-CoA as described above, in which the thus produced acetoacetyl-CoA is then condensed with acetyl-CoA so as to form 3-hydroxy-3-methylglutaryl-CoA, in which 3-hydroxy-3-methylglutaryl-CoA is then converted into 3-methylglutaconyl-CoA, which is then converted by a decarboxylation reaction into 3-methylcrotonyl-CoA, which is then further enzymatically converted into 3-hydroxy-3-methylbutyric acid as described herein above.

As described above, the 3-hydroxy-3-methylbutyric acid produced according to any of the methods described above can be further converted into isobutene as described herein above. Thus, the present invention also relates to a method for producing isobutene comprising the steps of any of the methods described above and further comprising the step of converting the produced 3-hydroxy-3-methylbutyric acid into isobutene.

In another aspect, the present invention also relates to a method for the conversion of 3-methylcrotonyl-CoA into 3-hydroxy-3-methylbutyric acid comprising the steps of:
(a) enzymatically converting 3-methylcrotonyl-CoA into 3-hydroxy-3-methylbutyryl-CoA; and
(b) further enzymatically converting the thus produced 3-hydroxy-3-methylbutyryl-CoA into 3-hydroxy-3-methylbutyric acid.

According to the present invention, the conversion of 3-hydroxy-3-methylbutyryl-CoA into 3-hydroxy-3-methylbutyric acid can be achieved by a direct conversion. In another embodiment, the conversion of 3-hydroxy-3-methylbutyryl-CoA into 3-hydroxy-3-methylbutyric acid can be achieved by a conversion which first encompasses the conversion of 3-hydroxy-3-methylbutyryl-CoA into 3-hydroxy-3-methylbutyryl phosphate, and the subsequent conversion of 3-hydroxy-3-methylbutyryl phosphate into 3-hydroxy-3-methylbutyric acid.

According to the present invention the enzymatic conversion of 3-methylcrotonyl-CoA into 3-hydroxy-3-methylbutyryl-CoA according to step (a) of the above described method can, for example be achieved by the use of
(i) a 3-hydroxypropionyl-CoA dehydratase (EC 4.2.1.116);
(ii) a 3-hydroxybutyryl-CoA dehydratase (EC 4.2.1.55);
(iii) an enoyl-CoA hydratase (EC 4.2.1.17);
(iv) a 3-hydroxyoctanoyl-[acyl-carrier-protein] dehydratase (EC 4.2.1.59);
(v) a crotonyl-[acyl-carrier-protein] hydratase (EC 4.2.1.58);
(vi) a 3-hydroxydecanoyl-[acyl-carrier-protein] dehydratase (EC 4.2.1.60);
(vii) a 3-hydroxypalmitoyl-[acyl-carrier-protein] dehydratase (EC 4.2.1.61);
(viii) a long-chain-enoyl-CoA hydratase (EC 4.2.1.74);
(ix) a 3-methylglutaconyl-CoA hydratase (EC 4.2.1.18).

The conversion of 3-methylcrotonyl-CoA into 3-hydroxy-3-methylbutyryl-CoA is schematically shown in FIG. 8.

The enzymes mentioned in items (i) to (ix) are characterized in that they use a natural substrate having the following minimal structural motif:

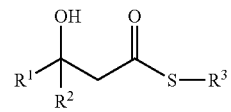

wherein
$R^1$ is a hydrogen atom or an alkyl group or $CH_2COO^-$,
$R^2$ is a hydrogen atom or a methyl group; and
$R^3$ is coenzyme A or acyl-carrier protein.

Thus, the above mentioned enzymes can be divided into two groups as follows:
I. $R_3$ in the above shown formula is acyl-carrier protein
This group includes EC 4.2.1.58, EC 4.2.1.59, EC 4.2.1.60 and EC 4.2.1.61.
The enzymes of this group have in common that they catalyze a reaction of the following type:

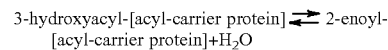

The enzymes of this group share a common structural motif which is referenced in the InterPro as InterPro IPR013114 (http://www.ebi.ac.uk/interpro/entry/IPR013114). The accession number for these enzymes in the Pfam database is PF 07977 (http://pfam.sanger.ac.uk/family/PF07977).

II. R₃ in the above shown formula is coenzyme A

This group includes EC 4.2.1.116, EC 4.2.1.55, EC 4.2.1.17, EC 4.2.1.74 and EC 4.2.1.18

The enzymes of this group share a common structural motif which is referenced in the InterPRO database as InterPro IPR001753 (http://www.ebi.ac.uk/interpro/entry/IPR001753) and IPR0018376 (http://www.ebi.ac.uk/interpro/entry/IPR018376). The accession number for these enzymes in the Pfam database is PF00378 (http://pfam.sanger.ac.uk/family/PF00378).

In one embodiment of the method according to the invention the conversion of 3-methylcrotonyl-CoA into 3-hydroxy-3-methylbutyryl-CoA is achieved by the use of a 3-hydroxypropionyl-CoA dehydratase (EC 4.2.1.116). 3-hydroxypropionyl-CoA dehydratases (EC 4.2.1.116) catalyze the following reaction:

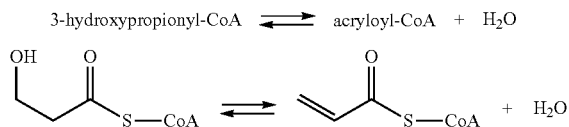

The enzyme is known from various bacteria and archae. Thus, in a preferred embodiment of the invention a bacterial 3-hydroxypropionyl-CoA dehydratase (EC 4.2.1.116) is used, preferably a 3-hydroxypropionyl-CoA dehydratase from a bacterium or an archaebacterium of a genus selected from the group consisting of *Metallosphaera*, *Sulfolobus* and *Brevibacillus* and most preferably from a species selected from the group consisting of *Metallosphaera cuprina*, *Metallosphaera sedula*, *Sulfolobus tokodaii* and *Brevibacillus laterosporus*. Examples for such bacterial 3-hydroxypropionyl-CoA dehydratases are the enzymes from *Metallosphaera cuprina* (Uniprot F4FZ85; SEQ ID NO:1), *Metallosphaera sedula* (Uniprot A4YI89, Teufel et al., J. Bacteriol. 191 (2009), 4572-4581; SEQ ID NO:3), *Sulfolobus tokodaii* (Uniprot F9VNG3; SEQ ID NO:2) and *Brevibacillus laterosporus* (Uniprot F7TTZ1; SEQ ID NO:6). Amino acid and nucleotide sequences for these enzymes are available.

In a preferred embodiment, the 3-hydroxypropionyl-CoA dehydratase employed in the method of the invention has an amino acid sequence as shown in any one of SEQ ID NOs: 1 to 3 or 6 or shows an amino acid sequence which is at least x % homologous to any one of SEQ ID NOs: 1 to 3 or 6 and has the activity of a 3-hydroxypropionyl-CoA dehydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-CoA into 3-hydroxy-3-methylbutyryl-CoA as set forth herein above.

As regards the determination of the degree of identity, the same applies as has been set forth herein above.

In another embodiment of the method according to the invention the conversion of 3-methylcrotonyl-CoA into 3-hydroxy-3-methylbutyryl-CoA is achieved by the use of a 3-hydroxybutyryl-CoA dehydratase (EC 4.2.1.55). 3-hydroxybutyryl-CoA dehydratases (EC 4.2.1.55) catalyze the following reaction:

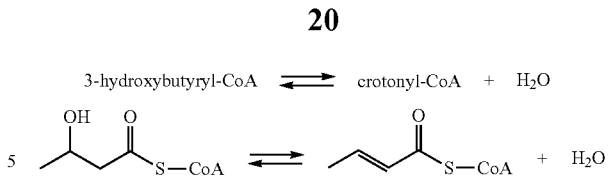

This reaction corresponds to a Michael elimination. 3-hydroxybutyryl-CoA dehydratase belongs to the family of lyases, specifically the hydro-lyases, which cleave carbon-oxygen bonds. The systematic name of this enzyme class is (3R)-3-hydroxybutanoyl-CoA hydro-lyase (crotonoyl-CoA-forming). Other names in common use include D-3-hydroxybutyryl coenzyme A dehydratase, D-3-hydroxybutyryl-CoA dehydratase, enoyl coenzyme A hydratase, and (3R)-3-hydroxybutanoyl-CoA hydro-lyase. This enzyme participates in the butanoate metabolism. Enzymes belonging to this class and catalyzing the above shown conversion of 3-hydroxybutyryl-Coenzyme A into crotonyl-Coenzyme A have been described to occur, e.g. in rat (*Rattus norvegicus*), in *Rhodospirillum rubrum*, in *Myxococcus xanthus*, *Myxococcus fulvus*, *Myxococcus stipitatus*, in *Corallococcus coralloides*, in *Stigmatella auranticaca*, in *Sulfolobus acidocaldarius* and in *Acidianus hospitalis*. Nucleotide and/or amino acid sequences for such enzymes have been determined, e.g. also for In principle, any 3-hydroxybutyryl-CoA dehydratase (EC 4.2.1.55) which can catalyze the conversion of 3-methylcrotonyl-CoA into 3-hydroxy-3-methylbutyryl-CoA can be used in the context of the present invention. In a preferred embodiment of the invention a 3-hydroxybutyryl-CoA dehydratase from an archaebacterium is used, preferably a 3-hydroxybutyryl-CoA dehydratase from an archaebacterium of a genus selected from the group consisting of *Sulfolobus* and *Acidianus* and most preferably from a species selected from the group consisting of *S. acidocaldarius* and *Acidianus hospitalis*. Examples for such bacterial 3-hydroxybutyryl-CoA dehydratases are the enzymes from *Sulfolobus acidocaldarius* (Uniprot Q4J8D5; SEQ ID NO: 4) and from *Acidianus hospitalis* ((Uniprot F4B9R3; SEQ ID NO: 5). In another preferred embodiment a 3-hydroxybutyryl-CoA dehydratase from a bacterium of the genus *Myxococcus*, *Corallococcus* or *Stigmatella* is used, preferably of the species *Myxococcus xanthus*, *Myxococcus fulvus*, *Myxococcus stipitatus*, *Corallococcus coralloides* or *Stigmatella aurantiaca*. Examples for such bacterial 3-hydroxybutyryl-CoA dehydratases are the enzymes from *Myxococcus xanthus* (Uniprot Q1D5Y4, SEQ ID NO: 7), *Myxococcus fulvus* (Uniprot F8CDH2; SEQ ID NO: 11), *Myxococcus stipitatus* (Uniprot L7U993; SEQ ID NO: 12), *Corallococcus coralloides* (Uniprot H8N0F4; SEQ ID NO: 13) or *Stigmatella aurantiaca* (Uniprot Q08YS1, SEQ ID NO: 14).

In a preferred embodiment, the 3-hydroxybutyryl-CoA dehydratase employed in the method of the invention has an amino acid sequence as shown in any one of SEQ ID NOs: 4, 5, 7 or 11 to 14 or shows an amino acid sequence which is at least x % homologous to any one of SEQ ID NOs: 4, 5, 7 or 11 to 14 and has the activity of a 3-hydroxybutyryl-CoA dehydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-CoA into 3-hydroxy-3-methylbutyryl-CoA as set forth herein above.

As regards the determination of the degree of identity, the same applies as has been set forth herein above.

In another embodiment of the method according to the invention the conversion of 3-methylcrotonyl-CoA into 3-hydroxy-3-methylbutyryl-CoA is achieved by the use of an enoyl-CoA hydratase (EC 4.2.1.17). Enoyl-CoA hydratases (EC 4.2.1.17) catalyze the following reaction:

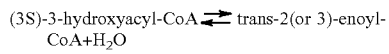
(3S)-3-hydroxyacyl-CoA ⇌ trans-2(or 3)-enoyl-CoA+H₂O

Enoyl-CoA hydratase is an enzyme that normally hydrates the double bond between the second and third carbon atoms on acyl-CoA. However, it can also be employed to catalyze the reaction in the reverse direction. This enzyme, also known as crotonase, is naturally involved in metabolizing fatty acids to produce both acetyl-CoA and energy. Enzymes belonging to this class have been described to occur, e.g. in rat (*Rattus norvegicus*), humans (*Homo sapiens*), mouse (*Mus musculus*), wild boar (*Sus scrofa*), *Bos taurus, E. coli, Clostridium acetobutylicum* and *Clostridium aminobutyricum*. Nucleotide and/or amino acid sequences for such enzymes have been determined, e.g. for rat, humans and *Bacillus subtilis* and *Bacillus anthracis*. In principle, any enoyl-CoA hydratase (EC 4.2.1.17) which can catalyze the conversion of 3-methylcrotonyl-CoA into 3-hydroxy-3-methylbutyryl-CoA can be used in the context of the present invention. In a preferred embodiment the enoyl-CoA hydratase is an enoyl-CoA hydratase of *Galactomyces reessii* (Dhar et al., J. Ind. Microbiol. Biotechnol. 28 (2002), 81-87), an enoyl-CoA hydratase of *Bacillus subtilis* (Uniprot G4PBC3; SEQ ID NO: 8) or an enoyl-CoA hydratase of *Bacillus anthracis* (Uniprot Q81YG6; SEQ ID NO: 9).

In a preferred embodiment, the enoyl-CoA hydratase employed in the method of the invention has an amino acid sequence as shown in any one of SEQ ID NOs: 8 or 9 or shows an amino acid sequence which is at least x % homologous to any one of SEQ ID NOs: 8 or 9 and has the activity of an enoyl-CoA hydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-methylcrotonyl-CoA into 3-hydroxy-3-methylbutyryl-CoA as set forth herein above. As regards the determination of the degree of identity, the same applies as has been set forth herein above.

In another embodiment of the method according to the invention the conversion of 3-methylcrotonyl-CoA into 3-hydroxy-3-methylbutyryl-CoA is achieved by the use of a 3-hydroxyoctanoyl-[acyl-carrier-protein] dehydratase (EC 4.2.1.59). 3-hydroxyoctanoyl-[acyl-carrier-protein] dehydratases (EC 4.2.1.59) catalyze the following reaction:

(3R)-3-hydroxyoctanoyl-[acyl-carrier protein] ⇌ oct-2-enoyl-[acyl-carrier protein]+H₂O This enzyme belongs to the family of lyases, specifically the hydro-lyases, which cleave carbon-oxygen bonds. The systematic name of this enzyme class is (3R)-3-hydroxyoctanoyl-[acyl-carrier-protein] hydro-lyase (oct-2-enoyl-[acyl-carrier protein]-forming). Other names in common use include D-3-hydroxyoctanoyl-[acyl carrier protein] dehydratase, D-3-hydroxyoctanoyl-acyl carrier protein dehydratase, beta-hydroxyoctanoyl-acyl carrier protein dehydrase, beta-hydroxyoctanoyl thioester dehydratase, beta-hydroxyoctanoyl-ACP-dehydrase, and (3R)-3-hydroxyoctanoyl-[acyl-carrier-protein] hydro-lyase. 3-hydroxyoctanoyl-[acyl-carrier-protein] dehydratases has been described to exist, e.g., in *E. coli* (Mizugaki et al., Biochem. Biophys. Res. Commun. 33 (1968), 520-527). In principle, any 3-hydroxyoctanoyl-[acyl-carrier-protein] dehydratase which can catalyze the conversion of 3-methylcrotonyl-CoA into 3-hydroxy-3-methylbutyryl-CoA can be used in the context of the present invention. In a preferred embodiment the enzyme from *E. coli* is used in a method according to the present invention.

In another embodiment of the method according to the invention the conversion of 3-methylcrotonyl-CoA into 3-hydroxy-3-methylbutyryl-CoA is achieved by the use of a crotonoyl-[acyl-carrier-protein] hydratase (EC 4.2.1.58). Crotonoyl-[acyl-carrier-protein] hydratases (EC 4.2.1.58) catalyze the following reaction:

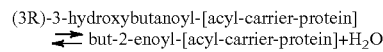
(3R)-3-hydroxybutanoyl-[acyl-carrier-protein] ⇌ but-2-enoyl-[acyl-carrier-protein]+H₂O This enzyme belongs to the family of lyases, specifically the hydro-lyases, which cleave carbon-oxygen bonds.

Other names in common use include (3R)-3-hydroxybutanoyl-[acyl-carrier-protein] hydro-lyase, beta-hydroxybutyryl acyl carrier protein dehydratase, beta-hydroxybutyryl acyl carrier protein (ACP) dehydratase, beta-hydroxybutyryl acyl carrier protein dehydratase, enoyl acyl carrier protein hydratase, crotonyl acyl carrier protein hydratase, 3-hydroxybutyryl acyl carrier protein dehydratase, beta-hydroxybutyryl acyl carrier, and protein dehydratase. This enzyme participates in fatty acid biosynthesis. Crotonoyl-[acyl-carrier-protein] hydratase has been described to exist, e.g., in *E. coli* and *Arabidopsis thaliana*. In principle, any crotonoyl-[acyl-carrier-protein] hydratase which can catalyze the conversion of 3-methylcrotonyl-CoA into 3-hydroxy-3-methylbutyryl-CoA can be used in the context of the present invention. In a preferred embodiment the enzyme from *E. coli* is used in a method according to the present invention.

In another embodiment of the method according to the invention conversion of 3-methylcrotonyl-CoA into 3-hydroxy-3-methylbutyryl-CoA is achieved by the use of a 3-hydroxydecanoyl-[acyl-carrier-protein] dehydratase (EC 4.2.1.60). 3-hydroxydecanoyl-[acyl-carrier-protein] dehydratases (EC 4.2.1.60) catalyze the following reactions:

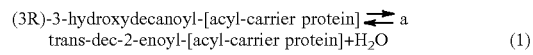
(3R)-3-hydroxydecanoyl-[acyl-carrier protein] ⇌ a trans-dec-2-enoyl-[acyl-carrier protein]+H₂O    (1)

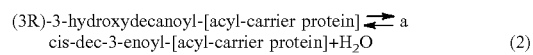
(3R)-3-hydroxydecanoyl-[acyl-carrier protein] ⇌ a cis-dec-3-enoyl-[acyl-carrier protein]+H₂O    (2)

The enzyme has been described to exist, e.g., in *Pseudomonas aeruginosa, Pseudomonas fluorescens, Toxoplasma gondii, Plasmodium falciparum, Helicobacter pylori, Corynebacterium ammoniagenes, Enterobacter aerogenes, E. coli, Proteus vulgaris* and *Salmonella enterica*. In principle, any 3-hydroxydecanoyl-[acyl-carrier-protein] dehydratase which can catalyze the conversion of 3-methylcrotonyl-CoA into 3-hydroxy-3-methylbutyryl-CoA can be used in the context of the present invention. In a preferred embodiment the enzyme from *E. coli* is used in a method according to the present invention.

In another embodiment of the method according to the invention the conversion of 3-methylcrotonyl-CoA into 3-hydroxy-3-methylbutyryl-CoA is achieved by the use of a 3-hydroxypalmitoyl-[acyl-carrier-protein] dehydratase (EC 4.2.1.61). 3-hydroxypalmitoyl-[acyl-carrier-protein] dehydratases (EC 4.2.1.61) catalyze the following reaction:

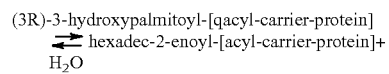
(3R)-3-hydroxypalmitoyl-[qacyl-carrier-protein] ⇌ hexadec-2-enoyl-[acyl-carrier-protein]+H₂O This enzyme belongs to the family of lyases, specifically the hydro-lyases, which cleave carbon-oxygen bonds. Other names in common use include D-3-hydroxypalmitoyl-[acyl-carrier-protein] dehydratase, beta-hydroxypalmitoyl-acyl carrier protein dehydratase, beta-hydroxypalmitoyl thioester dehydratase, beta-hydroxypalmityl-ACP dehydratase, and (3R)-3-hydroxypalmitoyl-[acyl-carrier-protein] hydro-lyase. 3-hydroxypalmitoyl-[acyl-carrier-protein] dehydratase has been described to exist, e.g., in *Candida albicans, Yarrowia lipolytica, S. cerevisiae, S. pombe, Cochliobolus carbonum, Mus musculus, Rattus norvegicus, Bos taurus, Gallus gallus* and *Homo sapiens*. In principle, any 3-hydroxypalmitoyl-[acyl-carrier-protein] dehydratase which can catalyze the conversion of 3-methylcrotonyl-CoA into 3-hydroxy-3-methylbutyryl-CoA can be used in the context of the present invention.

In another embodiment of the method according to the invention the conversion of 3-methylcrotonyl-CoA into 3-hydroxy-3-methylbutyryl-CoA is achieved by the use of a long-chain-enoyl-CoA hydratase (EC 4.2.1.74). Long-chain-enoyl-CoA hydratases (EC 4.2.1.74) catalyze the following reaction:

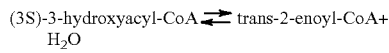
(3S)-3-hydroxyacyl-CoA ⇌ trans-2-enoyl-CoA+ H₂O

This enzyme belongs to the family of lyases, specifically the hydro-lyases, which cleave carbon-oxygen bonds. The systematic name of this enzyme class is long-chain-(3S)-3-hydroxyacyl-CoA hydro-lyase. This enzyme is also called long-chain enoyl coenzyme A hydratase and it participates in fatty acid elongation in mitochondria and fatty acid metabolism. This enzyme occurs in a number of organisms, e.g., in *Rattus norvegicus* (Wu et al., Org. Lett. 10 (2008), 2235-2238), *Sus scrofa* and *Cavia porcellus* (Fong and Schulz, J. Biol. Chem. 252 (1977), 542-547; Schulz, Biol. Chem. 249 (1974), 2704-2709) and in principle any long-chain-enoyl-CoA hydratase which can catalyze the conversion of 3-methylcrotonyl-CoA into 3-hydroxy-3-methylbutyryl-CoA can be employed in the method of the invention.

In another embodiment of the method according to the invention the conversion of 3-methylcrotonyl-CoA into 3-hydroxy-3-methylbutyryl-CoA is achieved by the use of a 3-methylglutaconyl-CoA hydratase (EC 4.2.1.18). 3-methylglutaconyl-CoA hydratases (EC 4.2.1.18) catalyze the following reaction:

(S)-3-hydroxymethylglutaryl-CoA ⇌ trans-3-methylglutaconyl-CoA + H₂0

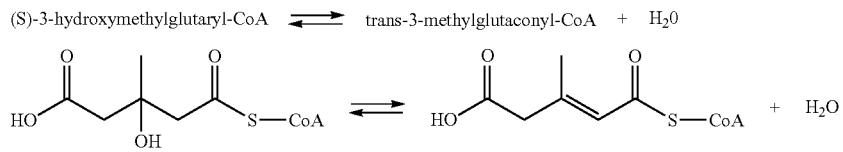

This enzyme occurs in a number of organisms in particular in bacteria, plants and animals. The enzyme has been described, e.g., for *Pseudomonas putida, Acinetobacter* sp. (SwissProt accession number Q3HW12), *Catharanthus roseus, Homo sapiens* (SwissProt accession number Q13825), *Bos taurus* and *Ovis aries* and in principle any 3-methylglutaconyl-CoA hydratase which can catalyze the conversion of 3-methylcrotonyl-CoA into 3-hydroxy-3-methylbutyryl-CoA can be employed in the method of the invention.

In a preferred embodiment the enzyme used for converting 3-methylcrotonyl-CoA into 3-hydroxy-3-methylbutyryl-CoA is the protein encoded by the liuC gene of *Myxococcus xanthus* (Li et al., Angew. Chem. Int. Ed. 52 (2013), 1304-1308).

As mentioned above, the produced 3-hydroxy-3-methylbutyryl-CoA can be further enzymatically converted into 3-hydroxy-3-methylbutyric acid (step (b)). This conversion can either be achieved by a direct conversion or, alternatively, by a two-step reaction via 3-hydroxy-3-methylbutyryl phosphate.

In a first embodiment the 3-hydroxy-3-methylbutyryl-CoA is directly converted into 3-hydroxy-3-methylbutyric acid.

The enzymatic conversion of the produced 3-hydroxy-3-methylbutyryl-CoA into 3-hydroxy-3-methylbutyric acid can, e.g., be achieved by making use of (i) a thioesterase (EC 3.1.2); or
(ii) a CoA-transferase (EC 2.8.3).

The conversion of 3-hydroxy-3-methylbutyryl-CoA into 3-hydroxy-3-methylbutyric acid catalyzed by a thioesterase is schematically shown in FIG. 9. The conversion of 3-hydroxy-3-methylbutyryl-CoA into 3-hydroxy-3-methylbutyric acid catalyzed by a CoA-transferase is schematically shown in FIG. 10.

Thioesterases and CoA-transferases have already been described above in detail and the same applies here.

In connection with the CoA-transferases to be used in the context of the described conversion of 3-hydroxy-3-methylbutyryl-CoA into 3-hydroxy-3-methylbutyric acid it is added here that in a preferred embodiment a CoA-transferase is used which belongs to family I or II as described herein-above and, in particular, the α-subunit of the enzyme complex. In more preferred embodiments the CoA-transferase is an a subunit of a citrate lyase (EC 2.8.3.10) citramalate CoA-transferase (EC 2.8.3.11) or a succinyl-CoA:acetate CoA-transferase (EC 2.8.3.18; see also Mullins et al., Biochemistry 51(2012), 8422-34; Mullins et al., J. Bacteriol. 190 (2006), 4933-4940).

Citramalate CoA-transferase (EC 2.8.3.11) is an enzyme which catalyzes the following reaction:

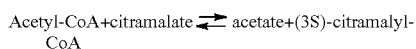
Acetyl-CoA+citramalate ⇌ acetate+(3S)-citramalyl-CoA

The enzyme has been described to occur, e.g., in *Achromobacter xylosoxidans* and *Clostridium tetanomorphum*. In particular, the α subunit of the enzyme complex citramalate lyase from *Clostridium tetanomorhum* was demonstrated to catalyze the formation of acetyl-CoA and citramalate from citramalyl-CoA and acetate (Dimroth et al., Eur. J. Biochem. 80 (1977), 479-477).

Succinyl-CoA:acetate CoA-transferase is an enzyme which catalyzes the following reaction:

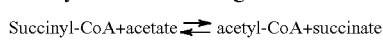
Succinyl-CoA+acetate ⇌ acetyl-CoA+succinate

The enzyme has been described to occur, e.g., in *Acetobacter aceti, Tritrichomonas foetus, Trichomonas vaginalis* and *Trypanosoma brucei*.

In a second embodiment 3-hydroxy-3-methylbutyryl-CoA is first converted into 3-hydroxy-3-methylbutyryl phosphate which is then further converted into 3-hydroxy-3-methylbutyric acid. The reaction can be summarized as follows:

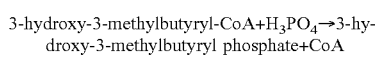
3-hydroxy-3-methylbutyryl-CoA+H₃PO₄→3-hydroxy-3-methylbutyryl phosphate+CoA     (i)

3-hydroxy-3-methylbutyryl phosphate+ADP→3-hydroxy-3-methylbutyric acid+ATP     (ii)

Thus, the present invention also provides a method for the conversion of 3-methylcrotonyl-CoA into 3-hydroxy-3-methylbutyric acid comprising the steps of
(a) enzymatically converting 3-methylcrotonyl-CoA into 3-hydroxy-3-methylbutyryl-CoA; and
(b) further enzymatically converting the thus produced 3-hydroxy-3-methylbutyryl-CoA into 3-hydroxy-3-methylbutyryl phosphate; and
(c) further enzymatically converting the thus produced hydroxy-3-methylbutyryl phosphate into 3-hydroxy-3-methylbutyric acid The conversion of 3-hydroxy-3-methylbutyryl-CoA into 3-hydroxy-3-methylbutyryl phosphate can, e.g., be achieved by the use of a phosphate butyryltransferase (EC 2.3.1.19) or a phosphate acetyltransferase (EC 2.3.1.8).

Phosphate butyryltransferase (EC 2.3.1.19) naturally catalyzes the following reaction Butyryl-CoA+$H_3PO_4$ ⇌ butyryl phosphate+CoA It has been described by Wiesenborn et al. (Appl. Environ. Microbiol. 55 (1989), 317-322) and by Ward et al. (J. Bacteriol. 181 (1999), 5433-5442) that phosphate butyryltransferases (EC 2.3.1.19) can use a number of substrates in addition to butyryl coenzyme A (butyryl-CoA), in particular acetyl-CoA, propionyl-CoA, isobutyryl-CoA, valeryl-CoA and isovaleryl-CoA.

The enzyme has been described to occur in a number of organisms, in particular in bacteria and in protozoae. In one embodiment the enzyme is from the protozoae *Dasytricha ruminantium*. In a preferred embodiment the phosphate butyryltransferase is a phosphate butyryltransferase from a bacterium, preferably from a bacterium of the genus *Bacillus, Butyrivibrio, Enterococcus* or *Clostridium*, more preferably *Enterococcus* or *Clostridium*, and even more preferably from *Bacillus megaterium, Bacillus subtilis, Butyrivibrio fibrisolvens, Clostridium acetobutylicum, Clostridium beijerinckii, Clostridium butyricum, Clostridium kluyveri, Clostridium saccharoacetobutylicum, Clostridium sprorogenes* or *Enterococcus faecalis*. Most preferably, the enzyme is from *Bacillus subtilis* (strain 168) (Uniprot Accession number P54530), *Clostridium acetobutylicum* (Uniprot Accession number F0K6W0) or from *Enterococcus faecalis* MTUP9 (Uniprot Accession number K4YRE8 or Uniprot Accession number A0A038BNC2). The sequences available for the phosphate butyryltransferase from *Enterococcus faecalis* under Uniprot Accession number K4YRE8 and Uniprot Accession number A0A038BNC2 have a sequence homology of 99.3%. The sequences available for the phosphate butyryltransferase from *Enterococcus faecalis* under Uniprot Accession number A0A038BNC2 is the more preferred one.

As mentioned, in a preferred embodiment, the enzyme is a phosphate butyryltransferase (EC 2.3.1.19) from *Bacillus subtilis* (strain 168) (Uniprot Accession number P54530). In a particularly preferred embodiment, the phosphate butyryltransferase (EC 2.3.1.19) employed in the method of the invention has an amino acid sequence as shown in SEQ ID NO: 28 or shows an amino acid sequence which is at least x % homologous to SEQ ID NO: 28 and has the activity of a phosphate butyryltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylbutyryl-CoA into 3-hydroxy-3-methylbutyryl phosphate as set forth herein above.

In another preferred embodiment, as mentioned, the enzyme is a phosphate butyryltransferase (EC 2.3.1.19) from *Enterococcus faecalis* MTUP9 (Uniprot Accession number K4YRE8 or Uniprot Accession number A0A038BNC2). In a particularly preferred embodiment, the phosphate butyryltransferase (EC 2.3.1.19) employed in the method of the invention has an amino acid sequence as shown in SEQ ID NO: 29 or shows an amino acid sequence which is at least x % homologous to SEQ ID NO: 29 and has the activity of a phosphate butyryltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylbutyryl-CoA into 3-hydroxy-3-methylbutyryl phosphate as set forth herein above.

As regards the determination of the degree of identity, the same applies as has been set forth herein above.

Phosphate acetyltransferase (EC 2.3.1.8) naturally catalyzes the following reaction Acetyl-CoA+$H_3PO_4$ ⇌ acetyl phosphate+CoA It has been described by Veit et al. (J. Biotechnol. 140 (2009), 75-83) that phosphate acetyltransferase can also use as a substrate butyryl-CoA or propionyl-CoA.

The accession numbers for this enzyme family in InterPro database are IPR012147 and IPR002505 (http://www.ebi.ac.uk/interpro/entry/IPR012147 http://www.ebi.ac.uk/interpro/entry/IPR002505)
See also http://pfam.sanger.ac.uk/family/PF01515

The enzyme has been described in a variety of organisms, in particular bacteria and fungi. Thus, in one preferred embodiment the enzyme is an enzyme from a bacterium, preferably of the genus *Escherichia, Chlorogonium, Clostridium, Veillonella, Methanosarcina, Corynebacterium, Ruegeria, Salmonella, Azotobacter, Bradorhizobium, Lactobacillus, Moorella, Rhodopseudomonas, Sinorhizobium, Streptococcus, Thermotoga* or *Bacillus*, more preferably of the species *Escherichia coli, Chlorogonium elongatum, Clostridium kluyveri, Clostridium acetobutylicum, Clostridium acidurici, Veillonella parvula, Methanosarcina thermophila, Corynebacterium glutamicum, Ruegeria pomeroyi, Salmonella enterica, Azotobacter vinelandii, Bradyrhizobium japonicum, Lactobacillus fermentum, Lactobacillus sanfranciscensis, Moorella thermoacetica, Rhodopseudomonas palustris, Sinorhizobium meliloti, Streptococcus pyogenes, Thermotoga maritima* or *Bacillus subtilis*. In another preferred embodiment the enzyme is an enzyme from a fungus, preferably from the genus *Saccharomyces*, more preferably of the species *Saccharomyces cerevisiae*.

The conversion of 3-hydroxy-3-methylbutyryl phosphate into 3-hydroxy-3-methylbutyric acid can, e.g., be achieved by the use of a butyrate kinase (EC 2.7.2.7), a branched-chain-fatty-acid kinase (EC 2.7.2.14), a propionate kinase (EC 2.7.2.15) or an acetate kinase (EC 2.7.2.1).

Butyrate kinases (EC 2.7.2.7) naturally catalyze the following reaction

Butyrate+ATP ⇌ butyryl phosphate+ADP

It has been described, e.g. by Hartmanis (J. Biol. Chem. 262 (1987), 617-621) that butyrate kinase can use a number of substrates in addition to butyrate, e.g. valerate, isobutyrate, isovalerate and vinyl acetate. The enzyme has been described in a variety of organisms, in particular bacteria. In one preferred embodiment the enzyme is from a bacterium, preferably from a bacterium of the genus *Clostridium, Butyrivibrio, Thermotoga, Enterococcus, Lactobacillus* or

*Geobacillus*. Preferred is *Clostridium*, *Lactobacillus* or *Geobacillus*. More preferably the enzyme is from a bacterium of the species *Clostridium acetobutylicum*, *Clostridium proteoclasticum*, *Clostridium tyrobutyricum*, *Clostridium butyricum*, *Clostridium pasteurianum*, *Clostridium tetanomorphum*, *Butyrivibrio firbrosolvens*, *Butyrivibrio hungatei*, *Thermotoga maritime*, *Enterococcus durans*, *Lactobacillus casei* (Uniprot Accession number K0N529) or *Geobacillus* sp. (Uniprot Accession number L8A0E1). Preferred is *Clostridium acetobutylicum*, *Lactobacillus casei* W56 or *Geobacillus* sp. GHH01. For *Clostridium acetobutylicum*, two butyrate kinases have been described: butyrate kinase 1 (Uniprot Accession number: Q45829) and butyrate kinase II (Uniprot Accession number: Q97I19).

As mentioned, in a preferred embodiment, the enzyme is a butyrate kinase (EC 2.7.2.7) from *Lactobacillus casei* W56 (Uniprot Accession number K0N529). In a particularly preferred embodiment, the butyrate kinase (EC 2.7.2.7) employed in the method of the invention has an amino acid sequence as shown in SEQ ID NO: 30 or shows an amino acid sequence which is at least x % homologous to SEQ ID NO: 30 and has the activity of a butyrate kinase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylbutyryl phosphate into 3-hydroxy-3-methylbutyric acid as set forth herein above.

In another preferred embodiment, the enzyme is a butyrate kinase (EC 2.7.2.7) from *Geobacillus* sp. GHH01 (Uniprot Accession number L8A0E1). In a particularly preferred embodiment, the butyrate kinase (EC 2.7.2.7) employed in the method of the invention has an amino acid sequence as shown in SEQ ID NO: 31 or shows an amino acid sequence which is at least x % homologous to SEQ ID NO: 31 and has the activity of a butyrate kinase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylbutyryl phosphate into 3-hydroxy-3-methylbutyric acid as set forth herein above.

Branched-chain-fatty-acid kinases (EC 2.7.2.14) naturally catalyze the following reaction

2-methylpropanoate+ATP ⇌ 2-methylpropanoyl phosphate+ADP

This enzyme has been described to occur in a number of bacteria. Thus, in one preferred embodiment the enzyme is an enzyme from a bacterium, preferably of the genus *Spirochaeta* or *Thermotoga*, more preferably *Thermotoga* maritime.

Propionate kinases (EC 2.7.2.15) naturally catalyze the following reactions

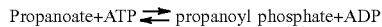

Propanoate+ATP ⇌ propanoyl phosphate+ADP

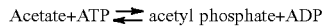

Acetate+ATP ⇌ acetyl phosphate+ADP

This enzyme has been described to occur in a number of bacteria, in particular Enterobacteriacea. Thus, in one preferred embodiment the enzyme is an enzyme from a bacterium, preferably of the genus *Salmonella* or *Escherichia*, more preferably of the species *Salmonella enterica* or *Escherichia coli*.

Acetate kinases (EC 2.7.2.1) naturally catalyze the following reaction

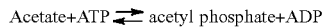

Acetate+ATP ⇌ acetyl phosphate+ADP

This enzyme has been described to occur in a number of organisms, in particular bacteria and eukaryotes. In one preferred embodiment the enzyme is from a bacterium, preferably from a bacterium of the genus *Methanosarcina*, *Cryptococcus*, *Ethanoligenens*, *Propionibacterium*, *Roseovarius*, *Streptococcus*, *Salmonella*, *Acholeplasma*, *Acinetobacter*, *Ajellomyces*, *Bacillus*, *Borrelia*, *Chaetomium*, *Clostridium*, *Coccidioides*, *Coprinopsis*, *Cryptococcus*, *Cupriavidus*, *Desulfovibrio*, *Enterococcus*, *Escherichia*, *Ethanoligenes*, *Geobacillus*, *Helicobacter*, *Lactobacillus*, *Lactococcus*, *Listeria*, *Mesoplasma*, *Moorella*, *Mycoplasma*, *Oceanobacillus*, *Propionibacterium*, *Rhodospeudomonas*, *Roseovarius*, *Salmonella*, *Staphylococcus*, *Thermotoga* or *Veillonella*, more preferably from a bacterium of the species *Methanosarcina thermophila*, *Cryptococcus neoformans*, *Ethanoligenens harbinense*, *Propionibacterium acidipropionici*, *Streptococcus pneumoniae*, *Streptococcus enterica*, *Streptococcus pyogenes*, *Acholeplasma laidlawii*, *Acinetobacter calcoaceticus*, *Ajellomyces capsulatus*, *Bacillus subtilis*, *Borrelia burgdorferi*, *Chaetomium globosum*, *Clostridium acetobutylicum*, *Clostridium thermocellum*, *Coccidioides immitis*, *Coprinopsis cinerea*, *Cryptococcus neoformans*, *Cupriavidus necator*, *Desulfovibrio vulgaris*, *Enterococcus faecalis*, *Escherichia coli*, *Ethanoligenes harbinense*, *Geobacillus stearothermophilus*, *Helicobacter pylori*, *Lactobacillus delbrueckii*, *Lactobacillus acidophilus*, *Lactobacillus sanfranciscensis*, *Lactococcus lactis*, *Listeria monocytogenes*, *Mesoplasma florum*, *Methanosarcina acetivorans*, *Methanosarcina mazei*, *Moorella thermoacetica*, *Mycoplasma pneumoniae*, *Oceanobacillus iheyensis*, *Propionibacterium freudenreichii*, *Propionibacterium acidipropionici*, *Rhodospeudomonas palustris*, *Salmonella enteric*, *Staphylococcus aureus*, *Thermotoga maritime* or *Veillonella parvula*.

In another preferred embodiment the enzyme is an enzyme from a fungus, preferably from a fungus of the genus *Aspergillus*, *Gibberella*, *Hypocrea*, *Magnaporthe*, *Phaeosphaeria*, *Phanerochaete*, *Phytophthora*, *Sclerotinia*, *Uncinocarpus*, *Ustilago* or *Neurospora* even more preferably from a fungus of the species *Aspergillus* fumigates, *Aspergillus nidulans*, *Gibberella zeae*, *Hypocrea jecorina*, *Magnaporthe grisea*, *Phaeosphaeria nodorum*, *Phanerochaete chrysosporium*, *Phytophthora ramorum*, *Phytophthora sojae*, *Sclerotinia sclerotiorum*, *Uncinocarpus reesii*, *Ustilago maydis* or *Neurospora crassa*.

In a further preferred embodiment the enzyme is an enzyme from a plant or an algae, preferably from the genus *Chlamydomonas*, even more preferably from the species *Chlamydomonas reinhardtii*.

In another embodiment the enzyme is from an organism of the genus *Entamoeba*, more preferably of the species *Entamoeba histolytica*.

The above mentioned enzyme families suitable for the conversion of 3-hydroxy-3-methylbutyryl phosphate into 3-hydroxy-3-methylbutyric acid have been shown to be evolutionary related and contain common sequence signatures. Theses signatures are referenced and described in Prosite database:
http://prosite.expasy.org/cgi-bin/prosite/nicedoc.pl?PS01075

Gao et al. (FEMS Microbiol. Lett. 213 (2002), 59-65) already described genetically modified *E. coli* cells which have been transformed, inter alia, with the ptb gene and the buk gene from *Clostridium acetobutylicum* encoding a phosphate butyryltransferase (EC 2.3.1.19) and a butyrate kinase (EC 2.7.2.7), respectively. These *E. coli* cells have been shown to be able to D-(−)-3-hydroxybutyric acid (3HB).

The 3-methylcrotonyl-CoA which is used to be converted into 3-hydroxy-3-methylbutyric acid via 3-hydroxy-3-methylbutyryl-CoA can be provided itself by the methods as described herein above. Thus, the present invention also relates to a method for producing 3-hydroxy-3-methylbutyric acid comprising the steps of converting 3-methylcrotonyl-CoA via 3-hydroxy-3-methylbutyryl-CoA into 3-hydroxy-3-methylbutyric acid and further comprising any of the above described further enzymatic steps for providing 3-methylcrotonyl-CoA. The produced 3-hydroxy-3-methylbutyric acid can be further converted into isobutene as described above. Thus, the present invention also relates to a method for producing isobutene comprising the above described methods for producing 3-hydroxy-3-methylbutyric acid and further comprising the step of converting the thus produced 3-hydroxy-3-methylbutyric acid enzymatically into isobutene as described above.

A method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In another embodiment the method according to the invention is carried out in culture, in the presence of an organism, preferably a microorganism, producing the enzymes described above for the conversions of the method according to the present invention as described herein above. A method which employs a microorganism for carrying out a method according to the invention is referred to as an "in vivo" method. It is possible to use a microorganism which naturally produces the enzymes described above for the conversions of the method according to the present invention or a microorganism which had been genetically modified so that it expresses (including overexpresses) one or more of such enzymes. Thus, the microorganism can be an engineered microorganism which expresses enzymes described above for the conversions of the method according to the present invention, i.e. which has in its genome a nucleotide sequence encoding such enzymes and which has been modified to overexpress them. The expression may occur constitutively or in an induced or regulated manner.

In another embodiment the microorganism can be a microorganism which has been genetically modified by the introduction of one or more nucleic acid molecules containing nucleotide sequences encoding one or more enzymes described above for the conversions of the methods according to the present invention. The nucleic acid molecule can be stably integrated into the genome of the microorganism or may be present in an extrachromosomal manner, e.g. on a plasmid.

Such a genetically modified microorganism can, e.g., be a microorganism that does not naturally express enzymes described above for the conversions of the method according to the present invention and which has been genetically modified to express such enzymes or a microorganism which naturally expresses such enzymes and which has been genetically modified, e.g. transformed with a nucleic acid, e.g. a vector, encoding the respective enzyme(s), and/or insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme.

Thus, the enzymes and (micro)organisms employed in connection with the present invention are preferably non-naturally occurring enzymes or (microorganisms), i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have the respective enzyme activity but which is genetically modified so as to comprise a nucleotide sequence allowing the expression of a corresponding enzyme. Similarly, the microorganism may also be a microorganism which naturally has the respective enzyme activity but which is genetically modified so as to enhance such an activity, e.g. by the introduction of an exogenous nucleotide sequence encoding a corresponding enzyme or by the introduction of a promoter for the endogenous gene encoding the enzyme to increase endogenous production to overexpressed (non-natural) levels.

If a microorganism is used which naturally expresses a corresponding enzyme, it is possible to modify such a microorganism so that the respective activity is overexpressed in the microorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express enzymes described above for the conversions of the methods according to the present invention, it is possible to carry out the methods according to the invention directly in the culture medium, without the need to separate or purify the enzymes.

In one embodiment the organism employed in a method according to the invention is a microorganism which has been genetically modified to contain a foreign nucleic acid molecule encoding at least one enzyme described above for the conversions of the methods according to the present invention. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the method according to the invention makes use of a photosynthetic microorganism expressing at least one enzyme for the conversion according to the invention as described above. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above. The genetic modification of microorganisms to express an enzyme of interest will also be further described in detail below.

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harboring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

The enzymes used in the method according to the invention can be a naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a corresponding enzyme. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" means that the expression and/or the activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA.

Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

The present invention furthermore relates to the use of
   a thioesterase (EC 3.1.2) or an organism expressing a thioesterase (EC 3.1.2); or
   a CoA-transferase (EC 2.8.3) or an organism expressing a CoA-transferase (EC 2.8.3)
for the enzymatic conversion of 3-methylcrotonyl-CoA into 3-methylcrotonic acid.

As regards the thioesterase and the CoA-transferase and the microorganism, the same applies as has been set forth above in connection with a method according to the invention.

The present invention also relates to the use of a combination comprising
   a phosphate butyryltransferase (EC 2.3.1.19) and/or a phosphate acetyltransferase (EC 2.3.1.8); and
   a phosphotransferase (EC 2.7.2), preferably a butyrate kinase (EC 2.7.2.7), a branched-chain-fatty-acid kinase (EC 2.7.2.14), a propionate kinase (EC 2.7.2.15) and/or an acetate kinase (EC 2.7.2.1)
for the conversion of 3-methylcrotonyl-CoA into 3-methylcrotonic acid.

Moreover, the present invention relates to the use of a combination comprising
   a thioesterase (EC 3.1.2) and/or a CoA-transferase (EC 2.8.3); and
   a hydro-lyases (EC 4.2.1);
or comprising
   a phosphate butyryltransferase (EC 2.3.1.19) and/or a phosphate acetyltransferase (EC 2.3.1.8); and
   a phosphotransferase (EC 2.7.2), preferably a butyrate kinase (EC 2.7.2.7), a branched-chain-fatty-acid kinase (EC 2.7.2.14), a propionate kinase (EC 2.7.2.15) and/or an acetate kinase (EC 2.7.2.1); and
   a hydro-lyases (EC 4.2.1);
for the conversion of 3-methylcrotonyl-CoA into 3-hydroxy-3-methylbutyric acid.

As regards the thioesterase and the CoA-transferase as well as the hydratase/dehydratase and the microorganism, the same applies as has been set forth above in connection with a method according to the invention.

The present invention also relates to the use of a combination comprising
- an organism expressing a thioesterase (EC 3.1.2) and/or a CoA-transferase (EC 2.8.3); and
- an organism expressing a hydro-lyases (EC 4.2.1), or comprising
- an organisms expressing a phosphate butyryltransferase (EC 2.3.1.19) and/or a phosphate acetyltransferase (EC 2.3.1.8); and
- a phosphotransferase (EC 2.7.2), preferably a butyrate kinase (EC 2.7.2.7), a branched-chain-fatty-acid kinase (EC 2.7.2.14), a propionate kinase (EC 2.7.2.15) and/or an acetate kinase (EC 2.7.2.1); and
- an organism expressing a hydro-lyases (EC 4.2.1), for the conversion of 3-methylcrotonyl-CoA into 3-hydroxy-3-methylbutyric acid.

Furthermore, the present invention relates to the use of an organism expressing
- a thioesterase (EC 3.1.2) and/or a CoA-transferase (EC 2.8.3); and
- a hydro-lyases (EC 4.2.1), or of an organism expressing
- a phosphate butyryltransferase (EC 2.3.1.19) and/or a phosphate acetyltransferase (EC 2.3.1.8); and
- a phosphotransferase (EC 2.7.2), preferably a butyrate kinase (EC 2.7.2.7), a branched-chain-fatty-acid kinase (EC 2.7.2.14), a propionate kinase (EC 2.7.2.15) and/or an acetate kinase (EC 2.7.2.1); and
- a hydro-lyases (EC 4.2.1);

for the conversion of 3-methylcrotonyl-CoA into 3-hydroxy-3-methylbutyric acid.

As regards the afore-mentioned embodiments, for the thioesterase and the CoA-transferase as well as the hydratase/dehydratase and the microorganism, the same applies as has been set forth above in connection with a method according to the invention.

The present invention also relates to the use of a combination comprising
(a) an enzyme selected from the group consisting of
  (i) a 3-hydroxypropionyl-CoA dehydratase (EC 4.2.1.116);
  (ii) a 3-hydroxybutyryl-CoA dehydratase (EC 4.2.1.55);
  (iii) an enoyl-CoA hydratase (EC 4.2.1.17);
  (iv) a 3-hydroxyoctanoyl-[acyl-carrier-protein] dehydratase (EC 4.2.1.59);
  (v) a crotonyl-[acyl-carrier-protein] hydratase (EC 4.2.1.58);
  (vi) a 3-hydroxydecanoyl-[acyl-carrier-protein] dehydratase (EC 4.2.1.60);
  (vii) a 3-hydroxypalmitoyl-[acyl-carrier-protein] dehydratase (EC 4.2.1.61);
  (viii) a long-chain-enoyl-CoA hydratase (EC 4.2.1.74); and
  (ix) a 3-methylglutaconyl-CoA hydratase (EC 4.2.1.18)
and
(b) a phosphate butyryltransferase (EC 2.3.1.19) and/or a phosphate acetyltransferase (EC 2.3.1.8);
and
(c) a phosphotransferase (EC 2.7.2)
for the enzymatic conversion of 3-methylcrotonyl-CoA into 3-hydroxy-3-methylbutyric acid.

The present invention also relates to the use of a combination comprising
- an organism expressing an enzyme as defined in (a), above; and
- an organism expressing an enzyme as defined in (b), above; and
- an organism expressing an enzyme as defined in (c), above, for the conversion of 3-methylcrotonyl-CoA into 3-hydroxy-3-methylbutyric acid.

Furthermore, the present invention relates to an organism expressing:
- an enzyme as defined in (a), above; and
- an enzyme as defined in (b), above, and
- an enzyme as defined in (c), above;

as well as to the use of such an organism for the conversion of 3-methylcrotonyl-CoA into 3-hydroxy-3-methylbutyric acid.

As regards the afore-mentioned embodiments, for the enzymes mentioned therein and the microorganism, the same applies as has been set forth above in connection with a method according to the invention.

Moreover, described is a method for producing 3-hydroxy-3-methylbutyric acid comprising the step of enzymatically converting 3-methylcrotonyl-CoA into 3-methylcrotonic acid and the step of enzymatically further converting the thus produced 3-methylcrotonic acid into 3-hydroxy-3-methylbutyric acid. The conversion of 3-methylcrotonyl-CoA into 3-methylcrotonic acid can be achieved by a direct conversion which preferably makes use of an enzyme which belongs to the family of thioester hydrolases (also referred to as thioesterases (EC 3.1.2)) or to the family of CoA-transferases (EC 2.8.3). In the alternative, the conversion of 3-methylcrotonyl-CoA into 3-methylcrotonic acid can be achieved by a conversion which first encompasses the conversion of 3-methylcrotonyl-CoA into 3-methylcrotonyl-phosphate and the subsequent conversion of 3-methylcrotonyl-phosphate into 3-methylcrotonic acid. The conversion of 3-methylcrotonic acid into 3-hydroxy-3-methylbutyric acid preferably makes use of an enzyme which belongs to the family of hydro-lyases (EC 4.2.1), in particular of an aconitate hydratase (EC 4.2.1.3) or of a maleate hydratase (EC 4.2.1.31) or of a 2-methylcitrate dehydratase (EC 4.2.1.79). Thus, the present invention in particular relates to the following items:

1. A method for the conversion of 3-methylcrotonyl-CoA into 3-hydroxy-3-methylbutyric acid comprising the steps of:
   (a) enzymatically converting 3-methylcrotonyl-CoA into 3-methylcrotonic acid; and
   (b) further enzymatically converting the thus produced 3-methylcrotonic acid into 3-hydroxy-3-methylbutyric acid.

2. The method of item 1, wherein the enzymatic conversion of 3-methylcrotonyl-CoA into 3-methylcrotonic acid according to step (a) is achieved by the use of
   (i) a thioester hydrolase (EC 3.1.2); or
   (ii) a CoA-transferase (EC 2.8.3).

3. The method of item 2, wherein the thioesterase (EC 3.1.2) is selected from the group consisting of
   acetyl-CoA hydrolase (EC 3.1.2.1);
   palmitoyl-CoA hydrolase (EC 3.1.2.2);
   3-hydroxyisobutyryl-CoA hydrolase (EC 3.1.2.4);
   oleoyl-[acyl-carrier-protein] hydrolase (EC 3.1.2.14);
   ADP-dependent short-chain-acyl-CoA hydrolase (EC 3.1.2.18);
   ADP-dependent medium-chain-acyl-CoA hydrolase (EC 3.1.2.19); and
   acyl-CoA hydrolase (EC 3.1.2.20).

4. The method of items 2 or 3, wherein the CoA-transferase (EC 2.8.3) is selected from the group consisting of
   acetate CoA-transferase (EC 2.8.3.8); and
   butyrate-acetoacetate CoA-transferase (EC 2.8.3.9).

5. The method of item 1, wherein the enzymatic conversion of 3-methylcrotonyl-CoA into 3-methylcrotonic acid according to step (a) is achieved by first converting 3-methylcrotonyl-CoA into 3-methylcrotonyl-phosphate and then subsequently converting the thus produced 3-methylcrotonyl-phosphate into 3-methylcrotonic acid.

6. The method of item 5, wherein the conversion of 3-methylcrotonyl-CoA into 3-methylcrotonyl-phosphate is achieved by making use of a phosphate butyryltransferase (EC 2.3.1.19) or a phosphate acetyltransferase (EC 2.3.1.8).

7. The method of item 5 or 6, wherein the conversion of 3-methylcrotonyl-phosphate into 3-methylcrotonic acid is achieved by making use of a phosphotransferase (EC 2.7.2).

8. The method of item 7, wherein the phosphotransferase (EC 2.7.2) is selected from the group consisting of a butyrate kinase (EC 2.7.2.7), a branched-chain-fatty-acid kinase (EC 2.7.2.14), a propionate kinase (EC 2.7.2.15) and an acetate kinase (EC 2.7.2.1).

9. The method of any one of items 1 to 8, wherein the enzymatic conversion of 3-methylcrotonic acid into 3-hydroxy-3-methylbutyric acid according to step (b) is achieved by the use of a hydro-lyase (EC 4.2.1).

10. The method of item 9, wherein the hydratase/dehydratase (EC 4.2.1) is selected from the group consisting of
aconitate hydratase (EC 4.2.1.3);
maleate hydratase (EC 4.2.1.31); and
2-methylcitrate dehydratase (EC 4.2.1.79).

11. Use of
a thioester hydrolase (EC 3.1.2) or an organism expressing a thioester hydrolase (EC 3.1.2); or
a CoA-transferase (EC 2.8.3) or an organism expressing a CoA-transferase (EC 2.8.3)
for the enzymatic conversion of 3-methylcrotonyl-CoA into 3-methylcrotonic acid
or of a combination comprising
a phosphate butyryltransferase (EC 2.3.1.19) and/or a phosphate acetyltransferase (EC 2.3.1.8); and
a phosphotransferase (EC 2.7.2)
for the enzymatic conversion of 3-methylcrotonyl-CoA into 3-methylcrotonic acid.

12. Use of a combination comprising
a thioester hydrolase (EC 3.1.2) and/or a CoA-transferase (EC 2.8.3); and
a hydratase/dehydratase (EC 4.2.1)
or comprising
a phosphate butyryltransferase (EC 2.3.1.19) and/or a phosphate acetyltransferase (EC 2.3.1.8); and
a phosphotransferase (EC 2.7.2); and
a hydro-lyase (EC 4.2.1);
for the conversion of 3-methylcrotonyl-CoA into 3-hydroxy-3-methylbutyric acid.

13. Use of a combination comprising
an organism expressing a thioester hydrolase (EC 3.1.2) and/or a CoA-transferase (EC 2.8.3); and
an organism expressing a hydro-lyase (EC 4.2.1),
or comprising
an organisms expressing a phosphate butyryltransferase (EC 2.3.1.19) and/or a phosphate acetyltransferase (EC 2.3.1.8); and
a phosphotransferase (EC 2.7.2); and
an organism expressing a hydro-lyase (EC 4.2.1),
for the conversion of 3-methylcrotonyl-CoA into 3-hydroxy-3-methylbutyric acid.

14. Use of an organism expressing
a thioester hydrolase (EC 3.1.2) and/or a CoA-transferase (EC 2.8.3); and
a hydro-lyase (EC 4.2.1),
or of an organism expressing
a phosphate butyryltransferase (EC 2.3.1.19) and/or a phosphate acetyltransferase (EC 2.3.1.8); and
a phosphotransferase (EC 2.7.2); and
a hydro-lyase;
for the conversion of 3-methylcrotonyl-CoA into 3-hydroxy-3-methylbutyric acid.

15. The use of any one of items 11 to 14, wherein the thioester hydrolase (EC 3.1.2) is selected from the group consisting of
acetyl-CoA hydrolase (EC 3.1.2.1);
palmitoyl-CoA hydrolase (EC 3.1.2.2);
3-hydroxyisobutyryl-CoA hydrolase (EC 3.1.2.4);
oleoyl-[acyl-carrier-protein] hydrolase (EC 3.1.2.14);
ADP-dependent short-chain-acyl-CoA hydrolase (EC 3.1.2.18);
ADP-dependent medium-chain-acyl-CoA hydrolase (EC 3.1.2.19); and
acyl-CoA hydrolase (EC 3.1.2.20).

16. The use of any one of items 11 to 15, wherein the CoA-transferase (EC 2.8.3) is selected from the group consisting of
acetate CoA-transferase (EC 2.8.3.8); and
butyrate-acetoacetate CoA-transferase (EC 2.8.3.9).

17. The use of any one of items 11 to 16, wherein the phosphotransferase (EC 2.7.2) is selected from the group consisting of a butyrate kinase (EC 2.7.2.7), a branched-chain-fatty-acid kinase (EC 2.7.2.14), a propionate kinase (EC 2.7.2.15) and an acetate kinase (EC 2.7.2.1).

FIG. 12 shows the activity of several studied enzymes for 3-methylcrotonyl-CoA hydration monitored by recording the decrease of absorbance of 3-methylcrotonyl-CoA at 263 nm (Example 2).

Figure 14:
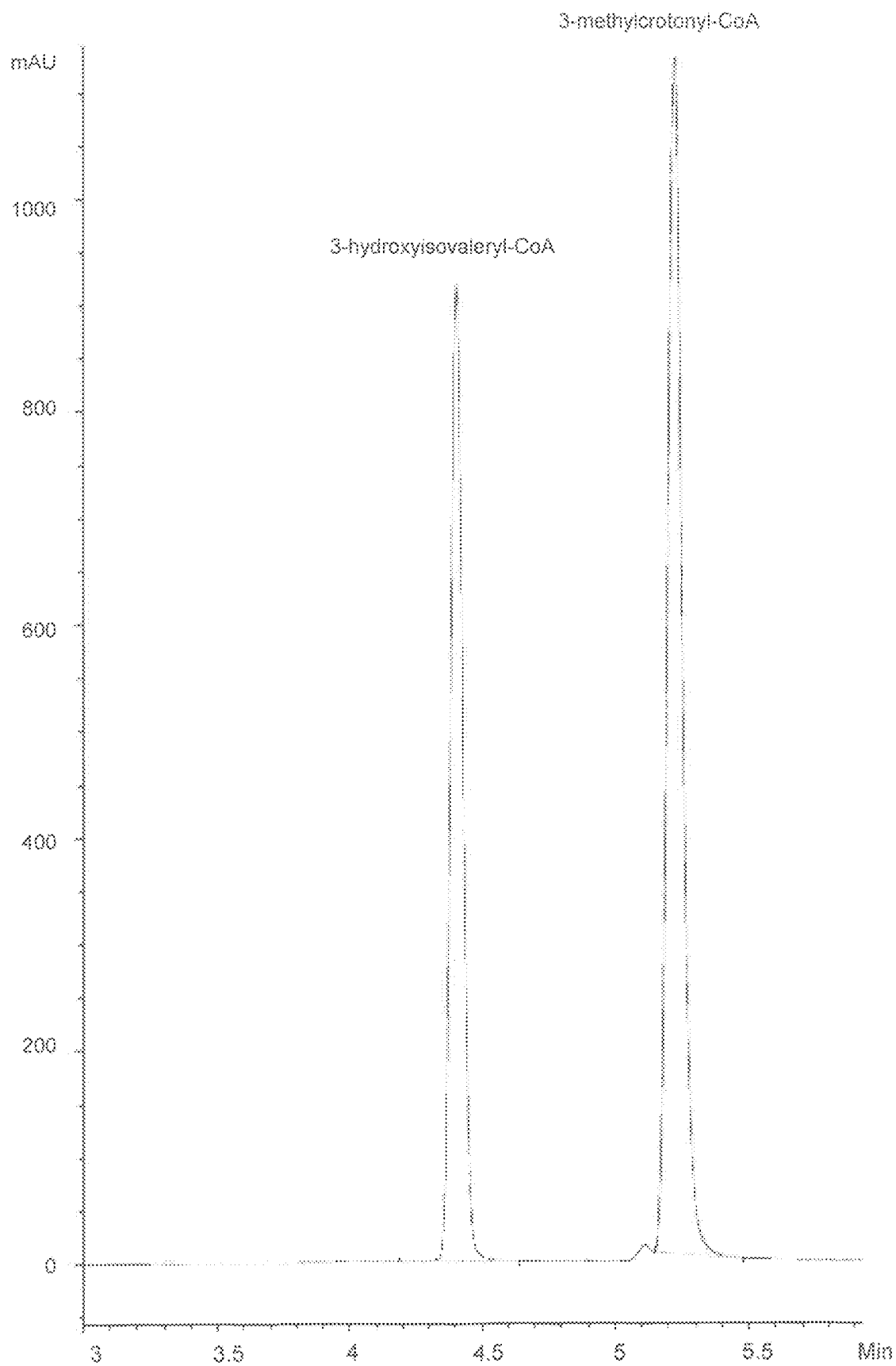

FIG. 14 shows a chromatogram obtained for the enzymatic hydration of 3-methylcrotonyl-CoA with 3-hydroxypropionyl-CoA dehydratase from *Metallosphaera sedula* as outlined in Example 4. The assay was performed with 4 mM 3-methylcrotonyl-CoA and incubated for 16 min.

Figure 15:
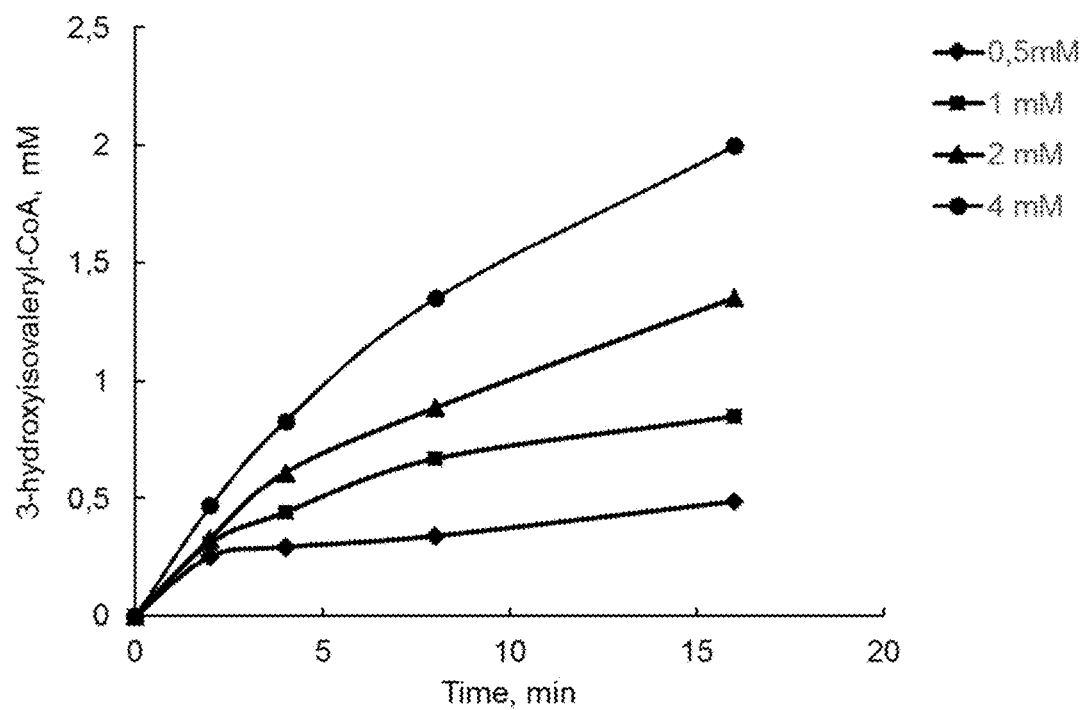

FIG. 15 shows the formation of 3-hydroxyisovaleryl-CoA from 3-methylcrotonyl-CoA as function of time at different substrate concentrations. The conversion was catalyzed by the 3-hydroxypropionyl-CoA dehydratase from *Metallosphaera sedula* (Example 4).

FIG. 16 shows in part A the percentage of the conversion of 3-hydroxy-3-methylglutaryl-CoA into 3-methylglutaconyl-CoA by different enzymes shown in part B (Example 5).

Figure 17:
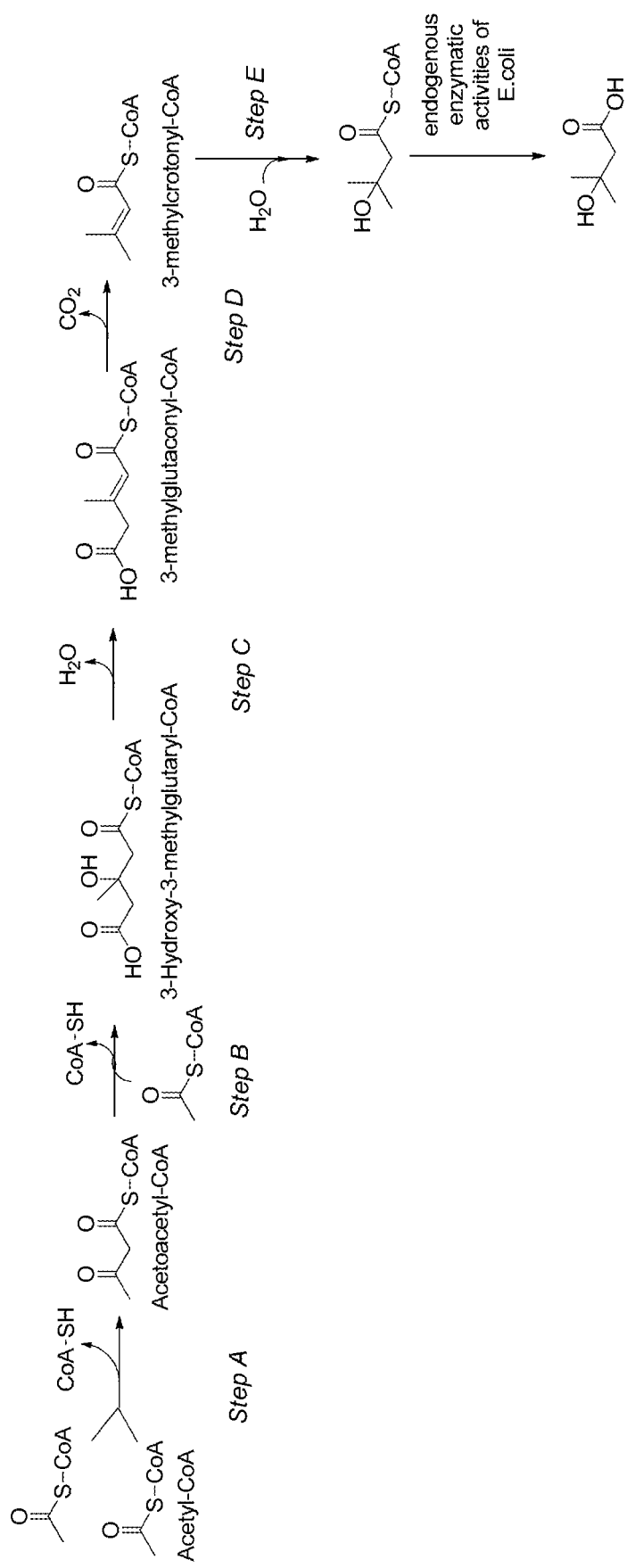

FIG. 17 shows a schematic of exemplary biochemical pathways leading to isobutene from acetyl-CoA as outlined in Example 6.

Figure 18:
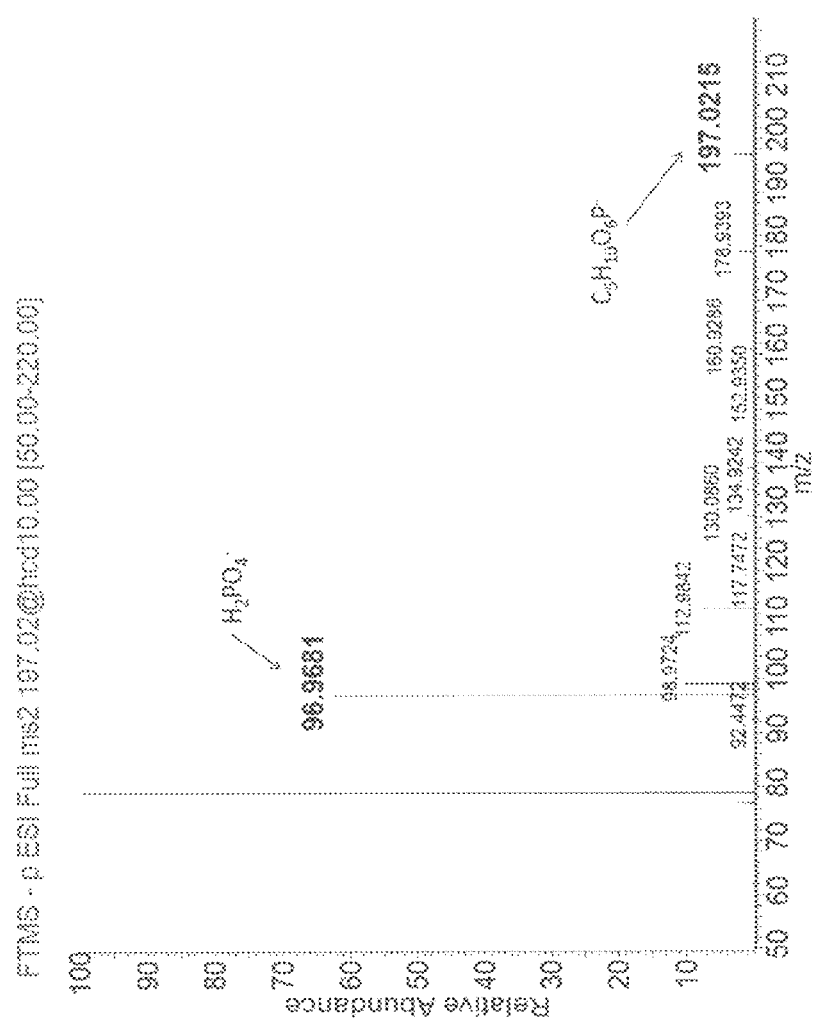

FIG. 18 shows a mass spectrum of 3-hydroxyisovaleryl phosphate (3-hydroxy-3-methylbutyryl phosphate) produced from 3-hydroxyisovaleryl-CoA (3-hydroxy-3-methylbutyryl-CoA) and phosphate catalyzed by phosphate butyryltransferase from *Bacilllus subtilis* (Example 9).

Figure 19:
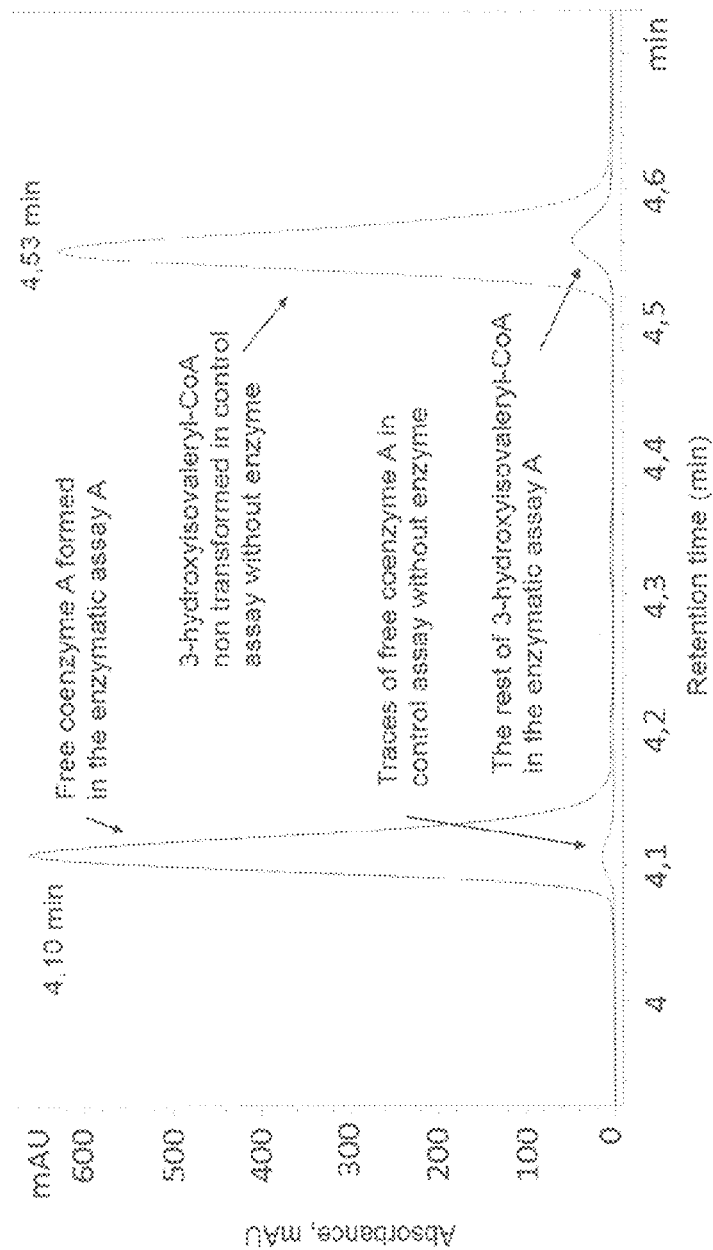

FIG. 19 shows an overlay of typical HPLC-chromatograms obtained for
a) the enzymatic Assay A in Example 10; and
b) the enzyme-free Assay H in Example 10.
In the HPLC-chromatograms 3-hydroxyisovaleryl-CoA (3-hydroxy-3-methylbutyryl-CoA) and Co—SH were analyzed.

The consumption of 3-hydroxyisovaleryl-CoA (3-hydroxy-3-methylbutyryl-CoA) with simultaneous production of CoA-SH was observed in the enzymatic assay combining phosphate butyryltransferase with butyrate kinase.

Figure 20:
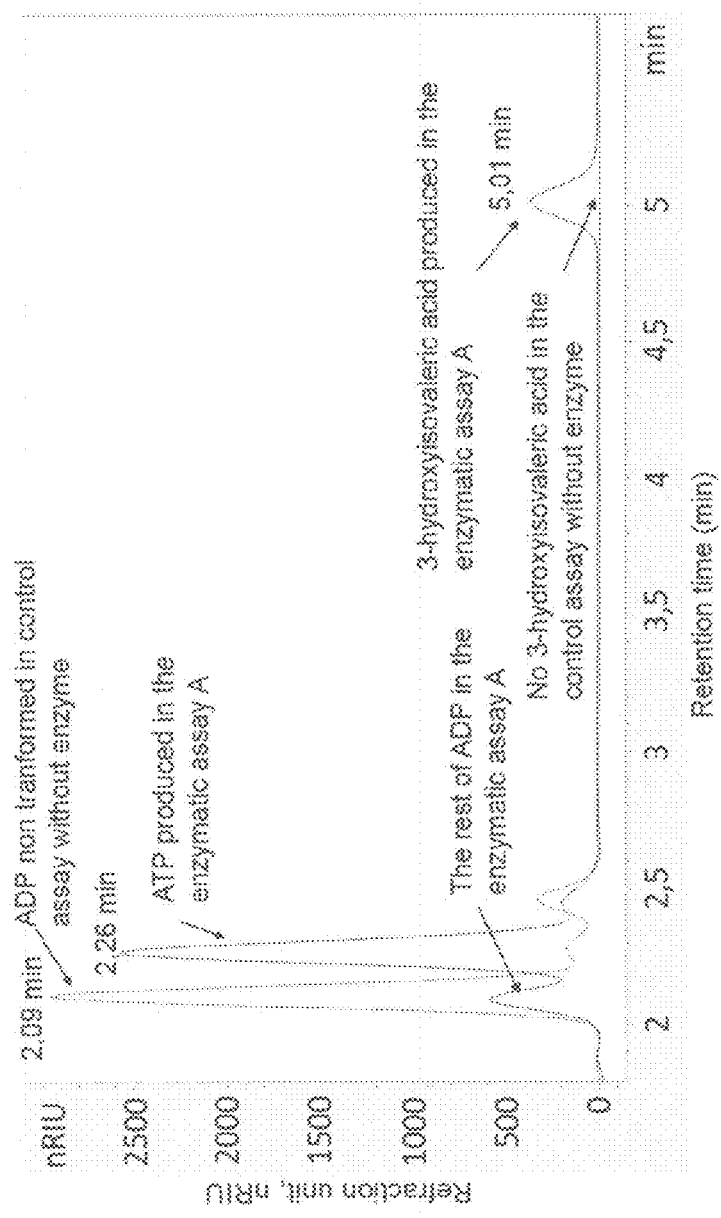

FIG. 20 shows an overlay of typical HPLC-chromatograms obtained for
a) enzymatic assay (Assay A, Example 10)
b) enzyme-free assay (Assay H, Example 10).
In the HPLC-chromatograms 3-hydroxyisovaleric acid, ADP and ATP were analyzed.

The consumption of ADP with simultaneous production of ATP was observed in the enzymatic assay combining phosphate butyryltransferase with butyrate kinase.

Figure 21:
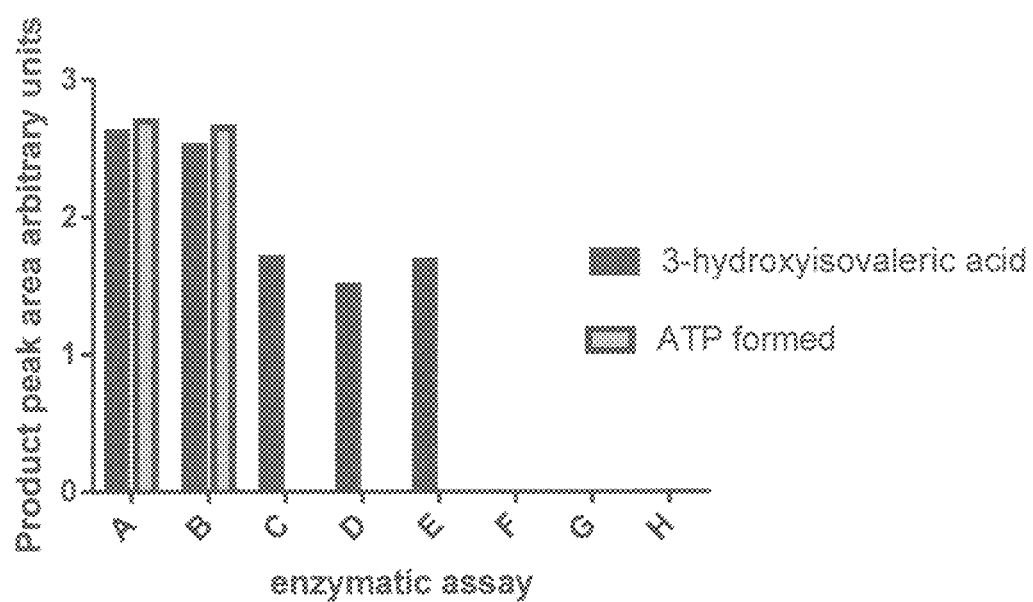

FIG. 21 shows the results of the production of 3-hydroxyisovaleric acid (3-hydroxy-3-methylbutyric acid) and ATP in the enzymatic assays wherein phosphate butyryltransferase from *Bacilllus subtilis* is combined with different butyrate kinases. Further, the results of different control assays as indicated in Example 10 are shown.

Figure 22:
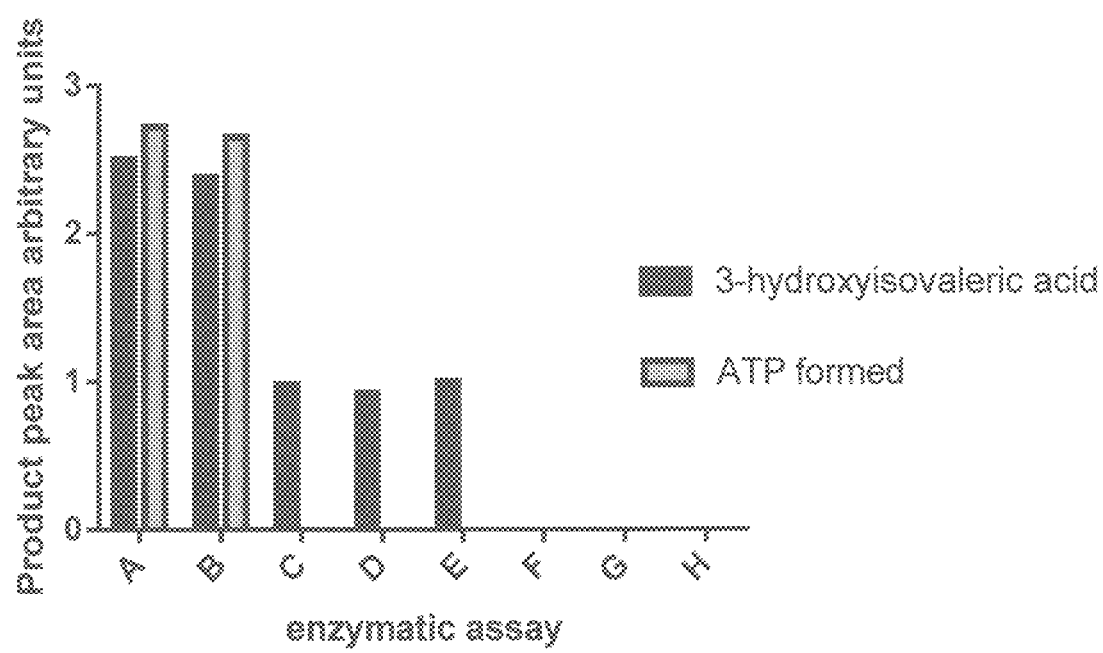

FIG. 22 shows the results of the production of 3-hydroxyisovaleric acid (3-hydroxy-3-methylbutyric acid) and ATP in the enzymatic assays wherein phosphate butyryltransferase from *Enterococcus faecalis* is combined with different butyrate kinases. Further, the results of different control assays as indicated in Example 11 are shown.

Figure 23:
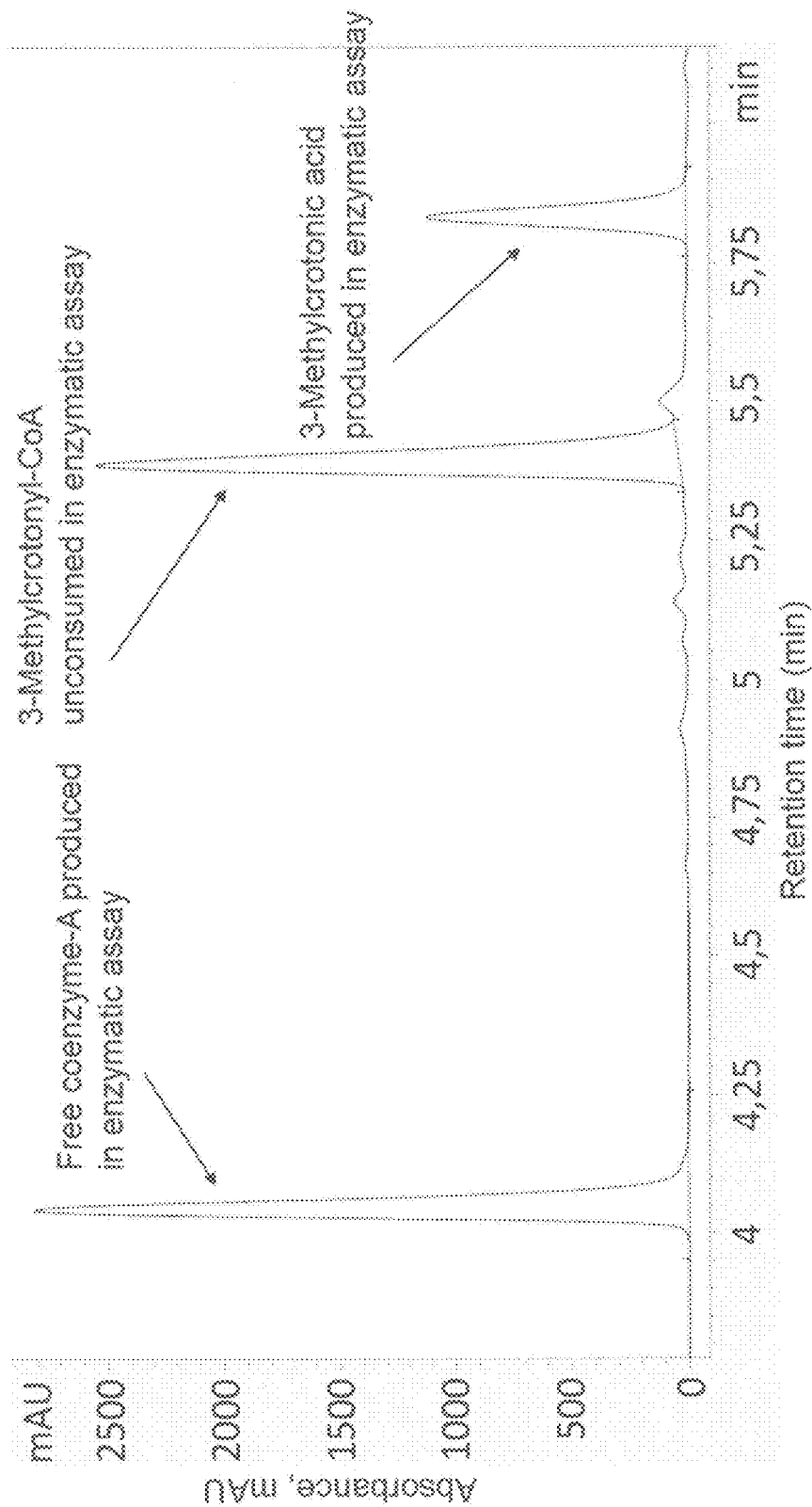

FIG. 23 shows an example of a typical HPLC-chromatogram obtained for the enzymatic assay with acyl-CoA thioesterase II from *Pseudomonas putida*.

Figure 24A:
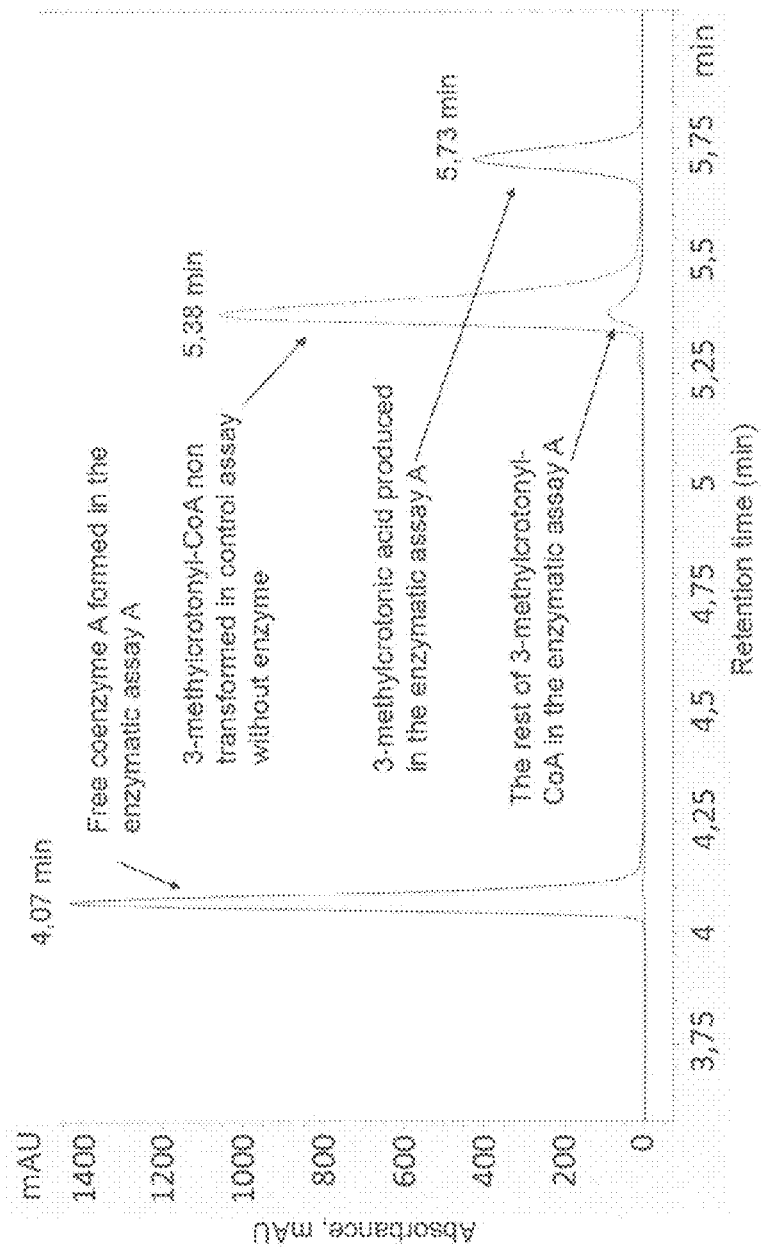

FIG. 24a shows an overlay of typical HPLC-chromatograms (analysis of 3-methylcrotonyl-CoA, 3-methylcrotonic acid and CoA-SH) obtained for
a) enzymatic assay (assay A, Example 13)
b) enzyme-free assay (assay H, Example 13).
The consumption of 3-methylcrotonyl-CoA with simultaneous production of CoA-SH and 3-methylcrotonic acid was observed in the enzymatic assay combining phosphate butyryltransferase with butyrate kinase.

Figure 24B:
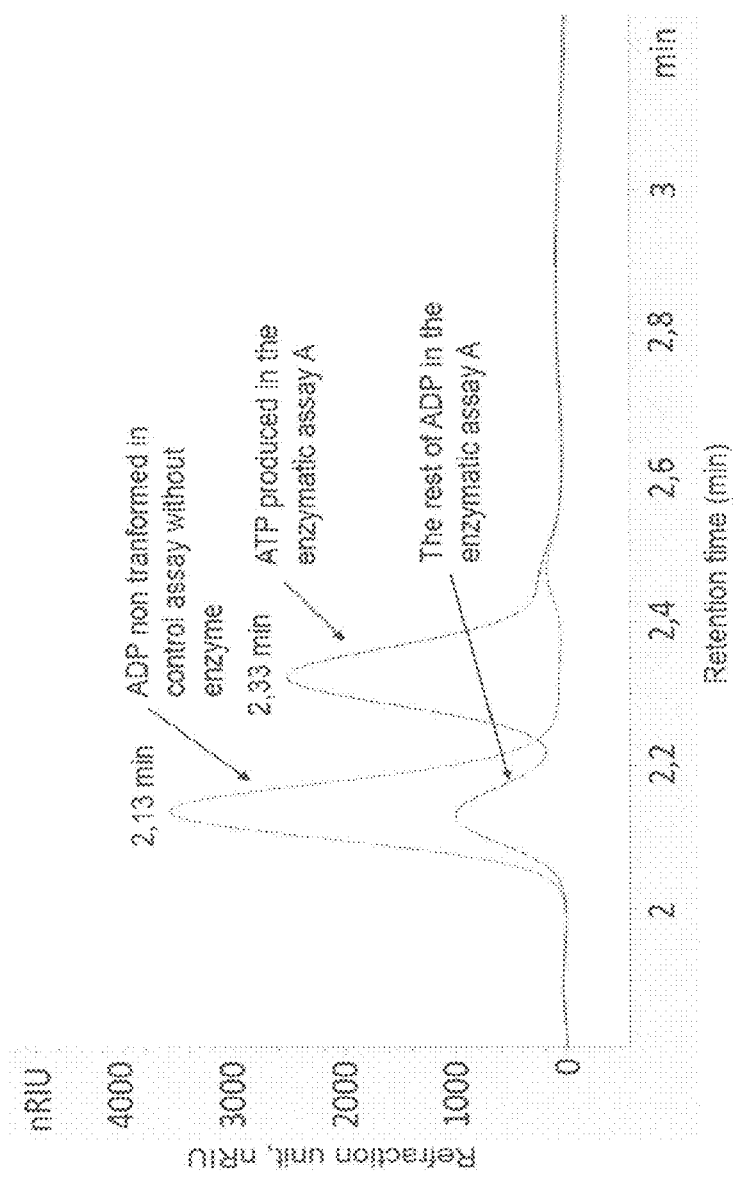

FIG. 24b shows an overlay of typical HPLC-chromatograms obtained for (analysis of ADP and ATP) obtained for
a) enzymatic assay (assay A, Example 13)
b) enzyme-free assay (assay H, Example 13).
The consumption of ADP with simultaneous production of ATP was observed in the enzymatic assay combining phosphate butyryltransferase with butyrate kinase.

Figure 25:
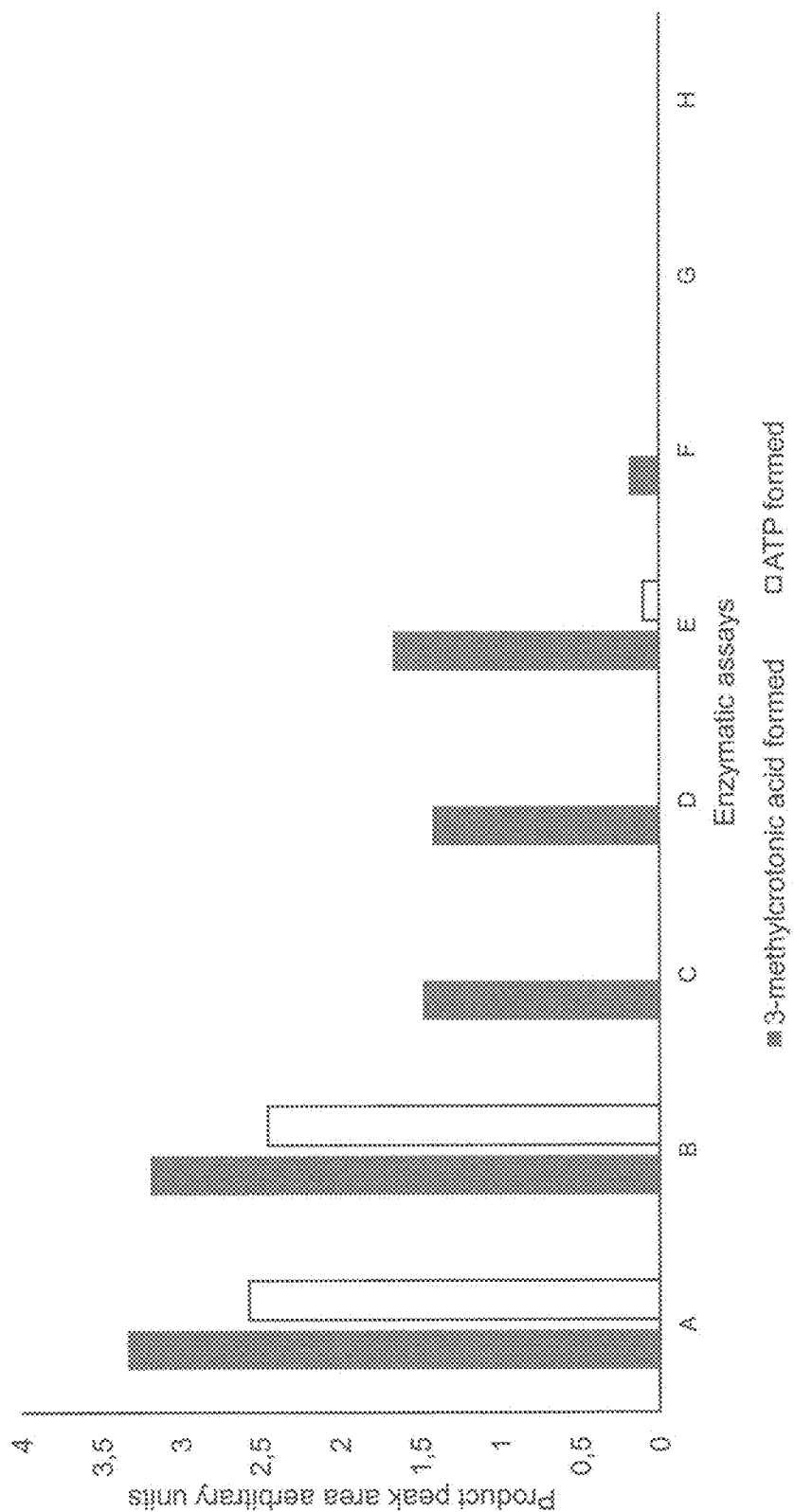

FIG. 25 shows the results of the production of 3-methylcrotonic acid and ATP in enzymatic assays comprising phosphate butyryltransferase from *Bacilllus subtilis* combined with different butyrate kinases, as well as in different control assays.

Figure 26:
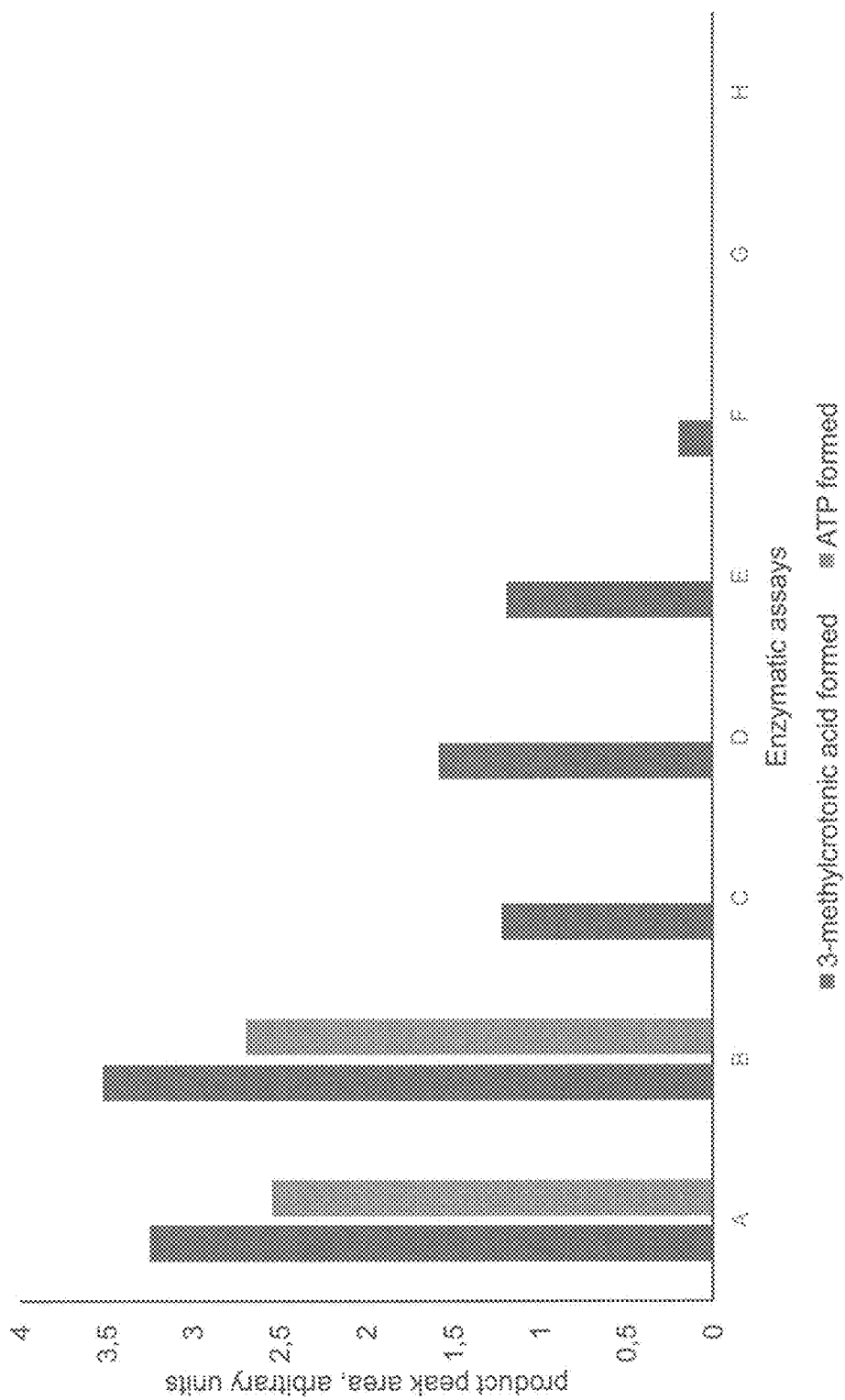

FIG. 26 shows the results of the production of 3-methylcrotonic acid and ATP in enzymatic assays comprising phosphate butyryltransferase from *Enterococcus faecalis* combined with different butyrate kinases, as well as in different control assays.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1: Cloning, Expression and Purification of Enzymes

Gene Synthesis, Cloning and Expression of Recombinant Proteins

The sequences of the studied enzymes inferred from the genomes of prokaryotic and eukaryotic organisms were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The genes thus synthesized were cloned in a pET-25b(+) expression vector (vectors were constructed by GeneArt®).

Competent *E. coli* BL21(DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 6 h at 30° C. and protein expression was continued at 28° C. or 18° C. overnight (approximately 16 h). The cells were collected by centrifugation at 4° C., 10,000 rpm for 20 min and the pellets were stored at −80° C.

Protein Purification and Concentration

The pellets from 200 ml of culture cells were thawed on ice and resuspended in 5 ml of 50 mM HEPES buffer pH 7.0 containing 500 mM NaCl, 10 mM MgCl$_2$, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×30 seconds. The bacterial extracts were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 50 mM HEPES buffer pH 7.0 containing 300 mM NaCl and 250 mM imidazole. Eluates were then concentrated, desalted on Amicon Ultra-4 10 kDa filter unit (Millipore) and enzymes were resuspended in 50 mM HEPES pH 7.0, containing 100 mM NaCl. The purity of proteins thus purified varied from 70% to 90% as estimated by SDS-PAGE analysis. Protein concentrations were determined by direct UV 280 nm measurement on the NanoDrop 1000 spectrophotometer (Thermo Scientific) or by Bradford assay (BioRad).

Example 2: Screening of a Collection of Hydro-Lyases Using 3-Methylcrotonyl-CoA as Substrate for the Production of 3-Hydroxy-3-Methylbutyryl-CoA (3-Hydroxyisovaleryl-CoA)

The genes coding for acyl-CoA dehydratases and enoyl-CoA hydratases were synthesized and the corresponding enzymes were further produced according to the procedure described in Example 1. The stock solution of 3-methylcrotonyl-CoA (Sigma-Aldrich) was prepared in water. Standard reaction mixture contained:
50 mM HEPES pH 7.0
0.25 mM 3-methylcrotonyl-CoA
5 mM $MgCl_2$
5 mM NaCl
0.002 mg/ml of purified enzyme Assays were performed in 96-well plates at 30° C. in a total volume of 0.12 ml.

Each reaction was started by the addition of 3-methylcrotonyl-CoA. The samples were then continuously monitored for the decrease of the absorbance of 3-methylcrotonyl-CoA at 263 nm (Fukui T et al. J. Bacteriol. 180 (1998), 667-673) on a SpectraMax Plus 384 UV/Vis Microplate Reader (Molecular Devices).

Several enzymes showed activity with 3-methylcrotonyl-CoA as a substrate (FIG. 12). No modification of the absorbance at 263 nm was observed for the control assay without enzyme.

Example 3: HPLC-Based Analysis of Products of the Enzymatic Hydration of 3-Methylcrotonyl-CoA The enzymatic assays were conducted in total reaction volume of 0.2 ml
The standard reaction mixture contained:
50 mM HEPES pH 7.0
4 mM 3-methylcrotonyl-CoA
20 mM $MgCl_2$
20 mM NaCl
0.02 mg/ml of purified 3-hydroxypropionyl-CoA dehydratase from *Metallosphaera sedula* (Uniprot Accession number: A4YI89) or purified enoyl-CoA hydratase *Bacillus anthracis* (Uniprot Accession number: Q81YG6)

Assays were incubated for 0, 5 and 30 min with shaking at 30° C.

After an incubation period, the reactions were stopped by the addition of 0.1 ml of acetonitrile. The amount of 3-hydroxy-3-methylbutyryl-CoA (3-hydroxyisovaleryl-CoA) was quantified using a HPLC-based procedure.

The samples were centrifuged, filtered through a 0.22 µm filter and the clarified supernatants were transferred into a clean vial for further analysis.

HPLC analysis was performed using 1260 Infinity LC System (Agilent), equipped with column heating module and UV detector (260 nm). 5 µl of samples were separated on Zorbax SB-Aq column (250×4.6 mm, 5 µm particle size, column temp. 30° C.), with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). 3-hydroxyisovaleryl-CoA was chemically synthesized from 3-hydroxyisovaleric acid, upon request, by a company specialized in custom synthesis (Syntheval, France).

The retention time of 3-hydroxyisovaleryl-CoA and 3-methylcrotonyl-CoA under these conditions was 4.40 and 5.25 min, respectively.

Figure 1:
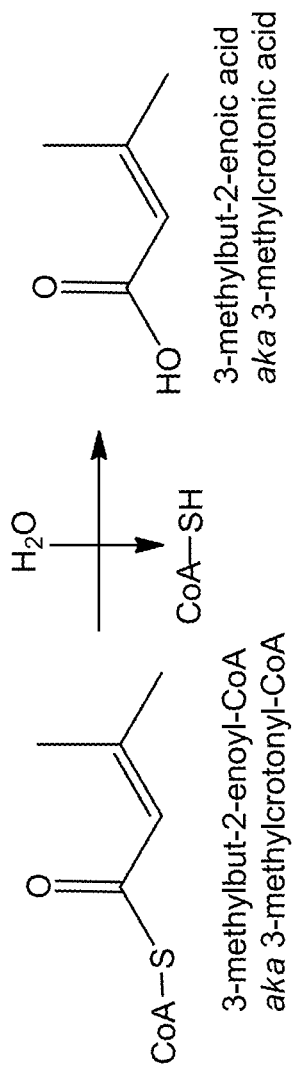
FIG. 1 shows schematically the reaction of the conversion of 3-methylcrotonyl-CoA into 3-methylcrotonic acid catalyzed by a thioesterase.
Figure 2:
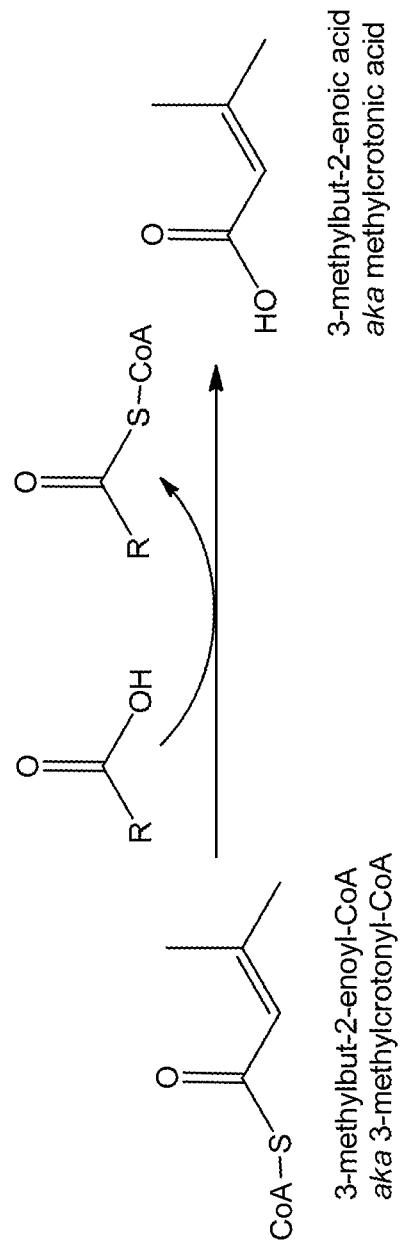
FIG. 2 shows schematically the reaction of the conversion of 3-methylcrotonyl-CoA into 3-methylcrotonic acid catalyzed by a CoA-transferase.
Figure 3:
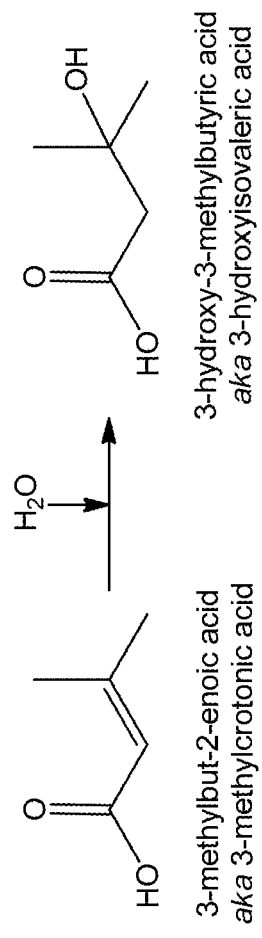
FIG. 3 shows schematically the reaction of the conversion of 3-methylcrotonic acid into 3-hydroxy-3-methylbutyric acid.
Figure 4:
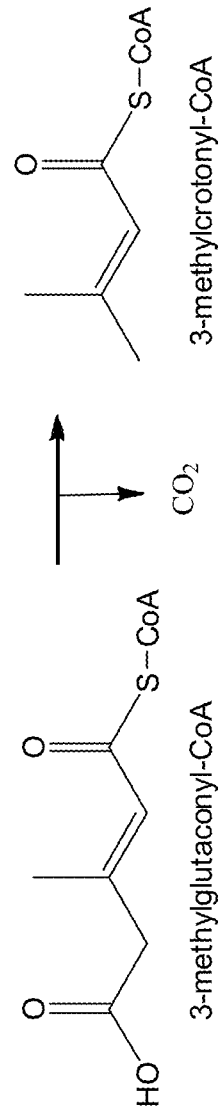
FIG. 4 shows the conversion of 3-methylglutaconyl-CoA into 3-methylcrotonyl-CoA via a decarboxylation reaction.
Figure 5:
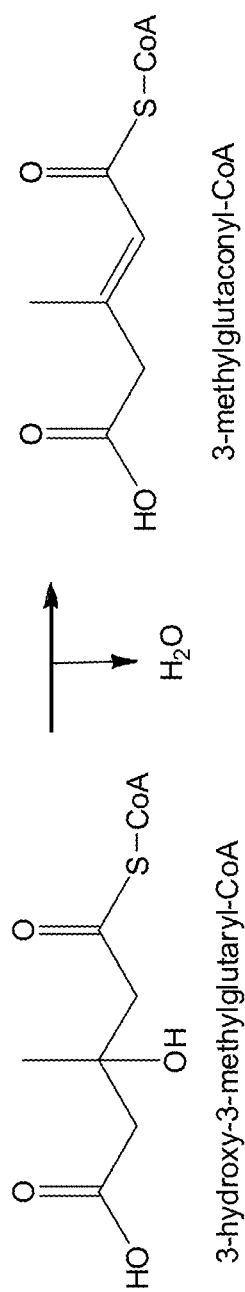
FIG. 5 shows conversion of 3-hydroxy-3-methylglutaryl-CoA into 3-methylglutaconyl-CoA.
Figure 6:
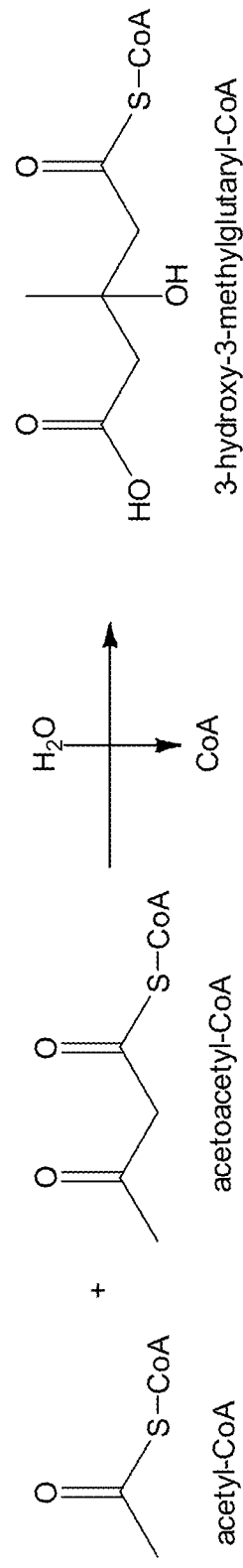
FIG. 6 shows the condensation of acetyl-CoA and acetoacetyl-CoA into 3-hydroxy-3-methylglutaryl-CoA.
Figure 7:
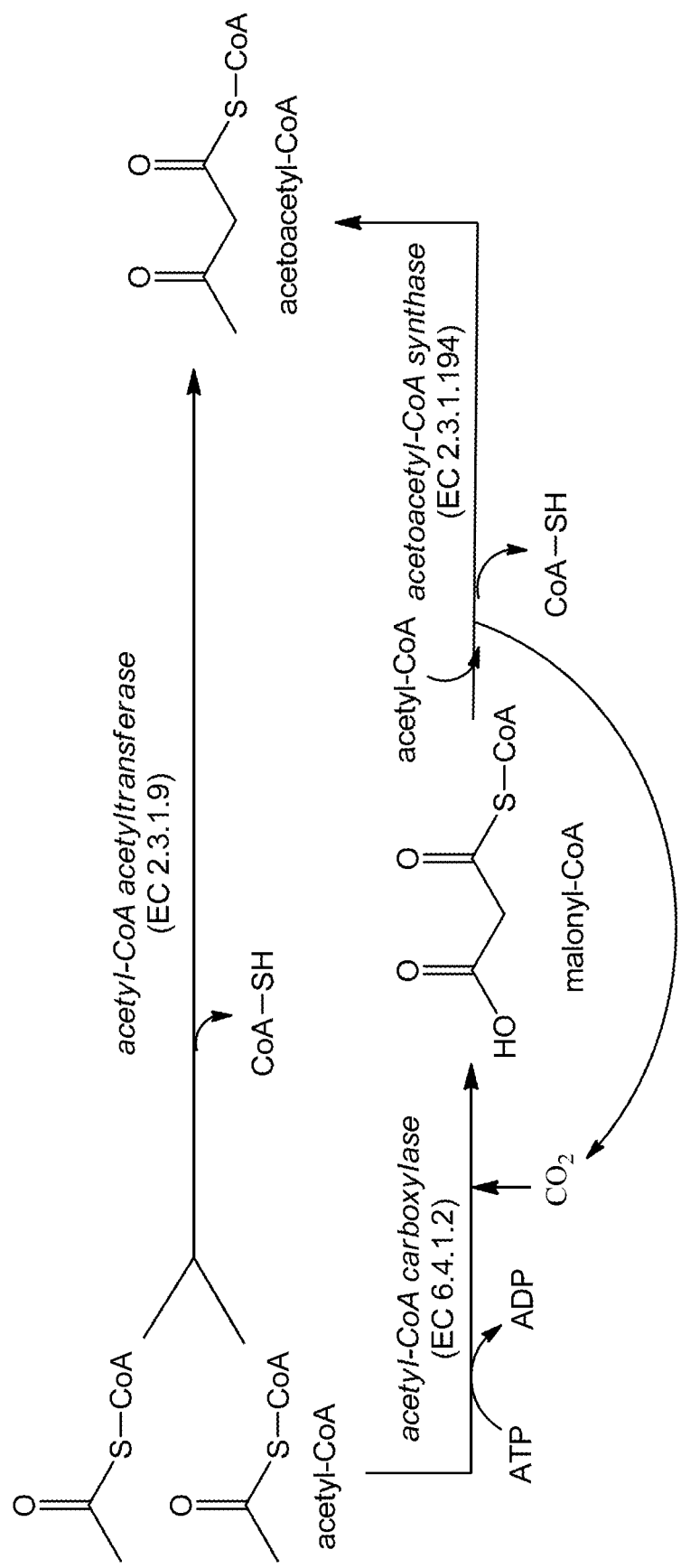
FIG. 7 shows possible pathways for producing acetoacetyl-CoA from acetyl-CoA.
Figure 8:
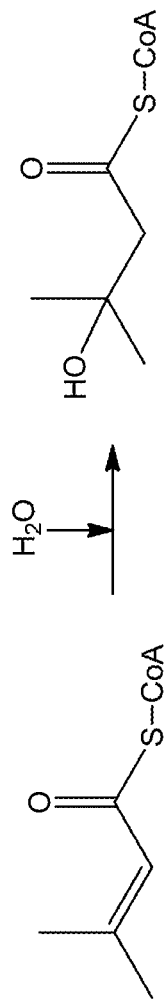
FIG. 8 shows the conversion of 3-methylcrotonyl-CoA into 3-hydroxy-3-methylbutyryl-CoA.
Figure 9:
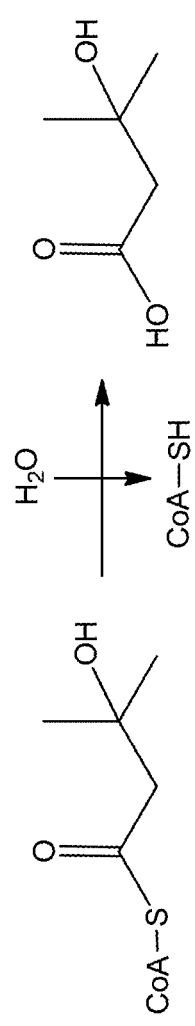
FIG. 9 shows the conversion of 3-hydroxy-3-methylbutyryl-CoA into 3-hydroxy-3-methylbutyric acid catalyzed by a thioesterase.
Figure 10:
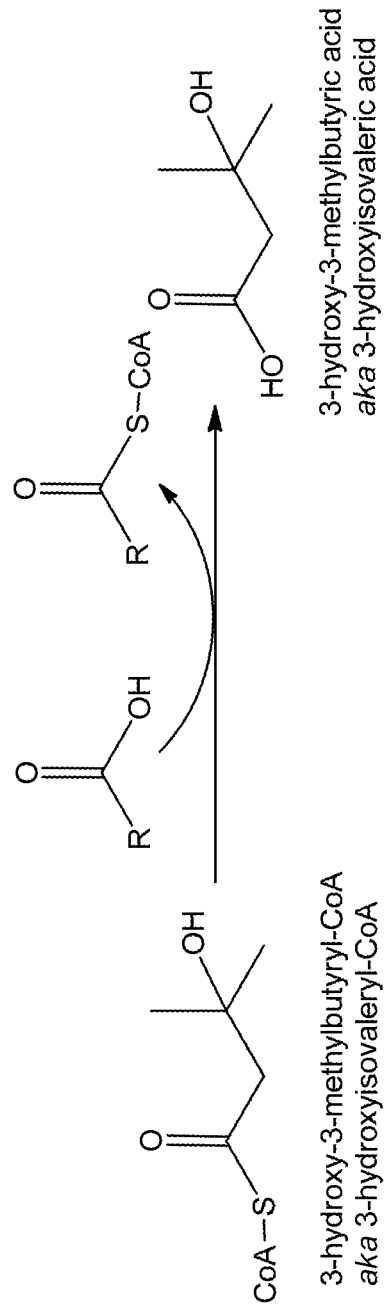
FIG. 10 shows the conversion of 3-hydroxy-3-methylbutyryl-CoA into 3-hydroxy-3-methylbutyric acid catalyzed by a CoA-transferase.
Figure 11:
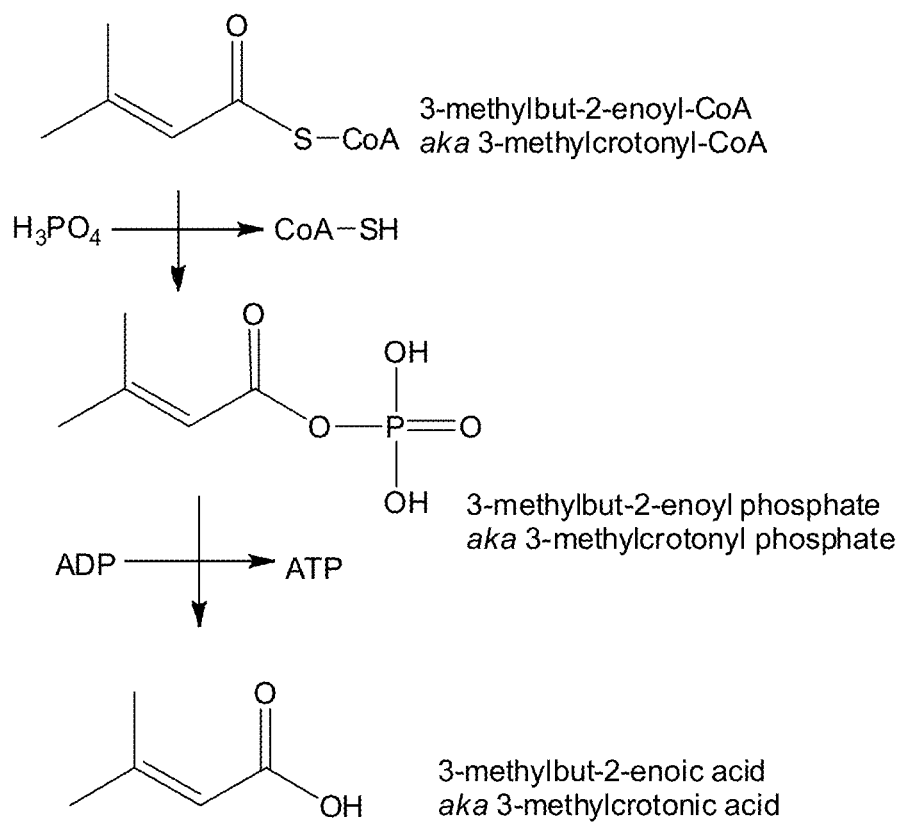
FIG. 11 shows the conversion of 3-methylcrotonyl-CoA into 3-methylcrotonyl-phosphate and the subsequent conversion of 3-methylcrotonyl-phosphate into 3-methylcrotonic acid.
Figure 13:
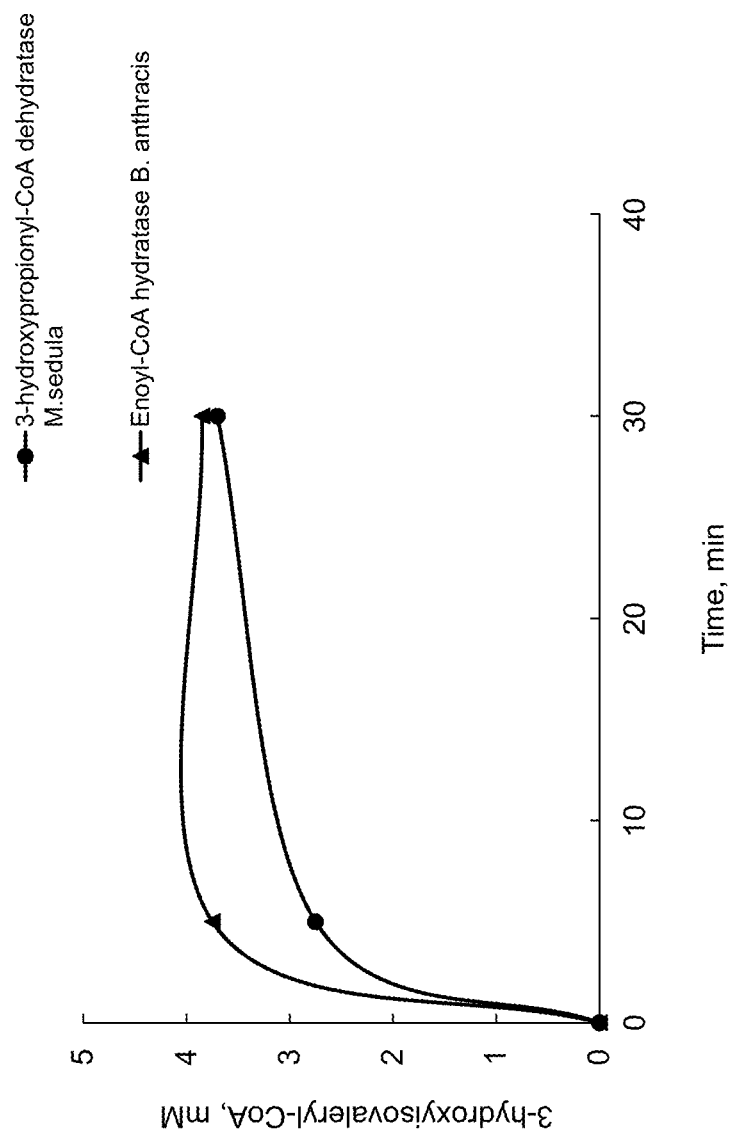
FIG. 13 shows the time course of the formation of 3-hydroxy-3-methylbutyryl-CoA acid (3-hydroxyisovaleryl-CoA) by hydration of 3-methylcrotonyl-CoA catalyzed by the 3-hydroxypropionyl-CoA dehydratase from *Metallosphaera sedula* and enoyl-CoA hydratase from *Bacillus anthracis* (Example 3).

Significant production of 3-hydroxyisovaleryl-CoA was observed in enzymatic assays (FIG. 13). No 3-hydroxyisovaleryl-CoA production was observed in enzyme-free control assay.

Thus, acyl-CoA dehydratase and enoyl-CoA hydratase were able to efficiently catalyze the hydration of 3-methylcrotonyl-CoA into 3-hydroxyisovaleryl-CoA.

Example 4: Kinetic Studies of the Hydration Reaction of 3-Methylcrotonyl-CoA The enzymatic assays were conducted in total reaction volume of 0.2 ml
The standard reaction mixture contained:
50 mM HEPES pH 7.0
0-4 mM 3-methylcrotonyl-CoA
20 mM $MgCl_2$
20 mM NaCl
0.01 mg/ml 3-hydroxypropionyl-CoA dehydratase from *Metallosphaera sedula*.

Assays were incubated for 0, 2, 4, 8, 16 min with shaking at 30° C. and the reactions were stopped by the addition of 100 µl of acetonitrile. The amount of 3-hydroxyisovaleryl-CoA was quantified according to HPLC-based procedure described in Example 3.

FIG. 14 shows an example of typical chromatogram obtained for enzymatic assay with substrate concentration of 4 mM after 16 min of incubation.

The graph depicting 3-hydroxyisovaleryl-CoA formation as a function of time at different substrate concentrations is shown in the FIG. 15. 3-Hydroxypropionyl-CoA dehydratase from *Metallosphaera sedula* was found to have a $K_M$ of 0.3 mM and a $k_{cat}$ of 10 $s^{-1}$ for 3-methylcrotonyl-CoA.

Example 5: Enzyme-Catalyzed Dehydration of 3-Hydroxy-3-Methylglutaryl-CoA into 3-Methylglutaconyl-CoA The genes coding for acyl-CoA dehydratases and enoyl-CoA hydratases were synthesized and the corresponding enzymes were further produced according to the procedure described in Example 1. Stock solution of 3-hydroxy-3-methylglutaryl-CoA (Sigma-Aldrich) was prepared in water.
The enzymatic assays were conducted in total reaction volume of 0.2 ml.
The standard reaction mixture contained:
50 mM HEPES pH 7.0
4 mM 3-hydroxy-3-methylglutaryl-CoA
20 mM $MgCl_2$
20 mM NaCl
0.01 mg/ml of purified enzyme After an incubation period of 16 min the assays were stopped by the addition of 0.1 ml of acetonitrile.

The samples were centrifuged, filtered through a 0.22 μm filter and the clarified supernatants were transferred into a clean vial for HPLC analysis. HPLC analysis was performed according to the procedure described in Example 3. The retention time of 3-hydroxy-3-methylglutaryl-CoA in these conditions was 4.20 min The progress of the reaction was followed by measuring consumption of substrate.

Several acyl-CoA dehydratases and enoyl-CoA hydratases were shown to be able to catalyze the dehydration of 3-hydroxy-3-methylglutaryl-CoA into 3-methylglutaconyl-CoA (FIG. 16).

Example 6: Microorganism for the Production of 3-Hydroxyisovaleric Acid from Acetyl-CoA This working example shows the production of 3-hydroxyisovaleric acid by recombinant E. coli, expressing several exogenous genes.

Like most organisms, E. coli converts glucose to acetyl-CoA. The enzymes used in this study to convert acetyl-CoA into 3-hydroxy-3-methylbutyric acid (aka 3-hydroxyisovaleric acid) following pathway 1 (FIG. 17) are summarized in Table 1.

TABLE 1

| Step | Enzyme | Gene abbreviation | Uniprot Accession number |
|---|---|---|---|
| A | Acetyl-CoA acetyltransferase from *Clostridium acetobutylicum* | CA_C2873 | P45359 |
| B | Hydroxymethylglutaryl-CoA synthase from *Schizosaccharomyces pombe* | Hcs1 | P54874 |
| C | Hydroxybutyryl-CoA dehydratase from *Myxococcus xanthus* (LiuC) | MXAN_3757 | Q1D5Y4 |
| D | Glutaconate CoA-transferase (subunits AibA & AibB) from *Myxococcus xanthus* | MXAN_4264 MXAN_4265 | Q1D4I4 Q1D4I3 |
| E | Hydroxybutyryl-CoA dehydratase from *Myxococcus xanthus* (LiuC) | MXAN_3757 | Q1D5Y4 |

Expression of 3-Hydroxyisovaleric Acid Biosynthetic Pathway in E. coli

The modified version of pUC18 (New England Biolabs), containing a modified Multiple Cloning Site (pUC18 MCS) (WO 2013/007786), was used as an expression vector. A terminator sequence was inserted into pUC18 MCS between the HindIII and NarI restriction sites and the resulting vector was termed pGBE1992.

The corresponding genes were codon optimized for expression in E. coli and synthesized by GeneArt® (Life Technologies)

The acetyl-coA acetyltransferase (CA_C2873) gene was PCR amplified from the pMK-RQ-thl_adc vector (master plasmid provided by GeneArt) using primers 3211 and 3212. A PacI restriction site at the 5' end of the PCR product was introduced. At the 3' end of the PCR product a NotI restriction site and a ClaI restriction site were introduced. The resulting 1.6 kbp PCR product and pGBE1992 were digested with the PacI and NotI restriction enzymes and then ligated together resulting in the pGBE2101 plasmid. The recombinant pGBE2101 plasmid was verified by sequencing.

The 3-hydroxybutyryl-CoA dehydratase (MXAN_3757) gene was PCR amplified from the pMK-T-ACoADH_MX vector (master plasmid provided by GeneArt) using primers 3327 and 3328. An EcoRI restriction site at the 5' end and a KpnI restriction site at the 3' end were inserted by PCR. The amplified gene comprised a full-length MXAN_3757 coding sequence with a stretch of 6 histidine codons after methionine initiation codon to provide an affinity tag for purification. The resulting 0.8 kbp PCR product was digested with the restriction enzymes and ligated into the pGBE2101 plasmid previously digested with the EcoRI and KpnI restriction endonucleases. The resulting plasmid was termed pGBE2326 and verified by sequencing.

The plasmid pMK-RQ-AibA_AibB (master plasmid provided by GeneArt) was digested with the restriction enzymes ClaI and NotI to create a 1.6 Kbp product. The 1.6 kbp restriction fragment, contained MXAN_4264 and MXAN_4265 genes, was ligated into cut pGBE2326 plasmid. The resulting recombinant plasmid pGBE2360 was verified by sequencing.

The Hcs1 gene coding for hydroxymethylglutaryl-CoA synthase from S. pombe was PCR amplified from the pET-25b(+)-A_129 (master plasmid provided by GeneArt) with primers 3329 and 3330. A NotI restriction site at the 5' end and a HindIII restriction site at the 3' end were thereby introduced by PCR. The amplified gene comprised a full-length Hcs1 coding sequence with a stretch of 6 histidine codons after methionine initiation codon to provide an affinity tag for purification. The resulting 1.4 kbp PCR product was digested with the NotI and HindIII restriction enzymes and ligated with the digested pGBE2360 plasmid. The resulting plasmid pGBE2396 was verified by sequencing.

TABLE 2

| Primer names | Primers sequences |
|---|---|
| 3211 | CCCGCGGCCGCCCTATCGATTTATTAGC (SEQ ID NO: 22) |
| 3212 | TTAATTAATGAAAGAAGTGGTGATTGC (SEQ ID NO: 23) |
| 3327 | GGGGAATTCAGGAGGTGTACTAGATGCATCATCATCATCAC CACATGCC (SEQ ID NO: 24) |
| 3328 | CCCGGTACCTTATTAGCGACCTTTATAAACCGG (SEQ ID NO: 25) |
| 3329 | GGGGCGGCCGCAGGAGGTGTACTAGATGCACCATCATCATC ATCACAGC (SEQ ID NO: 26) |
| 3330 | CCCAAGCTTTTATTACGGTTTAACGCTATAGC (SEQ ID NO: 27) |

Culture Medium and Flask Fermentation Conditions

Strain MG1655 E. coli was made electrocompetent. MG1655 electrocompetent cells were then transformed with the expression vector pGBE2396. An empty plasmid pUC18 was transformed as well to create a strain used as a negative control in the assay.

The transformed cells were then plated on LB plates, supplied with ampicillin (100 μg/ml). Plates were incubated overnight at 30° C. Isolated colonies were used to inoculate LB medium, supplemented with ampicillin, followed by incubation at 30° C. overnight. 1 ml of this overnight culture was used to inoculate 300 ml of ZYM-5052 auto-inducing media (Studier F W, Prot. Exp. Pur. 41, (2005), 207-234). This culture was grown for 20 h at 30° C. and 160 rpm shaking.

A volume of cultures corresponding to $OD_{600}$ of 30 was removed and centrifuged. The pellet was resuspended in 30 ml of MS medium (Richaud C., Mengin-Leucreulx D., Pochet S., Johnson E J., Cohen G N. and Marliére P, The Journal of Biological Chemistry, 268, (1993), 26827-26835) containing glucose (45 g/L), and MgSO4 (1 mM).

The cultures were then incubated in 160 ml bottles, sealed with a screw cap, at 30° C. with shaking for 3 days. The pH value of the cultures was adjusted to 8.5 twice per day using 30% $NH_4OH$.

At the end of incubation 1 ml of culture mediums was removed and centrifuged at 4° C., 10,000 rpm for 5 min. The supernatants were filtered through a 0.22 μm filter and diluted with an equal volume of $H_2O$. The production of 3-hydroxyisovaleric acid was then analyzed.

Analysis of 3-Hydroxyisovaleric Acid Production

The amount of 3-hydroxyisovaleric acid produced was measured using a HPLC-based procedure. HPLC analysis was performed using a 1260 Infinity LC System Agilent, equipped with column heating module, and refractometer. 10 μl of samples were separated using 3 columns connected in series as follows:

1. Hi-Plex guard column (100×7.7 mm, 8 μm particle size) (Agilent)
2. Hi-Plex column (100×7.7 mm, 8 μm particle size) (Agilent)
3. Zorbax SB-Aq column (250×4.6 mm, 5 μm particle size, column temp. 65° C.) (Agilent).

The mobile phase consisted of aqueous sulfuric acid (1 mM), mobile phase flow rate was 1.5 ml/min. Commercial 3-hydroxyisovaleric acid (TCI) was used as reference. Retention time of 3-hydroxyisovaleric acid under these conditions was 7.7 min. About 2.2 mM 3-hydroxyisovaleric acid was produced in these shake-flask experiments by engineered E. coli, contained the genes of 3-hydroxyisovaleric acid biosynthetic pathway. No 3-hydroxyisovaleric acid production was observed with the control strain, contained empty vector.

Bioreactor Fermentation Conditions

Strain E. coli MG1655 Δagp ΔaphA was made electrocompetent. The electrocompetent cells were then transformed with the expression vector pGBE2396.

The transformed cells were then plated on LB plates and the preculture was prepared according to the procedure described in the section "Culture medium and flask fermentation conditions".

The fermentation was performed in a 1 L bioreactor with pH and temperature control (Multifors 2, Infors HT). Cells of a preculture in LB medium were used to inoculate a 900 ml of MS liquid medium containing MgSO4 (1 mM), yeast extract (2 g/L) and ampicilline (100 μg/ml) at an initial optical density ($OD_{600}$) of 0.5 Concentration of glucose over the fermentation run was maintained between 0 g/L and 10 g/L using feed pumps. Temperature and pH were maintained constant (30° C. and 6.5, respectively). Dissolved oxygen was maintained to 20% (100% is obtained in air). Aliquots of culture medium were taken over the fermentation period and centrifuged at 4° C., 10 000 rpm for 5 min. The supernatant were then filtered through a 0.22 μm filter and diluted with an equal volume of $H_2O$. The amount of produced 3-hydroxyisovaleric acid was measured according to the HPLC-based procedure described above.

After 143 hours of fermentation the 3-hydroxyisovaleric acid concentration reached 12 mM.

Example 7: Enzyme-Catalyzed Hydrolysis of 3-Hydroxyisovaleryl-CoA into 3-Hydroxyisovaleric Acid The gene coding for acyl-CoA thioesterase II from Pseudomonas putida was synthesized and the corresponding enzymes were further produced according to the procedure described in Example 1.

Vectors pCAN contained genes coding for acyl-CoA thioester hydrolase YciA and acyl-CoA thioesterase 2 (TesB) from Escherichia coli were purchased from NAIST (Nara Institute of Science and Technology, Japan, ASKA collection). Provided vectors contained a stretch of 6 histidine codons after the methionine initiation codon. The corresponding enzymes were further produced according to the procedure described in Example 1.

The enzymatic assays were conducted in total reaction volume of 0.2 ml

The standard reaction mixture contained:
50 mM HEPES pH 7.0
10 mM 3-hydroxyisovaleryl-CoA
20 mM $MgCl_2$
20 mM NaCl
1 mg/ml of purified thioesterase The assays were incubated for 30 min with shaking at 30° C. and the reactions were stopped by the addition of 0.1 ml of acetonitrile. The amount of 3-hydroxyisovaleryl-CoA was quantified according to HPLC-based procedure described in Example 3.

In these conditions, the 3-hydroxyisovaleryl-CoA retention time was 4.40 min and coenzyme A (CoA) retention time was 3.96 min. A significant decrease of 3-hydroxyisovaleryl-CoA peak was observed in conjunction with increased coenzyme A peak.

Additionally, 3-hydroxyisovaleric acid production was analyzed according to the procedure described en Example 6.

All the studied thioesterases catalyzed the hydrolysis of 3-hydroxyisovaleryl-CoA with the formation of 3-hydroxyisovaleric acid (Table 3).

No 3-hydroxyisovalerate signal was observed in control assay without enzyme.

TABLE 3

| Gene names | Organism | Uniprot Accession number | Conversion, % |
|---|---|---|---|
| yciA | Escherichia coli | P0A8Z0 | 25 |
| tesB | Escherichia coli | P0AGG2 | 52 |
| tesB | Pseudomonas putida | Q88DR1 | 58 |

Example 8: Cloning and Overexpression of Recombinant Phosphate Butyryltransferases and Butyrate Kinases Gene Synthesis, Cloning and Expression of Recombinant Proteins The sequences of phosphate butyryltransferase genes from Bacillus subtilis (strain 168) and Enterococcus faecalis MTUP9 (Uniprot Accession number: P54530 and A0A038BNC2, respectively) and butyrate kinase from Lactobacillus casei W56 and Geobacillus sp. GHH01 (Uniprot Accession number: K0N529 and L8A0E1, respectively) were generated by oligonucleotide concatenation to fit the codon usage of E. coli (genes were commercially synthesized by GeneArt®). The expression of corresponding proteins was conducted following the method described in Example 1.

The cells were collected by centrifugation at 4° C., 10.000 rpm for 20 min and the pellets were stored at −80° C.

Protein Purification and Concentration

The pellets from 200 ml of cultured cells were thawed on ice and resuspended in 5 ml of 50 mM potassium phosphate buffer pH 7.5 containing 100 mM NaCl, 10 mM $MgCl_2$, 10 mM imidazole and 1 mM DTT. Twenty microliters of lysonase (Novagen) were added. Cells were incubated 10 minutes at room temperature and then returned to ice for 20 minutes. Cell lysis was completed by sonication for 2×30 seconds. The bacterial extracts were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 50 mM potassium phosphate buffer pH 7.5 containing 100 mM NaCl and 250 mM imidazole. Eluates were then concentrated, desalted on an Amicon Ultra-4 10 kDa filter unit (Millipore) and enzymes were resuspended in 50 mM potassium phosphate buffer pH 7.5, containing 100 mM NaCl. The purity of proteins thus purified varied from 70% to 90% as estimated by SDS-PAGE analysis. Protein concentrations were determined by direct UV 280 nm measurement on the NanoDrop 1000 spectrophotometer (Thermo Scientific) or by Bradford assay (BioRad).

Example 9: Formation of 3-Hydroxyisovaleryl Phosphate from 3-Hydroxyisovaleryl-CoA and Phosphate Catalyzed by Phosphate Butyryltransferase from *Bacillus subtilis*

The studied enzymatic reaction was carried out under the following conditions:
50 mM Tris-HCl pH 7.5
10 mM $MgCl_2$
10 mM NaCl
10 mM 3-hydroxyisovaleryl-CoA (3-hydroxy-3-methylbutyryl-CoA)

The purified phosphate butyryltransferase from *B. subtilis* was resuspended in 5 mM potassium phosphate pH 7.5.

A control assay without enzyme was performed in parallel.

The enzymatic assay was initiated by the addition of 20 μl of enzyme preparation into 20 μl of reaction mixture. The formation of 3-hydroxyisovaleryl phosphate (3-hydroxy-3-methylbutyryl phosphate) was analyzed by Mass Spectrometry (MS). 5 μl of the assay was introduced into the mass spectrometer via a loop injection.

Flow injection analyses were performed using a Dionex Ultimate chromatographic system (Thermo Fisher Scientific) at a flow rate of 100 μL/min with a mobile phase composed of $H_2O$ containing 10 mM ammonium formate pH 9.45 and acetonitrile 75:25 v/v. Detection was performed with a Q-exactive spectrometer (Thermo Fisher Scientific) fitted with an electrospray ionization source (negative ionization mode at a resolution of 70000 m/Δm, FWHM at m/z 200). Non-resonant induced dissociation experiments—Higher-energy C-trap dissociation (HCD)—were acquired at normalized collision energy of 10%. Raw data were manually inspected using the Qualbrowser module of Xcalibur version 3.0 (Thermo Fisher Scientific).

The formation of new ion with m/z at 197.0213, corresponding to $C_5H_{10}O_6P^-$, was observed in the enzymatic assay (FIG. 18).

Structural elucidation and complete assignment of this newly formed ion (m/z at 197.0213) were further investigated using MS/MS analysis. The fragment ion with m/z value of 96.968, corresponding to the $H_2PO_4^-$ species, was generated under MS/MS experiment. Thus, the generation of 3-hydroxyisovaleryl phosphate in the enzyme catalyzed assay was proved by MS technique.

Example 10: Conversion of 3-Hydroxyisovaleryl-CoA and ADP into 3-Hydroxyisovaleric Acid and ATP Catalysed by the Combined Action of Phosphate Butyryltransferase from *Bacillus subtilis* and Butyrate Kinase from *Lactobacillus casei* or *Geobacillus* sp.

The enzymatic assays were conducted in a total reaction volume of 0.2 ml.

The standard reaction mixture contained:
50 mM potassium phosphate buffer pH 7.5
4 mM 3-hydroxyisovaleryl-CoA
4 mM ADP
10 mM $MgCl_2$
10 mM NaCl
0.2 mg/ml of purified phosphate butyryltransferase from *Bacillus subtilis*
0.2 mg/ml of purified butyrate kinase from *Lactobacillus casei* or *Geobacillus* sp.

A series of controls were performed in parallel (Assays C-H; Table 4).

TABLE 4

| | Assay composition | | | | | | | |
|---|---|---|---|---|---|---|---|---|
| | A | B | C | D | E | F | G | H |
| 3-hydroxyisovaleryl-CoA | + | + | + | + | + | + | + | + |
| ADP | + | + | | | + | + | + | + |
| phosphate butyryltransferase from *Bacillus subtilis* | + | + | + | + | + | | | |
| butyrate kinase from *Lactobacillus casei* | + | | + | | | + | | |
| butyrate kinase from *Geobacillus* sp | | + | | + | | | + | |

The assays were then incubated for 20 min with shaking at 30° C.

After an incubation period, the reactions were stopped by heating the reaction medium 4 min at 90° C. The samples were centrifuged, filtered through a 0.22 μm filter and the clarified supernatants were transferred into a clean vial for further analysis. The consumption of ADP and 3-hydroxyisovaleryl-CoA, and the formation of ATP, 3-hydroxyisovaleric acid and free coenzyme A (CoA-SH) were followed by using HPLC-based methods.

HPLC-Based Analysis of ADP, ATP and 3-Hydroxyisovaleric Acid

HPLC analysis was performed using 1260 Infinity LC System (Agilent), equipped with column heating module and RI detector. 2 μl of samples were separated on Polaris C18-A column (150×4.6 mm, 5 μm particle size, column temp. 30° C.) with a mobile phase flow rate of 1.5 ml/min. The separation was performed using 8.4 mM sulfuric acid in $H_2O$/MeOH mixed solution (99/1) (V/V). In these conditions, the retention time of ADP, ATP and 3-hydroxyisovaleric acid were 2.09 min, 2.26 min and 5.01 min, respectively.

HPLC Based Analysis of 3-Hydroxyisovaleryl-CoA and Free Coenzyme A (CoA-SH)

HPLC analysis was performed using 1260 Infinity LC System (Agilent), equipped with column heating module and UV detector (260 nm). 1 µl of samples were separated on Zorbax SB-Aq column (250×4.6 mm, 5 µm particle size, column temp. 30° C.), with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). In these conditions, the retention time of 3-hydroxyisovaleryl-CoA and free coenzyme A (CoA-SH) were 4.53 and 4.10 min, respectively.

Typical chromatograms obtained for the enzymatic assay A and the enzyme-free assay H are shown in FIGS. 19 and 20.

The results of the HPLC analysis are summarized in FIG. 21.

The obtained data indicate that 3-hydroxyisovaleryl-CoA was converted into 3-hydroxyisovaleric acid with the concomitant generation of ATP from ADP in a two-step reaction, catalyzed respectively by two enzymes (assays A and B). Thus, the conversion occurred through the formation of the intermediate 3-hydroxyisovaleryl phosphate followed by transfer of the phosphate group from this intermediate on ADP, thereby releasing ATP.

A significant production of 3-hydroxyisovaleric acid, without simultaneous generation of ATP, was observed when phosphate butyryltransferase was used alone (assay E). This production is due to a spontaneous hydrolysis of the 3-hydroxyisovaleryl phosphate generated by the action of phosphate butyryltransferase.

The production of 3-hydroxyisovaleric acid was observed in the same manner for the control assays without ADP (assays C and D). This production was also due to a hydrolysis of the 3-hydroxyisovaleryl phosphate generated by the action of phosphate butyryltransferase.

Example 11: Conversion of 3-Hydroxyisovaleryl-CoA and ADP into 3-Hydroxyisovaleric Acid and ATP Catalysed by the Combined Action of the Phosphate Butyryltransferase from *Enterococcus faecalis* and Butyrate Kinase from *Lactobacillus casei* or *Geobacillus* sp.

The enzymatic assays were conducted in a total reaction volume of 0.2 ml.

The standard reaction mixture contained:

50 mM potassium phosphate buffer pH 7.5

4 mM 3-hydroxyisovaleryl-CoA 4 mM ADP 10 mM $MgCl_2$ 10 mM NaCl 0.2 mg/ml of purified phosphate butyryltransferase from *Enterococcus faecalis*

0.2 mg/ml of purified butyrate kinase from *Lactobacillus casei* or *Geobacillus* sp.

A series of controls were performed in parallel (Assays C-H Table 5).

TABLE 5

|  | Assay composition | | | | | | | |
|---|---|---|---|---|---|---|---|---|
|  | A | B | C | D | E | F | G | H |
| 3-hydroxyisovaleryl-CoA | + | + | + | + | + | + | + | + |
| ADP | + | + |  |  | + | + | + | + |
| phosphate butyryltransferase from *Enterococcus faecalis* | + | + | + | + | + |  |  |  |
| butyrate kinase from *Lactobacillus casei* | + |  | + |  |  | + |  |  |
| butyrate kinase from *Geobacillus* sp |  | + |  | + |  |  | + |  |

The assays were then incubated for 20 min with shaking at 30° C.

After an incubation period, the reactions were stopped by heating the reaction medium 4 min at 90° C. The samples were centrifuged, filtered through a 0.22 µm filter and the clarified supernatants were transferred into a clean vial for further analysis. The consumption of ADP and 3-hydroxyisovaleryl-CoA, and the formation of ATP and 3-hydroxyisovaleric acid and free coenzyme A (CoA-SH) were followed by HPLC analysis according to the methods described in Example 10.

The results of HPLC analysis are summarized in FIG. 22.

The obtained data indicate that the 3-hydroxyisovaleryl-CoA was converted into 3-hydroxyisovaleric acid with the concomitant generation of ATP from ADP in a two-step reaction, catalyzed respectively by two enzymes (assays A and B). Thus, the conversion occurred through the formation of the intermediate 3-hydroxyisovaleryl phosphate followed by transfer of the phosphate group from this intermediate on ADP, thereby releasing ATP.

A significant production of 3-hydroxyisovaleric acid, without simultaneous generation of ATP, was observed when phosphate butyryltransferase was used alone (assay E). This production was due to a hydrolysis of the 3-hydroxyisovaleryl phosphate generated by the action of phosphate butyryltransferase.

The production of 3-hydroxyisovaleric acid was observed in the same manner for the control assays without ADP (assays C and D). This production was also due to a hydrolysis of the 3-hydroxyisovaleryl phosphate generated by the action of phosphate butyryltransferase.

Example 12: Enzyme-Catalyzed Hydrolysis of 3-Methylcrotonyl-CoA into 3-Methylcrotonic Acid and Free Coenzyme-A The gene coding for acyl-CoA thioesterase II from *Pseudomonas putida* was synthesized according to the procedure as described in Example 1.

The vector pCA24N which contained the gene encoding acyl-CoA thioesterase 2 (TesB) from *Escherichia coli* was purchased from NAIST (Nara Institute of Science and Technology, Japan, ASKA collection). This vector provided contained a stretch of 6 histidine codons after the methionine initiation codon.

The corresponding enzymes were produced according to the procedure described in Example 1.

The enzymatic assays were conducted in a total reaction volume of 0.2 ml.

The standard reaction mixture contained:
50 mM HEPES pH 7.0
10 mM 3-methylcrotonyl-CoA (Sigma-Aldrich)
20 mM $MgCl_2$
20 mM NaCl
1 mg/ml of purified recombinant thioesterase.

Control assays were performed in which either no enzyme was added or no substrate was added.

The assays were incubated for 30 min with shaking at 30° C., the reactions were stopped by the addition of 0.1 ml of acetonitrile and the samples were then analyzed by HPLC-based procedure.

HPLC Based Analysis of the Consumption of 3-Methylcrotonyl-CoA and the Formation of 3-Methylcrotonic Acid and Free Coenzyme a (CoA-SH)

HPLC analysis was performed using an 1260 Infinity LC System (Agilent), equipped with a column heating module and a UV detector (210 nm). 5 µl of samples were separated on Zorbax SB-Aq column (250×4.6 mm, 5 µm particle size, column temp. 30° C.) with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). Commercial 3-methylcrotonyl-CoA, 3-methylcrotonic acid (Sigma-Aldrich) and CoA-SH (Sigma-Aldrich) were used as references. In these conditions, the retention time of free coenzyme A (CoA-SH), 3-methylcrotonyl-CoA and 3-methylcrotonic acid were 4.05, 5.38 and 5.83 min, respectively.

No 3-methylcrotonic acid signal was observed in control assays.

Both studied thioesterases catalyzed the hydrolysis of 3-methylcrotonyl-CoA with the formation of 3-methylcrotonic acid. An example of a chromatogram obtained with acyl-CoA thioesterase II from *Pseudomonas putida* is shown in FIG. 23.

The degree of production of 3-methylcrotonic acid as observed in the enzymatic assays is shown in Table 6.

TABLE 6

| Gene names | Organism | Uniprot Accession number | 3-methylcrotonic acid produced, mM |
|---|---|---|---|
| tesB | *Escherichia coli* | P0AGG2 | 0.6 |
| tesB | *Pseudomonas putida* | Q88DR1 | 3.1 |

Example 13: Conversion of 3-Methylcrotonyl-CoA and ADP into 3-Methylcrotonic Acid and ATP Catalysed by the Combined Action of Phosphate Butyryltransferase from *Bacillus subtilis* and Butyrate Kinase from *Lactobacillus casei* or *Geobacillus* sp.

In the assays described in the following, the following enzymes were used:

TABLE 7

| Gene names | Organism | Uniprot Accession number |
|---|---|---|
| Ptb (yqiS) | *Bacillus subtilis* | P54530 |
| Buk | *Lactobacillus casei* | K0N529 |
| BuK | *Geobacillus* sp. | L8A0E1 |

The enzymatic assays were conducted in a total reaction volume of 0.2 ml.

The standard reaction mixture contained:
50 mM potassium phosphate buffer pH 7.5
4 mM 3-methylcrotonyl-CoA
4 mM ADP
10 mM $MgCl_2$
10 mM NaCl
0.2 mg/ml of purified phosphate butyryltransferase from *Bacillus subtilis*
0.2 mg/ml of purified butyrate kinase from *Lactobacillus casei* or *Geobacillus* sp.

A series of controls was performed in parallel (Assays C-H as shown in Table 8).

TABLE 8

| | Assay composition | | | | | | | |
|---|---|---|---|---|---|---|---|---|
| | A | B | C | D | E | F | G | H |
| 3-methylcrotonyl-CoA | + | + | + | + | + | + | + | + |
| ADP | + | + | | | + | + | + | + |
| phosphate butyryltransferase from *Bacillus subtilis* | + | + | + | + | + | | | |
| butyrate kinase from *Lactobacillus casei* | + | | + | | | + | | |
| butyrate kinase from *Geobacillus* sp | | + | | + | | | + | |

Assays were then incubated for 20 min with shaking at 30° C.

After an incubation period, the reactions were stopped by heating the reaction medium 4 min at 90° C. The samples were centrifuged, filtered through a 0.22 µm filter and the clarified supernatants were transferred into a clean vial for further analysis. The consumption of ADP and 3-methylcrotonyl-CoA, and the formation of ATP, 3-methylcrotonic acid and free coenzyme A (CoA-SH) were followed by using HPLC-based methods.

HPLC-Based Analysis of ADP and ATP

HPLC analysis was performed using the 1260 Infinity LC System (Agilent) equipped with a column heating module and an RI detector. 2 µl of samples were separated on a Polaris C18-A column (150×4.6 mm, 5 µm particle size, column temp. 30° C.) with a mobile phase flow rate of 1.5 ml/min. The consumption of ADP and the formation of ATP were followed by HPLC analysis according to the methods described in Example 10.

HPLC Based Analysis of 3-Methylcrotonyl-CoA, 3-Methylcrotonic Acid and Free Coenzyme A (CoA-SH)

HPLC analysis was performed using the 1260 Infinity LC System (Agilent) equipped with a column heating module and a UV detector (260 nm). 1 µl of samples were separated on a Zorbax SB-Aq column (250×4.6 mm, 5 µm particle size, column temp. 30° C.), with a mobile phase flow rate of 1.5 ml/min.

The consumption of 3-methylcrotonyl-CoA and the formation of 3-methylcrotonic acid and free coenzyme A (CoA-SH) were followed according to the procedure described in Example 12. Under these conditions, the retention time of 3-methylcrotonyl-CoA, 3-methylcrotonic acid and free coenzyme A (CoA-SH) was 5.38 min, 5.73 min and 4.07 min, respectively.

Typical chromatograms obtained for the enzymatic assay A and enzyme-free assay H are shown in FIGS. 24a and 24b.

The results of the HPLC analysis are summarized in FIG. 25.

The obtained data indicate that 3-methylcrotonyl-CoA was converted into 3-methylcrotonic acid with the concomitant generation of ATP from ADP in a two-step reaction, catalyzed by two enzymes, respectively (assays A and B). Thus, the conversion occurred through the formation of the intermediate 3-methylcrotonyl phosphate followed by transfer of a phosphate group from this intermediate to ADP, thereby releasing ATP.

A significant production of 3-methylcrotonic acid without a simultaneous generation of ATP was observed when phosphate butyryltransferase was used alone (assay E).

This production is due to a spontaneous hydrolysis of 3-methylcrotonyl phosphate generated by the action of phosphate butyryltransferase.

The production of 3-methylcrotonic acid was observed in the same manner for the control assays without ADP (assays C and D). This production was also due to a hydrolysis of 3-methylcrotonyl phosphate generated by the action of phosphate butyryltransferase.

Example 14: Conversion of 3-Methylcrotonyl-CoA and ADP into 3-Methylcrotonic Acid and ATP Catalysed by the Combined Action of the Phosphate Butyryltransferase from *Enterococcus faecalis* and Butyrate Kinase from *Lactobacillus casei* or *Geobacillus* sp.

In the assays described in the following, the following enzymes were used:

TABLE 9

| Gene names | Organism | Uniprot Accession number |
|---|---|---|
| Ptb | *Enterococcus faecalis* | A0A038BNC2 |
| Buk | *Lactobacillus casei* | K0N529 |
| BuK | *Geobacillus* sp. | L8A0E1 |

The enzymatic assays were conducted in a total reaction volume of 0.2 ml.

The standard reaction mixture contained:

50 mM potassium phosphate buffer pH 7.5
4 mM 3-methylcrotonyl-CoA
4 mM ADP
10 mM $MgCl_2$
10 mM NaCl
0.2 mg/ml of purified phosphate butyryltransferase from *Enterococcus faecalis*
0.2 mg/ml of purified butyrate kinase from *Lactobacillus casei* or *Geobacillus* sp.

A series of controls was performed in parallel (Assays C-H Table 10).

TABLE 10

| | Assay composition | | | | | | | |
|---|---|---|---|---|---|---|---|---|
| | A | B | C | D | E | F | G | H |
| 3-methylcrotonyl-CoA | + | + | + | + | + | + | + | + |
| ADP | + | + | | | + | + | + | + |
| phosphate butyryltransferase from *Enterococcus faecalis* | + | + | + | + | + | | | |

TABLE 10-continued

| | Assay composition | | | | | | | |
|---|---|---|---|---|---|---|---|---|
| | A | B | C | D | E | F | G | H |
| butyrate kinase from *Lactobacillus casei* | + | | + | | | + | | |
| butyrate kinase from *Geobacillus* sp | | + | | + | | | + | |

Assays were then incubated for 20 min with shaking at 30° C.

After an incubation period, the reactions were stopped by heating the reaction medium 4 min at 90° C. The samples were centrifuged, filtered through a 0.22 µm filter and the clarified supernatants were transferred into a clean vial for further analysis. The consumption of ADP and 3-methylcrotonyl-CoA and the formation of ATP and 3-methylcrotonic acid and free coenzyme A (CoA-SH) were followed by HPLC analysis according to the methods described in Example 10 and Example 12.

The results of the HPLC analysis are summarized in FIG. 26.

The obtained data indicate that the 3-methylcrotonyl-CoA was converted into 3-methylcrotonic acid with the concomitant generation of ATP from ADP in a two-step reaction, catalyzed by two enzymes, respectively (assays A and B). Thus, the conversion occurred through the formation of the intermediate 3-methylcrotonyl phosphate followed by the transfer of a phosphate group from this intermediate on ADP, thereby releasing ATP.

A significant production of 3-methylcrotonic acid without simultaneous generation of ATP was observed when phosphate butyryltransferase was used alone (assay E).

This production was due to a hydrolysis of 3-methylcrotonyl phosphate generated by the action of phosphate butyryltransferase.

The production of 3-methylcrotonic acid was observed in a similar manner for the control assays without ADP (assays C and D). This production was also due to a hydrolysis of 3-methylcrotonyl phosphate generated by the action of phosphate butyryltransferase.

Example 15: Screening for Hydro-Lyases for the Production of 3-Hydroxy-3-Methylbutyric Acid from 3-Methylcrotonic Acid Hydro-lyases classified as enzymes belonging to the family of 2-methylcitrate dehydratases (EC 4.2.1.79) have already been described as being capable of converting 3-methylcrotonic acid into 3-hydroxy-3-methylbutyric acid. This has been described for a maleate hydratase from *Pseudomonas pseudoalcaligenes* which can use 3-methylcrotonic acid as a substrate (van der Werf et al., Appl. Environ. Microbiol. 59 (1993), 2823-2829).

Further hydro-lyases which show a corresponding reactivity for the enzymatic conversion of 3-methylcrotonic acid into 3-hydroxy-3-methylbutyric acid can be identified by screening known hydro-lyases for this reactivity as outlined in the following:

Corresponding genes encoding for enzymes belonging to the family of hydro-lyases classified as EC 4.2.1.-, preferably encoding for enzymes belonging to the family of aconitate hydratases (EC 4.2.1.3), maleate hydratases (EC 4.2.1.31) or 2-methylcitrate dehydratases (EC 4.2.1.79), can be derived from commonly available resources. The corresponding gene of a candidate enzyme can be synthesized and the enzyme can be produced according to the procedure as described in Example 1.

Once the enzyme is produced and purified in accordance with the above description, the respective hydro-lyase can be tested with respect to its reactivity for the enzymatic conversion of 3-methylcrotonic acid into 3-hydroxy-3-methylbutyric acid. For this hydratase assay, a reaction mixture containing $MgCl_2$, NaCl and 0-100 mM 3-methylcrotonic acid is used. Control assays are performed in which either no enzyme is added or no substrate is added. Each sample is monitored for the consumption of 3-methylcrotonic acid and/or for the formation of 3-hydroxy-3-methylbutyric acid by HPLC-based procedure.

A hydro-lyase will be identified as a suitable enzyme capable of enzymatically converting 3-methylcrotonic acid into 3-hydroxy-3-methylbutyric if it shows in the above assay an increased formation of 3-hydroxy-3-methylbutyric acid over the control assays.

The invention claimed is:

1. A method for the conversion of 3-methylcrotonyl-CoA into 3-hydroxy-3-methylbutyric acid comprising the steps of:
   (a) enzymatically converting 3-methylcrotonyl-CoA into 3-hydroxy-3-methylbutyryl-CoA by a first enzyme having at least 95% sequence identity to one of SEQ ID NOs:1-3 or 6 wherein said first enzyme is capable of converting 3-methylcrotonyl-CoA into 3-hydroxy-3-methylbutyryl-CoA; and
   (b) enzymatically converting the thus produced 3-hydroxy-3-methylbutyryl-CoA into 3-hydroxy-3-methylbutyryl phosphate by a second enzyme having at least 95% sequence identity to one of SEQ ID NOs:28 or 29 wherein said second enzyme is capable of converting 3-hydroxy-3-methylbutyryl-CoA into 3-hydroxy-3-methylbutyryl phosphate; and
   (c) enzymatically converting the thus produced 3-hydroxy-3-methylbutyryl phosphate into 3-hydroxy-3-methylbutyric acid by a third enzyme having at least 95% sequence identity to one of SEQ ID NOS:30 or 31 wherein said third enzyme is capable of converting 3-hydroxy-3-methylbutyryl phosphate into 3-hydroxy-3-methylbutyric acid.

2. The method of claim 1, wherein the first enzyme, the second enzyme and the third enzyme are in a composition.

3. The method of claim 2, wherein 3-hydroxy-3-methylbutyric acid is recovered.

4. The method of claim 2, wherein the 3-hydroxy-3-methylbutyric acid is further converted into isobutene.

5. The method of claim 4, wherein the isobutene is recovered.

6. The method of claim 1, wherein the first enzyme, the second enzyme and the third enzyme are expressed in a microorganism.

7. The method of claim 6, wherein the microorganism produces 3-hydroxy-3-methylbutyric acid.

8. The method of claim 7, wherein 3-hydroxy-3-methylbutyric acid is recovered.

9. The method of claim 7, wherein the 3-hydroxy-3-methylbutyric acid is further converted into isobutene.

10. The method of claim 9, wherein the isobutene is recovered.

11. The method of claim 6, wherein 3-hydroxy-3-methylbutyric acid is recovered.

12. The method of claim 6, wherein the 3-hydroxy-3-methylbutyric acid is further converted into isobutene.

13. The method of claim 12, wherein the isobutene is recovered.

14. The method of claim 1, wherein 3-hydroxy-3-methylbutyric acid is recovered.

15. The method of claim 1, wherein the 3-hydroxy-3-methylbutyric acid is further converted into isobutene.

16. The method of claim 15, wherein the isobutene is recovered.

* * * * *

UNITED STATES PATENT AND TRADEMARK OFFICE
CERTIFICATE OF CORRECTION

PATENT NO. : 10,676,765 B2
APPLICATION NO. : 15/511684
DATED : June 9, 2020
INVENTOR(S) : Philippe Marlière, Maria Anissimova and Mathieu Allard Page 1 of 1

It is certified that error appears in the above-identified patent and that said Letters Patent is hereby corrected as shown below:

On the Title Page

Item (73), the Assignee name, city and country should be added:
--Scientist of Fortune, S.A., Luxembourg (LU)
Evry Cedex--.

Item (30), the Foreign Application Priority Data should include:
--Sept. 17, 2014 (EP) 14185180--.

Signed and Sealed this
Twentieth Day of October, 2020

Andrei Iancu
*Director of the United States Patent and Trademark Office*